US012796987B2

(12) United States Patent
Bahney et al.

(10) Patent No.: US 12,796,987 B2
(45) Date of Patent: *Nov. 17, 2026

(54) PHYSIOLOGICAL MONITORING DEVICE

(71) Applicant: iRhythm Technologies, Inc., San Francisco, CA (US)

(72) Inventors: Timothy J. Bahney, San Francisco, CA (US); Hung H. Ho, San Francisco, CA (US); Shena H. Park, San Francisco, CA (US); Genaro S. Sepulveda, San Francisco, CA (US); Mark J. Day, San Francisco, CA (US); Yuriko Tamura, Belmont, CA (US)

(73) Assignee: IRHYTHM TECHNOLOGIES, INC., San Francisco, CA (US)

(*) Notice: Subject to any disclaimer, the term of this patent is extended or adjusted under 35 U.S.C. 154(b) by 94 days.

This patent is subject to a terminal disclaimer.

(21) Appl. No.: 19/187,871

(22) Filed: Apr. 23, 2025

(65) Prior Publication Data

US 2026/0007345 A1 Jan. 8, 2026

Related U.S. Application Data

(63) Continuation of application No. 18/301,881, filed on Apr. 17, 2023, now Pat. No. 12,357,212, which is a (Continued)

(51) Int. Cl.

*A61B 5/00* (2006.01)
*A61B 5/25* (2021.01)

(Continued)

(52) U.S. Cl.

CPC ................ *A61B 5/257* (2021.01); *A61B 5/28* (2021.01); *A61B 5/6833* (2013.01); *A61B 5/721* (2013.01);

(Continued)

(58) Field of Classification Search

CPC ..... A61B 5/04; A61B 5/0408; A61B 5/04085; A61B 5/04087; A61B 5/0492;

(Continued)

(56) References Cited

U.S. PATENT DOCUMENTS 1,497,079 A 6/1924 Gullborg
2,179,922 A 11/1939 Dana (Continued)

FOREIGN PATENT DOCUMENTS

AU 2011252998 8/2015
AU 2014209376 6/2017

(Continued)

OTHER PUBLICATIONS

US 8,750,980 B2, 06/2014, Katra et al. (withdrawn)

(Continued)

*Primary Examiner* — Joseph A Stoklosa
*Assistant Examiner* — Brian M Antiskay
(74) *Attorney, Agent, or Firm* — Knobbe, Martens, Olson & Bear, LLP

(57) ABSTRACT

The present invention relates to a physiological monitoring device. Some embodiments of the invention allow for long-term monitoring of physiological signals. Further embodiments may also allow for the monitoring of secondary signals such as motion.

9 Claims, 17 Drawing Sheets

Related U.S. Application Data continuation of application No. 16/786,831, filed on Feb. 10, 2020, now Pat. No. 11,627,902, which is a continuation of application No. 16/397,651, filed on Apr. 29, 2019, now Pat. No. 10,555,683, which is a continuation of application No. 16/006,719, filed on Jun. 12, 2018, now Pat. No. 10,271,754, which is a continuation of application No. 14/162,656, filed on Jan. 23, 2014, now abandoned.

(60) Provisional application No. 61/756,326, filed on Jan. 24, 2013.

(51) Int. Cl.
*A61B 5/257* (2021.01)
*A61B 5/28* (2021.01)

(52) U.S. Cl.
CPC ................. *A61B 2562/0219* (2013.01); *A61B 2562/125* (2013.01); *A61B 2562/164* (2013.01)

(58) Field of Classification Search
CPC ................ A61B 5/0531; A61B 5/6801; A61B 5/6832–6833
USPC .................................... 600/382–393, 50–509
See application file for complete search history.

(56) References Cited

U.S. PATENT DOCUMENTS 2,201,645 A 5/1940 Epner
2,311,060 A 2/1943 Lurrain
2,444,552 A 7/1948 Sigurd
2,500,840 A 3/1950 Lyons
3,215,136 A 11/1965 Holter et al.
3,547,107 A 12/1970 Chapman et al.
3,697,706 A 10/1972 Huggard
3,870,034 A 3/1975 James
3,882,853 A 5/1975 Gofman
3,911,906 A 10/1975 Reinhold
3,943,918 A 3/1976 Lewis
3,949,388 A 4/1976 Fuller
3,986,495 A 10/1976 Miller
4,023,312 A 5/1977 Stickney
4,027,664 A 6/1977 Heavner, Jr. et al.
4,082,087 A 4/1978 Howson
4,121,573 A 10/1978 Crovella et al.
4,123,785 A 10/1978 Cherry et al.
4,126,126 A 11/1978 Bare
4,202,139 A 5/1980 Hong et al.
4,274,419 A 6/1981 Tam et al.
4,274,420 A 6/1981 Hymes
4,280,507 A 7/1981 Rosenberg
4,286,610 A 9/1981 Jones
4,333,475 A 6/1982 Moreno et al.
4,361,990 A 12/1982 Link
4,381,792 A 5/1983 Busch
4,438,767 A 3/1984 Nelson
4,459,987 A 7/1984 Pangburn
4,535,783 A 8/1985 Marangoni
4,537,207 A 8/1985 Gilhaus
4,572,187 A 2/1986 Schetrumpf
4,621,465 A 11/1986 Pangburn
4,622,979 A 11/1986 Katchis et al.
4,623,206 A 11/1986 Fuller
4,658,826 A 4/1987 Weaver
4,712,552 A 12/1987 Pangburn
4,736,752 A 4/1988 Munck et al.
4,763,660 A 8/1988 Kroll et al.
4,795,516 A 1/1989 Strand
4,855,294 A 8/1989 Patel
4,925,453 A 5/1990 Kannankeril
4,938,228 A 7/1990 Righter et al.
4,951,672 A 8/1990 Buchwald et al.
4,981,141 A 1/1991 Segalowitz
5,003,987 A 4/1991 Grinwald
5,027,824 A 7/1991 Dougherty et al.
5,082,851 A 1/1992 Appelbaum et al.
5,086,778 A 2/1992 Mueller et al.
5,093,036 A 3/1992 Shafe et al.
5,169,679 A 12/1992 Palanisamy
5,191,891 A 3/1993 Righter
5,205,295 A 4/1993 Del Mar et al.
5,226,425 A 7/1993 Righter
5,228,450 A 7/1993 Sellers
5,230,119 A 7/1993 Woods et al.
5,289,824 A 3/1994 Mills et al.
5,305,746 A 4/1994 Fendrock
5,309,909 A 5/1994 Gadsby
5,328,935 A 7/1994 Van Phan
5,365,935 A 11/1994 Righter et al.
5,458,141 A 10/1995 Neil
5,483,967 A 1/1996 Ohtake
5,489,624 A 2/1996 Kantner et al.
5,511,548 A 4/1996 Riazzi et al.
5,511,553 A 4/1996 Segalowitz
5,515,858 A 5/1996 Myllymaki
5,536,768 A 7/1996 Kantner et al.
5,581,369 A 12/1996 Righter et al.
5,626,140 A 5/1997 Feldman et al.
5,634,468 A 6/1997 Platt et al.
5,645,063 A 7/1997 Straka
5,645,068 A 7/1997 Mezack et al.
5,730,143 A 3/1998 Schwarzberg
5,738,104 A 4/1998 Lo et al.
5,749,365 A 5/1998 Magill
5,749,367 A 5/1998 Gamlyn et al.
5,771,524 A 6/1998 Woods et al.
5,772,604 A 6/1998 Langberg et al.
5,776,072 A 7/1998 Hsu et al.
5,881,743 A 3/1999 Nadel
D408,541 S 4/1999 Dunshee et al.
5,916,239 A 6/1999 Geddes et al.
5,922,489 A 7/1999 Adachi
5,931,791 A 8/1999 Saltzstein et al.
5,941,829 A 8/1999 Saltzstein et al.
5,957,854 A 9/1999 Besson et al.
5,959,529 A 9/1999 Kail
5,995,861 A 11/1999 Price
6,013,007 A 1/2000 Root et al.
6,032,060 A 2/2000 Carim
6,038,464 A 3/2000 Axelgaard et al.
6,038,469 A 3/2000 Karlsson et al.
6,044,515 A 4/2000 Zygmont
6,073,046 A 6/2000 Patel et al.
6,093,146 A 7/2000 Filangeri
D429,336 S 8/2000 Francis et al.
6,102,856 A 8/2000 Groff et al.
6,117,077 A 9/2000 Del Mar et al.
6,121,508 A 9/2000 Bischof
6,132,371 A 10/2000 Dempsey et al.
6,134,480 A 10/2000 Minogue
6,136,008 A 10/2000 Becker et al.
6,161,036 A 12/2000 Matsumura et al.
6,169,915 B1 1/2001 Krumbiegel et al.
6,178,357 B1 1/2001 Gliner et al.
6,200,265 B1 3/2001 Walsh et al.
6,223,080 B1 4/2001 Thompson
6,225,901 B1 5/2001 Kail
6,229,098 B1 5/2001 Dunn et al.
6,232,366 B1 5/2001 Wang et al.
6,238,338 B1 5/2001 DeLuca et al.
6,248,115 B1 6/2001 Halk
6,267,723 B1 7/2001 Matsumura et al.
6,287,252 B1 9/2001 Lugo
6,289,238 B1 9/2001 Besson et al.
6,290,707 B1 9/2001 Street
6,315,719 B1 11/2001 Rode et al.
6,341,230 B1 1/2002 Koike et al.
6,379,237 B1 4/2002 Gordon
6,385,473 B1 5/2002 Haines et al.
6,389,308 B1 5/2002 Shusterman
6,416,471 B1 7/2002 Kumar et al.
6,434,410 B1 8/2002 Cordero et al.

(56) References Cited

U.S. PATENT DOCUMENTS

| | | | |
|---|---|---|---|
| 6,441,747 | B1 | 8/2002 | Khair et al. |
| 6,453,186 | B1 | 9/2002 | Lovejoy et al. |
| 6,454,708 | B1 | 9/2002 | Ferguson et al. |
| 6,456,871 | B1 | 9/2002 | Hsu et al. |
| 6,456,872 | B1 | 9/2002 | Faisandier |
| 6,464,815 | B1 | 10/2002 | Beaudry |
| 6,493,898 | B1 | 12/2002 | Woods et al. |
| 6,494,829 | B1 | 12/2002 | New, Jr. et al. |
| 6,496,705 | B1 | 12/2002 | Ng et al. |
| 6,510,339 | B2 | 1/2003 | Kovtun et al. |
| 6,546,285 | B1 | 4/2003 | Owen et al. |
| 6,564,090 | B2 | 5/2003 | Taha et al. |
| 6,569,095 | B2 | 5/2003 | Eggers |
| 6,577,893 | B1 | 6/2003 | Besson et al. |
| 6,580,942 | B1 | 6/2003 | Willshire |
| 6,585,707 | B2 | 7/2003 | Cabiri et al. |
| 6,589,170 | B1 | 7/2003 | Flach et al. |
| 6,589,187 | B1 | 7/2003 | Dimberger et al. |
| 6,605,046 | B1 | 8/2003 | Del Mar et al. |
| 6,615,083 | B2 | 9/2003 | Kupper |
| 6,622,035 | B1 | 9/2003 | Merilainen |
| 6,623,312 | B2 | 9/2003 | Merry et al. |
| 6,626,865 | B1 | 9/2003 | Prisell |
| 6,656,125 | B2 | 12/2003 | Misczynski et al. |
| 6,664,893 | B1 | 12/2003 | Eveland et al. |
| 6,665,385 | B2 | 12/2003 | Rogers et al. |
| 6,690,959 | B2 | 2/2004 | Thompson |
| 6,694,177 | B2 | 2/2004 | Eggers et al. |
| 6,701,184 | B2 | 3/2004 | Henkin |
| 6,711,427 | B1 | 3/2004 | Ketelhohn |
| 6,730,028 | B2 | 5/2004 | Eppstein |
| D492,607 | S | 7/2004 | Curkovic et al. |
| 6,773,396 | B2 | 8/2004 | Flach et al. |
| 6,775,566 | B2 | 8/2004 | Nissila |
| 6,801,137 | B2 | 10/2004 | Eggers |
| 6,801,802 | B2 | 10/2004 | Sitzman et al. |
| 6,871,089 | B2 | 3/2005 | Korzinov et al. |
| 6,871,211 | B2 | 3/2005 | Labounty et al. |
| 6,875,174 | B2 | 4/2005 | Braun et al. |
| 6,881,191 | B2 | 4/2005 | Oakley et al. |
| 6,893,396 | B2 | 5/2005 | Schulze et al. |
| 6,897,788 | B2 | 5/2005 | Khair et al. |
| 6,904,312 | B2 | 6/2005 | Bardy |
| 6,925,324 | B2 | 8/2005 | Shusterman |
| 6,940,403 | B2 | 9/2005 | Kail |
| 6,954,163 | B2 | 10/2005 | Toumazou et al. |
| 6,957,107 | B2 | 10/2005 | Rogers et al. |
| 6,987,965 | B2 | 1/2006 | Ng et al. |
| 7,002,468 | B2 | 2/2006 | Eveland et al. |
| 7,020,508 | B2 | 3/2006 | Stivoric et al. |
| 7,024,248 | B2 | 4/2006 | Penner et al. |
| 7,031,770 | B2 | 4/2006 | Collins et al. |
| 7,072,708 | B1 | 7/2006 | Andresen et al. |
| 7,072,709 | B2 | 7/2006 | Xue |
| 7,076,283 | B2 | 7/2006 | Cho et al. |
| 7,076,287 | B2 | 7/2006 | Rowlandson |
| 7,076,288 | B2 | 7/2006 | Skinner |
| 7,076,289 | B2 | 7/2006 | Sarkar et al. |
| 7,079,977 | B2 | 7/2006 | Osorio et al. |
| 7,082,327 | B2 | 7/2006 | Houben |
| 7,089,048 | B2 | 8/2006 | Matsumura et al. |
| 7,099,715 | B2 | 8/2006 | Korzinov et al. |
| 7,117,031 | B2 | 10/2006 | Lohman et al. |
| 7,120,485 | B2 | 10/2006 | Glass et al. |
| 7,130,396 | B2 | 10/2006 | Rogers et al. |
| 7,161,484 | B2 | 1/2007 | Tsoukalis |
| 7,171,166 | B2 | 1/2007 | Ng et al. |
| 7,179,152 | B1 | 2/2007 | Rhoades |
| 7,186,264 | B2 | 3/2007 | Liddicoat et al. |
| 7,193,264 | B2 | 3/2007 | Lande |
| 7,194,300 | B2 | 3/2007 | Korzinov |
| 7,206,630 | B1 | 4/2007 | Tarler |
| 7,212,850 | B2 | 5/2007 | Prystowsky et al. |
| 7,222,054 | B2 | 5/2007 | Geva |
| 7,242,318 | B2 | 7/2007 | Harris |
| 7,266,361 | B2 | 9/2007 | Burdett |
| 7,316,671 | B2 | 1/2008 | Lastovich et al. |
| 7,349,947 | B1 | 3/2008 | Slage et al. |
| D567,949 | S | 4/2008 | Lash et al. |
| 7,354,423 | B2 | 4/2008 | Zelickson et al. |
| 7,382,247 | B2 | 6/2008 | Welch et al. |
| 7,387,607 | B2 | 6/2008 | Holt et al. |
| 7,395,106 | B2 | 7/2008 | Ryu et al. |
| 7,433,731 | B2 | 10/2008 | Matsumura et al. |
| 7,444,177 | B2 | 10/2008 | Nazeri |
| 7,468,032 | B2 | 12/2008 | Stahmann et al. |
| D584,414 | S | 1/2009 | Lash et al. |
| 7,477,933 | B2 | 1/2009 | Ueyama |
| 7,478,108 | B2 | 1/2009 | Townsend et al. |
| 7,481,772 | B2 | 1/2009 | Banet |
| 7,482,314 | B2 | 1/2009 | Grimes et al. |
| 7,502,643 | B2 | 3/2009 | Farringdon et al. |
| 7,539,533 | B2 | 5/2009 | Tran |
| 7,542,878 | B2 | 6/2009 | Nanikashvili |
| D600,351 | S | 9/2009 | Phillips et al. |
| 7,587,237 | B2 | 9/2009 | Korzinov et al. |
| 7,630,756 | B2 | 12/2009 | Linker |
| 7,632,174 | B2 | 12/2009 | Gringer et al. |
| D607,570 | S | 1/2010 | Phillips et al. |
| 7,672,714 | B2 | 3/2010 | Kuo et al. |
| 7,715,905 | B2 | 5/2010 | Kurzweil et al. |
| D618,357 | S | 6/2010 | Navies |
| 7,729,753 | B2 | 6/2010 | Kremliovsky et al. |
| 7,733,224 | B2 | 6/2010 | Tran |
| 7,761,143 | B2 | 7/2010 | Matsumura et al. |
| D621,048 | S | 8/2010 | Severe et al. |
| 7,815,494 | B2 | 10/2010 | Gringer et al. |
| 7,841,039 | B1 | 11/2010 | Squire |
| 7,889,070 | B2 | 2/2011 | Reeves et al. |
| 7,894,888 | B2 | 2/2011 | Chan et al. |
| D634,431 | S | 3/2011 | Severe et al. |
| 7,904,133 | B2 | 3/2011 | Gehman et al. |
| 7,907,956 | B2 | 3/2011 | Uhlik |
| 7,907,996 | B2 | 3/2011 | Prystowsky et al. |
| 7,941,207 | B2 | 5/2011 | Korzinov |
| D639,437 | S | 6/2011 | Bishay et al. |
| 7,970,450 | B2 | 6/2011 | Kroecker et al. |
| 7,979,111 | B2 | 7/2011 | Acquista |
| 7,996,075 | B2 | 8/2011 | Korzinov et al. |
| 7,996,187 | B2 | 8/2011 | Nanikashvili et al. |
| 8,002,701 | B2 | 8/2011 | John et al. |
| D645,968 | S | 9/2011 | Kasabach et al. |
| D650,911 | S | 12/2011 | Odeh |
| 8,077,042 | B2 | 12/2011 | Peeters |
| 8,103,333 | B2 | 1/2012 | Tran |
| 8,108,036 | B2 | 1/2012 | Tran |
| 8,116,841 | B2 | 2/2012 | Bly et al. |
| 8,150,502 | B2 | 4/2012 | Kumar et al. |
| 8,156,945 | B2 | 4/2012 | Hart |
| 8,160,682 | B2 | 4/2012 | Kumar et al. |
| D659,836 | S | 5/2012 | Bensch et al. |
| 8,170,639 | B2 | 5/2012 | Hauge |
| 8,200,319 | B2 | 6/2012 | Pu et al. |
| 8,200,320 | B2 | 6/2012 | Kovacs |
| D663,432 | S | 7/2012 | Nichols |
| 8,214,007 | B2 | 7/2012 | Baker et al. |
| 8,244,335 | B2 | 8/2012 | Kumar et al. |
| 8,249,686 | B2 | 8/2012 | Libbus et al. |
| 8,261,754 | B2 | 9/2012 | Pitstick |
| 8,265,907 | B2 | 9/2012 | Nanikashvili et al. |
| RE43,767 | E | 10/2012 | Eggers et al. |
| 8,280,749 | B2 | 10/2012 | Hsieh et al. |
| 8,285,356 | B2 | 10/2012 | Bly et al. |
| 8,290,129 | B2 | 10/2012 | Rogers et al. |
| 8,290,574 | B2 | 10/2012 | Field et al. |
| 8,301,219 | B2 | 10/2012 | Chen et al. |
| 8,301,236 | B2 | 10/2012 | Baumann et al. |
| 8,311,604 | B2 | 11/2012 | Rowlandson et al. |
| 8,315,687 | B2 | 11/2012 | Cross et al. |
| 8,315,695 | B2 | 11/2012 | Sebelius et al. |
| 8,323,188 | B2 | 12/2012 | Tran |
| 8,326,394 | B2 | 12/2012 | Rowlandson et al. |
| 8,326,407 | B2 | 12/2012 | Linker |
| 8,328,718 | B2 | 12/2012 | Tran |

(56) References Cited

U.S. PATENT DOCUMENTS

| | | | |
|---|---|---|---|
| 8,334,464 | B2 | 12/2012 | Edwards et al. |
| D674,009 | S | 1/2013 | Nichols |
| 8,343,116 | B2 | 1/2013 | Ignon |
| 8,369,936 | B2 | 2/2013 | Farringdon et al. |
| 8,374,688 | B2 | 2/2013 | Libbus et al. |
| 8,386,009 | B2 | 2/2013 | Lindberg et al. |
| 8,388,543 | B2 | 3/2013 | Chon et al. |
| 8,406,843 | B2 | 3/2013 | Tiegs et al. |
| 8,412,317 | B2 | 4/2013 | Mazar |
| 8,417,326 | B2 | 4/2013 | Chon et al. |
| 8,425,414 | B2 | 4/2013 | Eveland |
| D682,437 | S | 5/2013 | Olson et al. |
| 8,449,471 | B2 | 5/2013 | Tran |
| 8,452,356 | B2 | 5/2013 | Vestel et al. |
| 8,460,189 | B2 | 6/2013 | Libbus et al. |
| 8,473,039 | B2 | 6/2013 | Michelson et al. |
| 8,473,047 | B2 | 6/2013 | Chakravarthy et al. |
| 8,478,418 | B2 | 7/2013 | Fahey |
| 8,483,809 | B2 | 7/2013 | Kim et al. |
| 8,500,636 | B2 | 8/2013 | Tran |
| 8,515,529 | B2 | 8/2013 | Pu et al. |
| 8,525,673 | B2 | 9/2013 | Tran |
| 8,535,223 | B2 | 9/2013 | Corroy et al. |
| 8,538,503 | B2 | 9/2013 | Kumar et al. |
| 8,540,731 | B2 | 9/2013 | Kay |
| 8,560,046 | B2 | 10/2013 | Kumar et al. |
| 8,562,527 | B2 | 10/2013 | Braun et al. |
| 8,571,645 | B2 | 10/2013 | Wu et al. |
| 8,588,908 | B2 | 11/2013 | Moorman et al. |
| 8,591,430 | B2 | 11/2013 | Amurthur et al. |
| 8,591,599 | B1 | 11/2013 | Kaliki |
| 8,594,763 | B1 | 11/2013 | Bibian |
| 8,613,709 | B2 | 12/2013 | Bishay et al. |
| 8,626,262 | B2 | 1/2014 | McGusty et al. |
| 8,630,699 | B2 | 1/2014 | Baker et al. |
| 8,632,463 | B2 | 1/2014 | Drinan et al. |
| 8,639,319 | B2 | 1/2014 | Hugh et al. |
| 8,647,268 | B2 | 2/2014 | Tran |
| 8,668,643 | B2 | 3/2014 | Kinast |
| 8,684,900 | B2 | 4/2014 | Tran |
| 8,684,925 | B2 | 4/2014 | Amurthur et al. |
| 8,688,189 | B2 | 4/2014 | Shennib |
| 8,688,190 | B2 | 4/2014 | Libbus et al. |
| 8,688,202 | B2 | 4/2014 | Brockway et al. |
| 8,718,742 | B2 | 5/2014 | Beck et al. |
| 8,718,752 | B2 | 5/2014 | Libbus et al. |
| 8,718,753 | B2 | 5/2014 | Chon et al. |
| 8,731,632 | B1 | 5/2014 | Sereboff et al. |
| 8,738,118 | B2 | 5/2014 | Moon et al. |
| 8,744,561 | B2 | 6/2014 | Fahey |
| 8,750,974 | B2 | 6/2014 | Baker et al. |
| 8,755,876 | B2 | 6/2014 | Chon et al. |
| 8,782,308 | B2 | 7/2014 | Vlach |
| 8,789,727 | B2 | 7/2014 | Mortazavi |
| 8,790,257 | B2 | 7/2014 | Libbus et al. |
| 8,795,174 | B2 | 8/2014 | Manicka et al. |
| 8,818,481 | B2 | 8/2014 | Bly et al. |
| 8,823,490 | B2 | 9/2014 | Libbus et al. |
| 8,838,218 | B2 | 9/2014 | Khair |
| 8,858,450 | B2 | 10/2014 | Chon et al. |
| 8,874,185 | B2 | 10/2014 | Sonnenborg |
| D719,267 | S | 12/2014 | Vaccarella |
| 8,903,477 | B2 | 12/2014 | Berkner |
| 8,903,484 | B2 | 12/2014 | Mazar |
| 8,909,328 | B2 | 12/2014 | Chon |
| 8,909,330 | B2 | 12/2014 | McCombie et al. |
| 8,909,332 | B2 | 12/2014 | Vitali et al. |
| 8,909,333 | B2 | 12/2014 | Rossi |
| 8,909,832 | B2 | 12/2014 | Vlach et al. |
| 8,926,509 | B2 | 1/2015 | Magar et al. |
| 8,945,019 | B2 | 2/2015 | Prystowsky et al. |
| 8,948,854 | B2 | 2/2015 | Friedman et al. |
| 8,954,129 | B1 | 2/2015 | Schlegel et al. |
| 8,956,293 | B2 | 2/2015 | McCombie et al. |
| 8,965,492 | B2 | 2/2015 | Baker et al. |
| 8,968,195 | B2 | 3/2015 | Tran |
| 8,972,000 | B2 | 3/2015 | Manera |
| 8,979,755 | B2 | 3/2015 | Szydlo-Moore et al. |
| 9,014,777 | B2 | 4/2015 | Woo |
| 9,015,008 | B2 | 4/2015 | Geva et al. |
| 9,017,255 | B2 | 4/2015 | Raptis et al. |
| 9,017,256 | B2 | 4/2015 | Gottesman |
| 9,021,161 | B2 | 4/2015 | Vlach et al. |
| 9,021,165 | B2 | 4/2015 | Vlach |
| 9,026,190 | B2 | 5/2015 | Shenasa et al. |
| 9,037,223 | B2 | 5/2015 | Oral et al. |
| 9,044,148 | B2 | 6/2015 | Michelson et al. |
| 9,084,548 | B2 | 7/2015 | Bouguerra |
| 9,095,274 | B2 | 8/2015 | Fein et al. |
| 9,101,264 | B2 | 8/2015 | Acquista |
| 9,138,144 | B2 | 9/2015 | Geva |
| 9,149,228 | B2 | 10/2015 | Kinast |
| 9,155,484 | B2 | 10/2015 | Baker et al. |
| 9,173,670 | B2 | 11/2015 | Sepulveda et al. |
| 9,179,851 | B2 | 11/2015 | Baumann et al. |
| D744,659 | S | 12/2015 | Bishay et al. |
| 9,211,076 | B2 | 12/2015 | Kim |
| 9,226,679 | B2 | 1/2016 | Balda |
| 9,241,649 | B2 | 1/2016 | Kumar et al. |
| 9,241,650 | B2 | 1/2016 | Amirim |
| 9,277,864 | B2 | 3/2016 | Yang et al. |
| 9,277,871 | B2 | 3/2016 | Keenan et al. |
| 9,282,894 | B2 | 3/2016 | Banet et al. |
| 9,307,921 | B2 | 4/2016 | Friedman et al. |
| 9,345,414 | B1 | 5/2016 | Bardy et al. |
| 9,355,215 | B2 | 5/2016 | Vlach |
| D759,653 | S | 6/2016 | Toth et al. |
| 9,357,939 | B1 | 6/2016 | Nosrati |
| 9,364,150 | B2 | 6/2016 | Sebelius et al. |
| 9,364,155 | B2 | 6/2016 | Bardy et al. |
| 9,398,853 | B2 | 7/2016 | Nanikashvili |
| 9,408,545 | B2 | 8/2016 | Felix et al. |
| 9,408,551 | B2 | 8/2016 | Bardy et al. |
| 9,408,576 | B2 | 8/2016 | Chon et al. |
| 9,414,753 | B2 | 8/2016 | Chon et al. |
| 9,414,786 | B1 | 8/2016 | Brockway et al. |
| D766,447 | S | 9/2016 | Bishay et al. |
| 9,433,367 | B2 | 9/2016 | Felix et al. |
| 9,433,380 | B1 | 9/2016 | Bishay et al. |
| 9,439,566 | B2 | 9/2016 | Arne et al. |
| 9,439,599 | B2 | 9/2016 | Thompson et al. |
| 9,445,719 | B2 | 9/2016 | Libbus et al. |
| 9,451,890 | B2 | 9/2016 | Gitlin et al. |
| 9,451,975 | B2 | 9/2016 | Sepulveda et al. |
| 9,469,599 | B2 | 10/2016 | Kanj et al. |
| 9,474,445 | B2 | 10/2016 | Eveland |
| 9,474,461 | B2 | 10/2016 | Fisher et al. |
| 9,478,998 | B1 | 10/2016 | Lapetina et al. |
| D773,056 | S | 11/2016 | Vlach |
| 9,492,084 | B2 | 11/2016 | Behar et al. |
| 9,504,423 | B1 | 11/2016 | Bardy et al. |
| D775,361 | S | 12/2016 | Vosch et al. |
| 9,510,764 | B2 | 12/2016 | Li et al. |
| 9,510,768 | B2 | 12/2016 | Rossi |
| 9,526,433 | B2 | 12/2016 | Lapetina et al. |
| 9,545,204 | B2 | 1/2017 | Bishay et al. |
| 9,545,228 | B2 | 1/2017 | Bardy et al. |
| 9,554,715 | B2 | 1/2017 | Bardy et al. |
| 9,579,020 | B2 | 2/2017 | Libbus et al. |
| D780,914 | S | 3/2017 | Kyvik et al. |
| 9,585,584 | B2 | 3/2017 | Marek et al. |
| 9,597,004 | B2 | 3/2017 | Hughes et al. |
| 9,615,763 | B2 | 4/2017 | Felix et al. |
| 9,615,793 | B2 | 4/2017 | Solosko et al. |
| 9,619,660 | B1 | 4/2017 | Felix et al. |
| 9,642,537 | B2 | 5/2017 | Felix et al. |
| 9,655,518 | B2 | 5/2017 | Lin |
| 9,655,537 | B2 | 5/2017 | Bardy et al. |
| 9,655,538 | B2 | 5/2017 | Felix |
| 9,662,030 | B2 | 5/2017 | Thng et al. |
| 9,675,264 | B2 | 6/2017 | Acquista et al. |
| 9,700,227 | B2 | 7/2017 | Bishay et al. |
| 9,706,938 | B2 | 7/2017 | Chakravarthy et al. |
| 9,706,956 | B2 | 7/2017 | Brockway et al. |

(56) References Cited

U.S. PATENT DOCUMENTS

| | | | |
|---|---|---|---|
| 9,713,428 | B2 | 7/2017 | Chon et al. |
| D793,566 | S | 8/2017 | Bishay et al. |
| D794,812 | S | 8/2017 | Matsushita |
| 9,717,432 | B2 | 8/2017 | Bardy et al. |
| 9,717,433 | B2 | 8/2017 | Felix et al. |
| 9,730,593 | B2 | 8/2017 | Bardy et al. |
| 9,730,604 | B2 | 8/2017 | Li et al. |
| 9,730,641 | B2 | 8/2017 | Felix et al. |
| 9,736,625 | B1 | 8/2017 | Landgraf et al. |
| 9,737,211 | B2 | 8/2017 | Bardy et al. |
| 9,737,224 | B2 | 8/2017 | Bardy et al. |
| D797,301 | S | 9/2017 | Chen |
| D797,943 | S | 9/2017 | Long |
| D798,170 | S | 9/2017 | Toth et al. |
| D798,294 | S | 9/2017 | Toth et al. |
| 9,775,534 | B2 | 10/2017 | Korzinov et al. |
| 9,775,536 | B2 | 10/2017 | Felix et al. |
| 9,782,095 | B2 | 10/2017 | Ylostalo et al. |
| 9,782,132 | B2 | 10/2017 | Golda et al. |
| 9,788,722 | B2 | 10/2017 | Bardy et al. |
| 9,801,562 | B1 | 10/2017 | Host-Madsen |
| 9,820,665 | B2 | 11/2017 | Felix et al. |
| 9,839,363 | B2 | 12/2017 | Albert |
| D810,308 | S | 2/2018 | Lind et al. |
| D811,610 | S | 2/2018 | Abel et al. |
| D811,611 | S | 2/2018 | Lind et al. |
| D811,615 | S | 2/2018 | Lind et al. |
| 9,888,866 | B2 | 2/2018 | Chon et al. |
| 9,901,274 | B2 | 2/2018 | Bishay et al. |
| 9,907,478 | B2 | 3/2018 | Friedman et al. |
| 9,936,875 | B2 | 4/2018 | Bardy et al. |
| 9,955,885 | B2 | 5/2018 | Felix et al. |
| 9,955,887 | B2 | 5/2018 | Hughes et al. |
| 9,955,888 | B2 | 5/2018 | Felix et al. |
| 9,955,911 | B2 | 5/2018 | Bardy et al. |
| 9,968,274 | B2 | 5/2018 | Korzinov et al. |
| 9,986,921 | B2 | 6/2018 | Chon et al. |
| 10,004,415 | B2 | 6/2018 | Bishay et al. |
| D823,466 | S | 7/2018 | Marogil |
| D824,526 | S | 7/2018 | Ramjit et al. |
| 10,045,709 | B2 | 8/2018 | Bardy et al. |
| 10,052,022 | B2 | 8/2018 | Bardy et al. |
| 10,076,257 | B2 | 9/2018 | Lin et al. |
| 10,095,841 | B2 | 10/2018 | Dettinger et al. |
| 10,098,559 | B2 | 10/2018 | Hughes et al. |
| 10,111,601 | B2 | 10/2018 | Bishay et al. |
| 10,123,703 | B2 | 11/2018 | Bardy et al. |
| 10,154,793 | B2 | 12/2018 | Felix et al. |
| 10,159,422 | B2 | 12/2018 | Baker et al. |
| 10,165,946 | B2 | 1/2019 | Bardy et al. |
| 10,172,534 | B2 | 1/2019 | Felix et al. |
| 10,176,575 | B2 | 1/2019 | Isgum et al. |
| 10,244,949 | B2 | 4/2019 | Moyer et al. |
| 10,251,575 | B2 | 4/2019 | Bardy et al. |
| 10,251,576 | B2 | 4/2019 | Bardy et al. |
| 10,264,992 | B2 | 4/2019 | Felix et al. |
| 10,265,015 | B2 | 4/2019 | Bardy et al. |
| 10,270,898 | B2 | 4/2019 | Soli et al. |
| 10,271,754 | B2 | 4/2019 | Bahney et al. |
| 10,271,755 | B2 | 4/2019 | Felix et al. |
| 10,271,756 | B2 | 4/2019 | Felix et al. |
| 10,278,603 | B2 | 5/2019 | Felix et al. |
| 10,278,606 | B2 | 5/2019 | Bishay et al. |
| 10,278,607 | B2 | 5/2019 | Prystowsky et al. |
| 10,299,691 | B2 | 5/2019 | Hughes et al. |
| 10,321,823 | B2 | 6/2019 | Chakravarthy et al. |
| 10,327,657 | B2 | 6/2019 | Spencer et al. |
| 10,327,660 | B2 | 6/2019 | Gallego et al. |
| D852,965 | S | 7/2019 | Bahney et al. |
| D854,167 | S | 7/2019 | Bahney et al. |
| 10,362,467 | B2 | 7/2019 | Landgraf et al. |
| 10,368,808 | B2 | 8/2019 | Lee et al. |
| 10,376,172 | B2 | 8/2019 | Kuppuraj et al. |
| 10,390,700 | B2 | 8/2019 | Bardy et al. |
| 10,398,344 | B2 | 9/2019 | Felix et al. |
| 10,405,799 | B2 | 9/2019 | Kumar et al. |
| 10,413,205 | B2 | 9/2019 | Bardy et al. |
| 10,426,634 | B1 | 10/2019 | Al-Jazaeri et al. |
| 10,433,743 | B1 | 10/2019 | Felix et al. |
| 10,433,748 | B2 | 10/2019 | Bishay et al. |
| 10,433,751 | B2 | 10/2019 | Bardy et al. |
| 10,441,184 | B2 | 10/2019 | Baumann et al. |
| 10,463,269 | B2 | 11/2019 | Boleyn et al. |
| 10,478,083 | B2 | 11/2019 | Felix et al. |
| 10,499,812 | B2 | 12/2019 | Bardy et al. |
| 10,517,500 | B2 | 12/2019 | Kumar et al. |
| 10,555,683 | B2 | 2/2020 | Bahney et al. |
| 10,561,326 | B2 | 2/2020 | Felix et al. |
| 10,561,328 | B2 | 2/2020 | Bishay |
| 10,568,533 | B2 | 2/2020 | Soli et al. |
| 10,588,527 | B2 | 3/2020 | McNamara et al. |
| 10,595,371 | B2 | 3/2020 | Gopalakrishnan et al. |
| 10,602,942 | B2 | 3/2020 | Shakur et al. |
| 10,602,977 | B2 | 3/2020 | Bardy et al. |
| 10,624,551 | B2 | 4/2020 | Bardy et al. |
| 10,660,520 | B2 | 5/2020 | Lin |
| 10,667,712 | B2 | 6/2020 | Park et al. |
| 10,729,361 | B2 | 8/2020 | Hoppe et al. |
| 10,758,139 | B2 | 9/2020 | Rapin et al. |
| 10,772,521 | B2 | 9/2020 | Korzinov et al. |
| 10,779,744 | B2 | 9/2020 | Rapin et al. |
| 10,813,565 | B2 | 10/2020 | Park et al. |
| 10,827,938 | B2 | 11/2020 | Fontanarava et al. |
| 10,866,619 | B1 | 12/2020 | Bushnell et al. |
| 10,869,610 | B2 | 12/2020 | Lu et al. |
| 10,987,018 | B2 | 4/2021 | Aga et al. |
| 11,004,198 | B2 | 5/2021 | Isgum et al. |
| 11,017,887 | B2 | 5/2021 | Finkelmeier et al. |
| 11,026,632 | B2 | 6/2021 | Narasimhan et al. |
| 11,051,738 | B2 | 7/2021 | Bahney et al. |
| 11,051,743 | B2 | 7/2021 | Felix et al. |
| 11,062,804 | B2 | 7/2021 | Selvaraj et al. |
| 11,083,371 | B1 | 8/2021 | Szabados et al. |
| 11,116,447 | B2 | 9/2021 | Yang et al. |
| 11,141,091 | B2 | 10/2021 | Uday et al. |
| 11,172,882 | B2 | 11/2021 | Upadhya et al. |
| 11,246,523 | B1 | 2/2022 | Abercrombie, II et al. |
| 11,246,524 | B2 | 2/2022 | Szabados et al. |
| 11,253,185 | B2 | 2/2022 | Szabados et al. |
| 11,253,186 | B2 | 2/2022 | Szabados et al. |
| 11,276,491 | B2 | 3/2022 | Petterson et al. |
| 11,289,197 | B1 | 3/2022 | Park et al. |
| 11,324,420 | B2 | 5/2022 | Selvaraj et al. |
| 11,324,441 | B2 | 5/2022 | Bardy et al. |
| 11,331,034 | B2 | 5/2022 | Rapin et al. |
| 11,337,632 | B2 | 5/2022 | Abercrombie, II et al. |
| 11,350,864 | B2 | 6/2022 | Abercrombie, II et al. |
| 11,350,865 | B2 | 6/2022 | Abercrombie, II et al. |
| 11,367,514 | B2 | 6/2022 | McNamara et al. |
| 11,375,941 | B2 | 7/2022 | Szabados et al. |
| 11,382,555 | B2 | 7/2022 | Szabados et al. |
| 11,399,760 | B2 | 8/2022 | Abercrombie, II et al. |
| 11,445,967 | B2 | 9/2022 | Felix et al. |
| 11,497,432 | B2 | 11/2022 | Szabados et al. |
| 11,504,041 | B2 | 11/2022 | Abercrombie, II et al. |
| 11,589,792 | B1 | 2/2023 | Abercrombie, II et al. |
| 11,605,458 | B2 | 3/2023 | Park et al. |
| 11,627,902 | B2 | 4/2023 | Bahney et al. |
| 11,660,037 | B2 | 5/2023 | Felix et al. |
| D988,518 | S | 6/2023 | Levy et al. |
| 11,678,832 | B2 | 6/2023 | Boleyn et al. |
| 11,751,789 | B2 | 9/2023 | Abercrombie, II et al. |
| 11,756,684 | B2 | 9/2023 | Park et al. |
| 11,806,150 | B2 | 11/2023 | Abercrombie, II et al. |
| D1,012,295 | S | 1/2024 | Peremen et al. |
| 11,925,469 | B2 | 3/2024 | Szabados et al. |
| 11,998,342 | B2 | 6/2024 | Szabados et al. |
| 12,133,731 | B2 | 11/2024 | Abercrombie, II et al. |
| 12,133,734 | B2 | 11/2024 | Kumar et al. |
| 12,213,791 | B2 | 2/2025 | Abercrombie, II et al. |
| 12,245,859 | B2 | 3/2025 | Bahney et al. |
| 12,245,860 | B2 | 3/2025 | Bahney et al. |
| 12,274,554 | B2 | 4/2025 | Kumar et al. |
| 12,285,261 | B2 | 4/2025 | Bishay et al. |

(56) References Cited

U.S. PATENT DOCUMENTS

| | | | |
|---|---|---|---|
| 12,303,275 | B2 | 5/2025 | Bahney et al. |
| 12,303,277 | B2 | 5/2025 | Kumar et al. |
| 12,310,735 | B2 | 5/2025 | Felix et al. |
| 12,324,668 | B2 | 6/2025 | Kumar et al. |
| 12,357,212 | B2 | 7/2025 | Bahney et al. |
| 12,402,819 | B1 | 9/2025 | Bahney et al. |
| 12,408,856 | B1 | 9/2025 | Kumar et al. |
| 12,582,339 | B2 | 3/2026 | Abercrombie, II et al. |
| 12,603,173 | B2 | 4/2026 | Park et al. |
| 2001/0056262 | A1 | 12/2001 | Cabiri et al. |
| 2002/0007126 | A1 | 1/2002 | Nissila |
| 2002/0026112 | A1 | 2/2002 | Nissila et al. |
| 2002/0067256 | A1 | 6/2002 | Kail |
| 2002/0082491 | A1 | 6/2002 | Nissila |
| 2002/0087167 | A1 | 7/2002 | Winitsky |
| 2002/0099277 | A1 | 7/2002 | Harry et al. |
| 2002/0106709 | A1 | 8/2002 | Potts et al. |
| 2002/0180605 | A1 | 12/2002 | Ozguz et al. |
| 2003/0023178 | A1 | 1/2003 | Bischoff et al. |
| 2003/0055460 | A1 | 3/2003 | Owen et al. |
| 2003/0069510 | A1 | 4/2003 | Semler |
| 2003/0083559 | A1 | 5/2003 | Thompson |
| 2003/0125786 | A1 | 7/2003 | Gliner |
| 2003/0149349 | A1 | 8/2003 | Jensen |
| 2003/0149439 | A1 | 8/2003 | Wendlandt |
| 2003/0176795 | A1 | 9/2003 | Harris et al. |
| 2003/0195408 | A1 | 10/2003 | Hastings |
| 2003/0199811 | A1 | 10/2003 | Sage, Jr. et al. |
| 2003/0212319 | A1 | 11/2003 | Magill |
| 2003/0216662 | A1 | 11/2003 | Jersey-Willuhn et al. |
| 2004/0032957 | A1 | 2/2004 | Mansy et al. |
| 2004/0068195 | A1 | 4/2004 | Massicotte et al. |
| 2004/0077954 | A1 | 4/2004 | Oakley et al. |
| 2004/0082843 | A1 | 4/2004 | Menon |
| 2004/0171921 | A1 | 9/2004 | Say et al. |
| 2004/0187297 | A1 | 9/2004 | Su |
| 2004/0199063 | A1 | 10/2004 | O'Neil |
| 2004/0215091 | A1 | 10/2004 | Lohman et al. |
| 2004/0236202 | A1 | 11/2004 | Burton |
| 2004/0238819 | A1 | 12/2004 | Maghribi et al. |
| 2004/0254587 | A1 | 12/2004 | Park |
| 2004/0260189 | A1 | 12/2004 | Eggers et al. |
| 2005/0096513 | A1 | 5/2005 | Ozguz et al. |
| 2005/0101875 | A1 | 5/2005 | Semler et al. |
| 2005/0118246 | A1 | 6/2005 | Wong et al. |
| 2005/0119580 | A1 | 6/2005 | Eveland |
| 2005/0165318 | A1 | 7/2005 | Brodnick et al. |
| 2005/0165323 | A1 | 7/2005 | Montgomery et al. |
| 2005/0204636 | A1 | 9/2005 | Azar et al. |
| 2005/0245797 | A1 | 11/2005 | Al-Ali et al. |
| 2005/0245839 | A1 | 11/2005 | Stivoric et al. |
| 2005/0277841 | A1 | 12/2005 | Shennib |
| 2005/0280531 | A1 | 12/2005 | Fadem et al. |
| 2006/0030781 | A1 | 2/2006 | Shennib |
| 2006/0030782 | A1 | 2/2006 | Shennib |
| 2006/0047215 | A1 | 3/2006 | Newman et al. |
| 2006/0052999 | A1 | 3/2006 | Brooks et al. |
| 2006/0084883 | A1 | 4/2006 | Linker |
| 2006/0142648 | A1 | 6/2006 | Banet et al. |
| 2006/0142654 | A1 | 6/2006 | Rytky |
| 2006/0149156 | A1 | 7/2006 | Cochran et al. |
| 2006/0155173 | A1 | 7/2006 | Anttila et al. |
| 2006/0155183 | A1 | 7/2006 | Kroecker et al. |
| 2006/0155199 | A1 | 7/2006 | Logier et al. |
| 2006/0155200 | A1 | 7/2006 | Ng et al. |
| 2006/0161064 | A1 | 7/2006 | Watrous et al. |
| 2006/0161065 | A1 | 7/2006 | Elion |
| 2006/0161066 | A1 | 7/2006 | Elion |
| 2006/0161067 | A1 | 7/2006 | Elion |
| 2006/0161068 | A1 | 7/2006 | Hastings et al. |
| 2006/0167353 | A1 | 7/2006 | Nazeri |
| 2006/0224072 | A1 | 10/2006 | Shennib |
| 2006/0238333 | A1 | 10/2006 | Welch et al. |
| 2006/0247509 | A1 | 11/2006 | Tuccillo et al. |
| 2006/0264767 | A1 | 11/2006 | Shennib |
| 2007/0003695 | A1 | 1/2007 | Tregub et al. |
| 2007/0010729 | A1 | 1/2007 | Virtanen |
| 2007/0027388 | A1 | 2/2007 | Chou |
| 2007/0069887 | A1 | 3/2007 | Welch et al. |
| 2007/0073132 | A1 | 3/2007 | Vosch |
| 2007/0088419 | A1 | 4/2007 | Florina et al. |
| 2007/0156054 | A1 | 7/2007 | Korzinov et al. |
| 2007/0208266 | A1 | 9/2007 | Hadley |
| 2007/0225611 | A1 | 9/2007 | Kumar et al. |
| 2007/0249946 | A1 | 10/2007 | Kumar et al. |
| 2007/0255153 | A1 | 11/2007 | Kumar et al. |
| 2007/0270678 | A1 | 11/2007 | Fadem et al. |
| 2007/0285868 | A1 | 12/2007 | Lindberg et al. |
| 2007/0293776 | A1 | 12/2007 | Korzinov et al. |
| 2007/0299325 | A1 | 12/2007 | Farrell |
| 2008/0039730 | A1 | 2/2008 | Pu et al. |
| 2008/0091089 | A1 | 4/2008 | Guillory et al. |
| 2008/0108890 | A1 | 5/2008 | Teng et al. |
| 2008/0114232 | A1 | 5/2008 | Gazit |
| 2008/0139953 | A1 | 6/2008 | Baker et al. |
| 2008/0167567 | A1 | 7/2008 | Bashour et al. |
| 2008/0171918 | A1 | 7/2008 | Teller et al. |
| 2008/0182204 | A1 | 7/2008 | Calvert et al. |
| 2008/0214901 | A1 | 9/2008 | Gehman et al. |
| 2008/0275327 | A1 | 11/2008 | Faarbaek et al. |
| 2008/0281215 | A1 | 11/2008 | Alhussiny |
| 2008/0288026 | A1 | 11/2008 | Cross et al. |
| 2008/0306397 | A1 | 12/2008 | Bonmassar et al. |
| 2008/0309287 | A1 | 12/2008 | Reed |
| 2008/0312524 | A1 | 12/2008 | Solosko et al. |
| 2009/0048556 | A1 | 2/2009 | Durand |
| 2009/0048563 | A1 | 2/2009 | Ethelfeld et al. |
| 2009/0062670 | A1 | 3/2009 | Sterling et al. |
| 2009/0062671 | A1 | 3/2009 | Brockway |
| 2009/0073991 | A1 | 3/2009 | Landrum et al. |
| 2009/0076336 | A1 | 3/2009 | Mazar et al. |
| 2009/0076340 | A1 | 3/2009 | Libbus et al. |
| 2009/0076341 | A1 | 3/2009 | James et al. |
| 2009/0076342 | A1 | 3/2009 | Amurthur et al. |
| 2009/0076343 | A1 | 3/2009 | James et al. |
| 2009/0076344 | A1 | 3/2009 | Libbus et al. |
| 2009/0076345 | A1 | 3/2009 | Manicka et al. |
| 2009/0076346 | A1 | 3/2009 | James et al. |
| 2009/0076349 | A1 | 3/2009 | Libbus et al. |
| 2009/0076350 | A1 | 3/2009 | Bly et al. |
| 2009/0076363 | A1 | 3/2009 | Bly et al. |
| 2009/0076364 | A1 | 3/2009 | Libbus et al. |
| 2009/0076397 | A1 | 3/2009 | Libbus et al. |
| 2009/0076401 | A1 | 3/2009 | Mazar et al. |
| 2009/0076559 | A1 | 3/2009 | Libbus et al. |
| 2009/0131759 | A1 | 5/2009 | Sims et al. |
| 2009/0182204 | A1 | 7/2009 | Semler et al. |
| 2009/0253975 | A1 | 10/2009 | Tiegs |
| 2009/0283300 | A1 | 11/2009 | Grunthaner |
| 2009/0292193 | A1 | 11/2009 | Wijesiriwardana |
| 2009/0292194 | A1 | 11/2009 | Libbus et al. |
| 2009/0306485 | A1 | 12/2009 | Bell |
| 2010/0001541 | A1 | 1/2010 | Sugiyama |
| 2010/0016701 | A1 | 1/2010 | Cheng et al. |
| 2010/0022864 | A1 | 1/2010 | Cordero |
| 2010/0042113 | A1 | 2/2010 | Mah |
| 2010/0049006 | A1 | 2/2010 | Magar et al. |
| 2010/0051039 | A1 | 3/2010 | Ferrara |
| 2010/0056881 | A1 | 3/2010 | Libbus et al. |
| 2010/0057056 | A1 | 3/2010 | Gurtner |
| 2010/0076533 | A1 | 3/2010 | Dar et al. |
| 2010/0081913 | A1 | 4/2010 | Cross et al. |
| 2010/0145359 | A1 | 6/2010 | Keller |
| 2010/0191310 | A1 | 7/2010 | Bly |
| 2010/0234716 | A1 | 9/2010 | Engel |
| 2010/0249625 | A1 | 9/2010 | Lin |
| 2010/0268103 | A1 | 10/2010 | McNamara et al. |
| 2010/0312131 | A1 | 12/2010 | Naware et al. |
| 2010/0331711 | A1 | 12/2010 | Krauss et al. |
| 2011/0009729 | A1 | 1/2011 | Shin et al. |
| 2011/0021937 | A1 | 1/2011 | Hugh et al. |
| 2011/0077497 | A1 | 3/2011 | Oster et al. |
| 2011/0087083 | A1 | 4/2011 | Poeze et al. |
| 2011/0098583 | A1 | 4/2011 | Pandia et al. |

(56) References Cited

U.S. PATENT DOCUMENTS

2011/0119212 A1 5/2011 De Bruin et al.
2011/0144470 A1 6/2011 Mazar et al.
2011/0160601 A1 6/2011 Wang et al.
2011/0166468 A1 7/2011 Prystowsky et al.
2011/0190650 A1 8/2011 McNair
2011/0218415 A1 9/2011 Chen
2011/0237922 A1 9/2011 Parker, III et al.
2011/0237924 A1 9/2011 McGusty et al.
2011/0251504 A1 10/2011 Tereshchenko et al.
2011/0270049 A1 11/2011 Katra et al.
2011/0306862 A1 12/2011 Hayes-Gill
2012/0023306 A1 1/2012 Chase
2012/0029306 A1 2/2012 Paquet et al.
2012/0029307 A1 2/2012 Paquet et al.
2012/0071730 A1 3/2012 Romero
2012/0071731 A1 3/2012 Gottesman
2012/0071743 A1 3/2012 Todorov et al.
2012/0083670 A1 4/2012 Rotondo et al.
2012/0088998 A1 4/2012 Bardy et al.
2012/0088999 A1 4/2012 Bishay et al.
2012/0089001 A1 4/2012 Bishay et al.
2012/0089037 A1 4/2012 Bishay et al.
2012/0089039 A1 4/2012 Felix et al.
2012/0101396 A1 4/2012 Solosko et al.
2012/0108917 A1 5/2012 Libbus et al.
2012/0108920 A1 5/2012 Bly et al.
2012/0110226 A1 5/2012 Vlach et al.
2012/0110228 A1 5/2012 Vlach et al.
2012/0123232 A1 5/2012 Najarian et al.
2012/0133162 A1 5/2012 Sgobero
2012/0172676 A1 7/2012 Penders et al.
2012/0173470 A1 7/2012 Bashour et al.
2012/0197150 A1 8/2012 Cao et al.
2012/0209102 A1 8/2012 Ylotalo et al.
2012/0209126 A1 8/2012 Amos et al.
2012/0215123 A1 8/2012 Kumar et al.
2012/0220835 A1 8/2012 Chung
2012/0259233 A1 10/2012 Chan et al.
2012/0271141 A1 10/2012 Davies
2012/0310070 A1 12/2012 Kumar et al.
2012/0316532 A1 12/2012 McCormick
2012/0323257 A1 12/2012 Sutton
2012/0330126 A1 12/2012 Hoppe et al.
2013/0023816 A1 1/2013 Bachinski et al.
2013/0041273 A1 2/2013 Houben et al.
2013/0046151 A1 2/2013 Bsoul et al.
2013/0085347 A1 4/2013 Manicka et al.
2013/0085538 A1 4/2013 Volpe et al.
2013/0096395 A1 4/2013 Katra et al.
2013/0116533 A1 5/2013 Lian et al.
2013/0116585 A1 5/2013 Bouguerra
2013/0144146 A1 6/2013 Linker
2013/0150698 A1 6/2013 Hsu et al.
2013/0158494 A1 6/2013 Ong
2013/0172763 A1 7/2013 Wheeler
2013/0184662 A1 7/2013 Aali et al.
2013/0191035 A1 7/2013 Chon et al.
2013/0225938 A1 8/2013 Vlach
2013/0225967 A1 8/2013 Esposito
2013/0226018 A1 8/2013 Kumar et al.
2013/0245415 A1 9/2013 Kumar et al.
2013/0245472 A1 9/2013 Eveland
2013/0253285 A1 9/2013 Bly et al.
2013/0274584 A1 10/2013 Finlay et al.
2013/0289424 A1 10/2013 Brockway et al.
2013/0296680 A1 11/2013 Linker
2013/0300575 A1 11/2013 Kurzweil et al.
2013/0324868 A1 12/2013 Kaib et al.
2013/0331663 A1 12/2013 Albert et al.
2013/0331665 A1 12/2013 Bly et al.
2013/0338448 A1 12/2013 Libbus et al.
2014/0012154 A1 1/2014 Mazar
2014/0058280 A1 2/2014 Chefles et al.
2014/0088394 A1 3/2014 Sunderland
2014/0094676 A1 4/2014 Gani et al.
2014/0094709 A1 4/2014 Korzinov et al.
2014/0100432 A1 4/2014 Golda et al.
2014/0116825 A1 5/2014 Lindeman
2014/0142411 A1 5/2014 Lin et al.
2014/0148714 A1 5/2014 Mamaghanian et al.
2014/0171751 A1 6/2014 Sankman et al.
2014/0206976 A1 7/2014 Thompson et al.
2014/0206977 A1 7/2014 Bahney et al.
2014/0243621 A1 8/2014 Weng et al.
2014/0275827 A1 9/2014 Gill et al.
2014/0275840 A1 9/2014 Osorio
2014/0275928 A1 9/2014 Acquista et al.
2014/0303647 A1 10/2014 Sepulveda et al.
2014/0330136 A1 11/2014 Manicka et al.
2015/0005854 A1 1/2015 Said
2015/0022372 A1 1/2015 Vosch
2015/0057512 A1 2/2015 Kapoor
2015/0073252 A1 3/2015 Mazar
2015/0081959 A1 3/2015 Vlach et al.
2015/0082623 A1 3/2015 Felix et al.
2015/0087921 A1 3/2015 Felix et al.
2015/0087922 A1 3/2015 Bardy et al.
2015/0087923 A1 3/2015 Bardy et al.
2015/0087933 A1 3/2015 Gibson et al.
2015/0087948 A1 3/2015 Bishay et al.
2015/0087949 A1 3/2015 Felix et al.
2015/0087950 A1 3/2015 Felix et al.
2015/0087951 A1 3/2015 Felix et al.
2015/0088007 A1 3/2015 Bardy et al.
2015/0088020 A1 3/2015 Dreisbach et al.
2015/0094556 A1 4/2015 Geva et al.
2015/0148637 A1 5/2015 Golda et al.
2015/0157273 A1 6/2015 An et al.
2015/0173671 A1 6/2015 Paalasmaa et al.
2015/0193595 A1 7/2015 McNamara et al.
2015/0196770 A1 7/2015 Cappelaere et al.
2015/0223711 A1 8/2015 Raeder et al.
2015/0238107 A1 8/2015 Acquista et al.
2015/0289814 A1 10/2015 Magar et al.
2015/0297134 A1 10/2015 Albert et al.
2015/0327781 A1 11/2015 Hernandez-Silverira et al.
2015/0351689 A1 12/2015 Adams
2015/0351799 A1 12/2015 Sepulveda et al.
2015/0374244 A1 12/2015 Yoo et al.
2016/0022161 A1 1/2016 Khair
2016/0029906 A1 2/2016 Tompkins et al.
2016/0066808 A1 3/2016 Hijazi
2016/0085927 A1 3/2016 Dettinger et al.
2016/0085937 A1 3/2016 Dettinger et al.
2016/0086297 A1 3/2016 Dettinger et al.
2016/0098536 A1 4/2016 Dettinger et al.
2016/0098537 A1 4/2016 Dettinger et al.
2016/0113520 A1 4/2016 Manera
2016/0120433 A1 5/2016 Hughes et al.
2016/0120434 A1 5/2016 Park et al.
2016/0128597 A1 5/2016 Lin et al.
2016/0135746 A1 5/2016 Kumar et al.
2016/0149292 A1 5/2016 Ganton
2016/0157744 A1 6/2016 Wu et al.
2016/0166155 A1 6/2016 Banet et al.
2016/0192852 A1 7/2016 Bozza et al.
2016/0192855 A1 7/2016 Geva et al.
2016/0192856 A1 7/2016 Lee
2016/0198972 A1 7/2016 Lee et al.
2016/0232807 A1 8/2016 Ghaffari et al.
2016/0262619 A1 9/2016 Marcus et al.
2016/0278658 A1 9/2016 Bardy et al.
2016/0287177 A1 10/2016 Huppert et al.
2016/0287207 A1 10/2016 Xue
2016/0296132 A1 10/2016 Bojovic et al.
2016/0302725 A1 10/2016 Schultz et al.
2016/0302726 A1 10/2016 Chang
2016/0317048 A1 11/2016 Chan et al.
2016/0317057 A1 11/2016 Li et al.
2016/0359150 A1 12/2016 De Francisco Martin et al.
2016/0361015 A1 12/2016 Wang et al.
2016/0367164 A1 12/2016 Felix et al.
2016/0374583 A1 12/2016 Cerruti et al.
2017/0042447 A1 2/2017 Rossi

(56) References Cited

U.S. PATENT DOCUMENTS

| | | | |
|---|---|---|---|
| 2017/0055896 | A1 | 3/2017 | Al-Ali et al. |
| 2017/0056682 | A1 | 3/2017 | Kumar |
| 2017/0065823 | A1 | 3/2017 | Kaib et al. |
| 2017/0076641 | A1 | 3/2017 | Senanayake |
| 2017/0188872 | A1 | 7/2017 | Hughes et al. |
| 2017/0188971 | A1 | 7/2017 | Hughes et al. |
| 2017/0354335 | A1 | 12/2017 | Bower et al. |
| 2018/0049698 | A1 | 2/2018 | Berg |
| 2018/0049716 | A1 | 2/2018 | Rajagopal et al. |
| 2018/0064388 | A1 | 3/2018 | Heneghan et al. |
| 2018/0107798 | A1 | 4/2018 | Hu |
| 2018/0110266 | A1 | 4/2018 | Lee et al. |
| 2018/0125387 | A1 | 5/2018 | Hadley et al. |
| 2018/0144241 | A1 | 5/2018 | Liu et al. |
| 2018/0146875 | A1 | 5/2018 | Friedman et al. |
| 2018/0161211 | A1 | 6/2018 | Beckey |
| 2018/0242876 | A1 | 8/2018 | Hughes et al. |
| 2018/0257346 | A1 | 9/2018 | Austin |
| 2018/0260706 | A1 | 9/2018 | Galloway et al. |
| 2018/0289274 | A1 | 10/2018 | Bahney et al. |
| 2018/0374576 | A1 | 12/2018 | Dettinger et al. |
| 2019/0015008 | A1 | 1/2019 | Alizadeh et al. |
| 2019/0021671 | A1 | 1/2019 | Kumar et al. |
| 2019/0038148 | A1 | 2/2019 | Valys |
| 2019/0046066 | A1 | 2/2019 | Hughes et al. |
| 2019/0069788 | A1 | 3/2019 | Coleman et al. |
| 2019/0090769 | A1 | 3/2019 | Boleyn et al. |
| 2019/0097339 | A1 | 3/2019 | Lim et al. |
| 2019/0098758 | A1 | 3/2019 | Hassemer et al. |
| 2019/0099132 | A1 | 4/2019 | Mulinti et al. |
| 2019/0125260 | A1 | 5/2019 | Levesque et al. |
| 2019/0133468 | A1 | 5/2019 | Aliamiri et al. |
| 2019/0167143 | A1 | 6/2019 | Li et al. |
| 2019/0209022 | A1 | 7/2019 | Sobol |
| 2019/0246928 | A1 | 8/2019 | Bahney et al. |
| 2019/0274574 | A1 | 9/2019 | Hughes et al. |
| 2019/0282178 | A1 | 9/2019 | Volosin et al. |
| 2019/0283204 | A1 | 9/2019 | Swedek et al. |
| 2019/0290147 | A1 | 9/2019 | Persen et al. |
| 2019/0298201 | A1 | 10/2019 | Persen et al. |
| 2019/0298209 | A1 | 10/2019 | Persen et al. |
| 2019/0298272 | A1 | 10/2019 | Persen |
| 2019/0320930 | A1 | 10/2019 | Derkx |
| 2019/0328264 | A1 | 10/2019 | Jeong |
| 2019/0370636 | A1 | 12/2019 | Isopoussu |
| 2019/0374163 | A1 | 12/2019 | Faabaek et al. |
| 2019/0378617 | A1 | 12/2019 | Charles et al. |
| 2020/0060563 | A1 | 2/2020 | Boleyn |
| 2020/0093388 | A1 | 3/2020 | Bouguerra et al. |
| 2020/0100693 | A1 | 4/2020 | Velo |
| 2020/0101278 | A1 | 4/2020 | Freeman et al. |
| 2020/0108260 | A1 | 4/2020 | Haddad et al. |
| 2020/0121209 | A1 | 4/2020 | Kumar et al. |
| 2020/0170529 | A1 | 6/2020 | Bahney et al. |
| 2020/0178825 | A1 | 6/2020 | Lu |
| 2020/0178828 | A1 | 6/2020 | Bahney et al. |
| 2020/0193597 | A1 | 6/2020 | Fan et al. |
| 2020/0196897 | A1 | 6/2020 | Biswas et al. |
| 2020/0214563 | A1 | 7/2020 | Lin |
| 2020/0214584 | A1 | 7/2020 | McNamara et al. |
| 2020/0237309 | A1 | 7/2020 | Golda et al. |
| 2020/0289014 | A1 | 9/2020 | Park et al. |
| 2020/0297230 | A1 | 9/2020 | Thakur et al. |
| 2020/0337608 | A1 | 10/2020 | Garai et al. |
| 2020/0352489 | A1 | 11/2020 | Hoppe et al. |
| 2020/0367779 | A1 | 11/2020 | Korzinov et al. |
| 2020/0397313 | A1 | 12/2020 | Attia et al. |
| 2021/0038102 | A1 | 2/2021 | Boleyn et al. |
| 2021/0059612 | A1 | 3/2021 | Krebs et al. |
| 2021/0076960 | A1 | 3/2021 | Fornwalt et al. |
| 2021/0085215 | A1 | 3/2021 | Auerbach et al. |
| 2021/0085255 | A1 | 3/2021 | Vule et al. |
| 2021/0125722 | A1 | 4/2021 | Sherkat et al. |
| 2021/0153761 | A1 | 5/2021 | Jung et al. |
| 2021/0217519 | A1 | 7/2021 | Park et al. |
| 2021/0244279 | A1 | 8/2021 | Szabados et al. |
| 2021/0269046 | A1 | 9/2021 | Hashimoto et al. |
| 2021/0298688 | A1 | 9/2021 | Banerjee et al. |
| 2021/0304855 | A1 | 9/2021 | Ansari et al. |
| 2021/0315470 | A1 | 10/2021 | Wu et al. |
| 2021/0315504 | A1 | 10/2021 | Kumar et al. |
| 2021/0361218 | A1 | 11/2021 | Szabados et al. |
| 2021/0369178 | A1 | 12/2021 | Szabados et al. |
| 2021/0374502 | A1 | 12/2021 | Roth et al. |
| 2021/0378579 | A1 | 12/2021 | Doron et al. |
| 2021/0393187 | A1 | 12/2021 | Amos et al. |
| 2022/0022798 | A1 | 1/2022 | Soon-Shiong et al. |
| 2022/0031223 | A1 | 2/2022 | Li et al. |
| 2022/0039719 | A1 | 2/2022 | Abercrombie et al. |
| 2022/0039720 | A1 | 2/2022 | Abercrombie et al. |
| 2022/0079497 | A1 | 3/2022 | Bardy et al. |
| 2022/0084669 | A1 | 3/2022 | Van Berkel et al. |
| 2022/0084680 | A1 | 3/2022 | Schmid et al. |
| 2022/0093247 | A1 | 3/2022 | Park et al. |
| 2022/0095982 | A1 | 3/2022 | De Saint Victor et al. |
| 2022/0142493 | A1 | 5/2022 | Albert |
| 2022/0142495 | A1 | 5/2022 | De Marco et al. |
| 2022/0296144 | A1 | 9/2022 | Abercrombie, II et al. |
| 2022/0361793 | A1 | 11/2022 | Abercrombie, II et al. |
| 2023/0036193 | A1 | 2/2023 | Li et al. |
| 2023/0056777 | A1 | 2/2023 | Abercrombie, II et al. |
| 2023/0172511 | A1 | 6/2023 | Abercrombie, II et al. |
| 2023/0172518 | A1 | 6/2023 | Szabados et al. |
| 2023/0248288 | A1 | 8/2023 | Bahney et al. |
| 2023/0371873 | A1 | 11/2023 | Abercrombie, II et al. |
| 2023/0371874 | A1 | 11/2023 | Abercrombie, II et al. |
| 2024/0145080 | A1 | 5/2024 | Park et al. |
| 2024/0321455 | A1 | 9/2024 | Hytopoulos et al. |
| 2024/0331875 | A1 | 10/2024 | Hytopoulos et al. |
| 2024/0358310 | A1 | 10/2024 | Szabados et al. |
| 2024/0382130 | A1 | 11/2024 | Bahney et al. |
| 2024/0382131 | A1 | 11/2024 | Bahney et al. |
| 2024/0398309 | A1 | 12/2024 | Kumar et al. |
| 2024/0398310 | A1 | 12/2024 | Kumar et al. |
| 2025/0009271 | A1 | 1/2025 | Bahney et al. |
| 2025/0057459 | A1 | 2/2025 | Kumar et al. |
| 2025/0241578 | A1 | 7/2025 | Abercrombie et al. |
| 2026/0026726 | A1 | 1/2026 | Kumar et al. |
| 2026/0174345 | A1 | 6/2026 | Lin |

FOREIGN PATENT DOCUMENTS

| | | |
|---|---|---|
| AU | 2021218704 | 2/2024 |
| AU | 2021320404 | 7/2025 |
| AU | 202351520 | 9/2025 |
| CA | 2 535 502 | 3/2005 |
| CA | 2 752 154 | 8/2010 |
| CA | 2 898 626 | 7/2014 |
| CA | 2 797 980 | 8/2015 |
| CA | 2 651 203 | 9/2017 |
| CA | 2 966 182 | 6/2020 |
| CA | 3 171 482 | 3/2024 |
| CN | 102038497 | 7/2012 |
| CN | 102917638 | 2/2013 |
| CN | 102883775 | 12/2014 |
| CN | 103997955 | 11/2016 |
| CN | 303936805 | 11/2016 |
| CN | 106456984 | 2/2017 |
| CN | 107072603 | 8/2017 |
| CN | 107205504 | 9/2017 |
| CN | 107205679 | 9/2017 |
| CN | 107708991 | 2/2018 |
| CN | 108113647 | 6/2018 |
| CN | 108135929 | 6/2018 |
| CN | 109363659 | 2/2019 |
| CN | 110491500 | 11/2019 |
| CN | 110766691 | 2/2020 |
| CN | 110890155 | 3/2020 |
| CN | 110974217 | 4/2020 |
| CN | 111031926 | 4/2020 |
| CN | 111067509 | 4/2020 |
| CN | 115426940 | 12/2022 |
| CN | 116322498 | 6/2023 |
| CN | 116530951 | 8/2023 |

(56) References Cited

FOREIGN PATENT DOCUMENTS

| | | | |
|---|---|---|---|
| CN | 120152655 | | 6/2025 |
| EM | 001857966-0001 | | 5/2011 |
| EM | 002592907-0001 | | 12/2014 |
| EM | 003611714-0001 | | 1/2017 |
| EM | 003611714-0002 | | 1/2017 |
| EM | 003611714-0003 | | 1/2017 |
| EM | 003611714-0004 | | 1/2017 |
| EM | 003611714-0005 | | 1/2017 |
| EP | 0509689 | | 4/1992 |
| EP | 1738686 | | 6/2006 |
| EP | 1782729 | | 5/2007 |
| EP | 1981402 | | 10/2008 |
| EP | 1962686 | | 11/2009 |
| EP | 2262419 | | 12/2010 |
| EP | 2395911 | | 12/2011 |
| EP | 2568878 | | 3/2013 |
| EP | 2635179 | | 9/2013 |
| EP | 2635180 | | 9/2013 |
| EP | 2635938 | | 9/2013 |
| EP | 2948050 | | 12/2015 |
| EP | 2983593 | | 2/2016 |
| EP | 3165161 | | 5/2017 |
| EP | 3212061 | | 9/2017 |
| EP | 3753483 | | 12/2020 |
| EP | 3387991 | | 6/2022 |
| EP | 4103051 | | 12/2022 |
| GB | 2 299 038 | | 9/1996 |
| GB | 2 348 707 | | 10/2000 |
| IN | 002592907-0001 | | 12/2014 |
| JP | S58-152770 | U | 10/1983 |
| JP | S61-137539 | | 6/1986 |
| JP | H05-329123 | | 12/1993 |
| JP | H08-317913 | | 3/1996 |
| JP | H08-322952 | | 12/1996 |
| JP | H09-108195 | | 4/1997 |
| JP | H10-179531 | | 7/1998 |
| JP | 2000-037413 | | 2/2000 |
| JP | 2000-126145 | | 5/2000 |
| JP | 2001-057967 | | 3/2001 |
| JP | 2003-275186 | | 9/2003 |
| JP | 2004-121360 | | 4/2004 |
| JP | 2006-110180 | | 4/2006 |
| JP | 2006-136405 | | 6/2006 |
| JP | 2006-520657 | | 9/2006 |
| JP | 2007-045967 | | 2/2007 |
| JP | 2007-503910 | | 3/2007 |
| JP | 2007-504917 | | 3/2007 |
| JP | 2007-097822 | | 4/2007 |
| JP | 2007-296266 | | 11/2007 |
| JP | 2008-532596 | | 8/2008 |
| JP | 2008-200120 | | 9/2008 |
| JP | 2009-518099 | | 5/2009 |
| JP | 2009-525816 | | 7/2009 |
| JP | 2011-514831 | | 5/2011 |
| JP | 2011-516110 | | 5/2011 |
| JP | 2011-519583 | | 7/2011 |
| JP | 3180038 | U | 11/2012 |
| JP | 2013-521966 | | 6/2013 |
| JP | 5203973 | | 6/2013 |
| JP | 2013-531512 | | 8/2013 |
| JP | 1483906 | S | 10/2013 |
| JP | 2014-008166 | | 1/2014 |
| JP | 5559425 | | 7/2014 |
| JP | 2014-150826 | | 8/2014 |
| JP | 2014-236982 | | 12/2014 |
| JP | 2015-521085 | | 7/2015 |
| JP | 2015-530225 | | 10/2015 |
| JP | 2015-531954 | | 11/2015 |
| JP | 2016-504159 | | 2/2016 |
| JP | 2013-517053 | | 5/2016 |
| JP | 2016-523139 | | 8/2016 |
| JP | 2017-136380 | | 8/2017 |
| JP | 6198849 | | 9/2017 |
| JP | 2017-209482 | | 11/2017 |
| JP | 2018-504148 | | 2/2018 |
| JP | 2018-508325 | | 3/2018 |
| JP | 2018-513702 | | 5/2018 |
| JP | 6336640 | | 5/2018 |
| JP | D1596476 | | 8/2018 |
| JP | 2018-153651 | | 10/2018 |
| JP | 2018-174995 | | 11/2018 |
| JP | 2018-202159 | | 12/2018 |
| JP | 2019-503761 | | 2/2019 |
| JP | 6491826 | | 3/2019 |
| JP | 6495228 | | 3/2019 |
| JP | 2019-140680 | | 8/2019 |
| JP | 2019-528511 | | 10/2019 |
| JP | 2020-058819 | | 4/2020 |
| JP | 2020-509840 | | 4/2020 |
| JP | 6766199 | | 9/2020 |
| JP | 2021-003591 | | 1/2021 |
| JP | 6901543 | | 6/2021 |
| JP | 2021-525616 | | 9/2021 |
| JP | 2021-166726 | | 10/2021 |
| JP | 2022-501123 | | 1/2022 |
| JP | 2022-037153 | | 3/2022 |
| JP | 2022-038858 | | 3/2022 |
| JP | 2022-126807 | | 8/2022 |
| JP | 2023-508235 | | 3/2023 |
| JP | 2023-074267 | | 5/2023 |
| JP | 2023-100210 | | 7/2023 |
| JP | 2023-536981 | | 8/2023 |
| JP | 2023-536982 | | 8/2023 |
| JP | 7406001 | | 12/2023 |
| JP | 2024-009608 | | 1/2024 |
| JP | 2024-502335 | | 1/2024 |
| JP | 2024-021061 | | 2/2024 |
| JP | 2024-026058 | | 2/2024 |
| JP | 7431777 | | 2/2024 |
| JP | 2024-050777 | | 4/2024 |
| JP | 2024-521799 | | 6/2024 |
| JP | 2024-087811 | | 7/2024 |
| JP | 2024-104034 | | 8/2024 |
| JP | 7551696 | | 9/2024 |
| JP | 2024-164285 | | 11/2024 |
| JP | 2025-000653 | | 1/2025 |
| JP | 2025-500035 | | 1/2025 |
| JP | 7667221 | | 4/2025 |
| JP | 7796108 | | 12/2025 |
| JP | 7882955 | | 6/2026 |
| KR | 3003784570000 | | 3/2005 |
| KR | 1020050055072 | | 6/2005 |
| KR | 1020140050374 | | 4/2014 |
| KR | 10-1513288 | | 4/2015 |
| KR | 3008476060000 | | 3/2016 |
| KR | 3008476090000 | | 3/2016 |
| KR | 3008482960000 | | 3/2016 |
| KR | 3008584120000 | | 6/2016 |
| KR | 3008953750000 | | 2/2017 |
| KR | 3008953760000 | | 2/2017 |
| KR | 3008987790000 | | 3/2017 |
| KR | 1020170133527 | | 12/2017 |
| KR | 3009445870000 | | 2/2018 |
| KR | 3009547690000 | | 4/2018 |
| KR | 3009547710000 | | 4/2018 |
| KR | 10-2019-0114694 | | 10/2019 |
| KR | 10-2563372 | | 7/2023 |
| KR | 10-2023-0119036 | | 8/2023 |
| KR | 10-2024-0116830 | | 7/2024 |
| KR | 10-2811696 | | 5/2025 |
| WO | WO 87/01024 | | 2/1987 |
| WO | WO 99/023943 | | 5/1999 |
| WO | WO 01/016607 | | 3/2001 |
| WO | WO 2002/022006 | | 3/2002 |
| WO | WO 2003/043494 | | 5/2003 |
| WO | WO 2004/100785 | | 11/2004 |
| WO | WO 2005/025668 | | 3/2005 |
| WO | WO 2005/037946 | | 4/2005 |
| WO | WO 2005/084533 | | 9/2005 |
| WO | WO 2006/094513 | | 9/2006 |
| WO | WO 2006/109072 | | 10/2006 |
| WO | WO 2007/049080 | | 3/2007 |
| WO | WO 2007/036748 | | 4/2007 |
| WO | WO 2007/063436 | | 6/2007 |

(56) References Cited

FOREIGN PATENT DOCUMENTS

| | | | |
|---|---|---|---|
| WO | WO 2007/066270 | | 6/2007 |
| WO | WO 2007/071180 | | 6/2007 |
| WO | WO 2007/072069 | | 6/2007 |
| WO | WO 2007/092543 | | 8/2007 |
| WO | WO 2008/005015 | | 1/2008 |
| WO | WO 2008/005016 | | 1/2008 |
| WO | WO 2008/057884 | | 5/2008 |
| WO | WO 2008/120154 | | 10/2008 |
| WO | WO 2009/055397 | | 4/2009 |
| WO | WO 2009/074928 | | 6/2009 |
| WO | WO 2009/112972 | | 9/2009 |
| WO | WO 2009/112976 | | 9/2009 |
| WO | WO 2009/112979 | | 9/2009 |
| WO | WO 2009/134826 | | 11/2009 |
| WO | WO 2010/014490 | | 2/2010 |
| WO | WO 2010/104952 | | 9/2010 |
| WO | WO 2010/105203 | | 9/2010 |
| WO | WO 2010/107913 | | 9/2010 |
| WO | WO 2010/093900 | | 10/2010 |
| WO | WO 2011/077097 | | 6/2011 |
| WO | WO 2011/084636 | | 7/2011 |
| WO | WO 2011/112420 | | 9/2011 |
| WO | WO 2011/143490 | | 11/2011 |
| WO | WO 2011/149755 | | 12/2011 |
| WO | WO 2012/003840 | | 1/2012 |
| WO | WO 2012/009453 | | 1/2012 |
| WO | WO 2012/061509 | | 5/2012 |
| WO | WO 2012/061518 | | 5/2012 |
| WO | WO 2012104657 | | 8/2012 |
| WO | WO 2012/125425 | | 9/2012 |
| WO | WO 2012/140559 | | 10/2012 |
| WO | WO 2012/149466 | | 11/2012 |
| WO | WO 2012/160550 | | 11/2012 |
| WO | WO 2013/065147 | | 5/2013 |
| WO | WO 2013/179368 | | 12/2013 |
| WO | WO 2014/047032 | | 3/2014 |
| WO | WO 2014/047205 | | 3/2014 |
| WO | WO 2014/051563 | | 4/2014 |
| WO | WO 2014/055994 | | 4/2014 |
| WO | WO 2014/116825 | | 7/2014 |
| WO | WO 2014/168841 | | 10/2014 |
| WO | WO 2014/197822 | | 12/2014 |
| WO | WO 2015/089484 | | 6/2015 |
| WO | WO 2015/127466 | | 8/2015 |
| WO | WO 2016/044514 | | 3/2016 |
| WO | WO 2016/044515 | | 3/2016 |
| WO | WO 2016/044519 | | 3/2016 |
| WO | WO 2016/057728 | | 4/2016 |
| WO | WO 2016/070128 | | 5/2016 |
| WO | WO 2016/130545 | | 8/2016 |
| WO | WO 2016/172201 | | 10/2016 |
| WO | WO 2016/181321 | | 11/2016 |
| WO | WO 2017/039518 | | 3/2017 |
| WO | WO 2017/041014 | | 3/2017 |
| WO | WO 2017/043597 | | 3/2017 |
| WO | WO 2017/043603 | | 3/2017 |
| WO | WO 2017/108215 | | 6/2017 |
| WO | WO 2017/159635 | | 9/2017 |
| WO | WO 2018/164840 | | 9/2018 |
| WO | WO 2018/218310 | | 12/2018 |
| WO | WO 2019/070978 | | 4/2019 |
| WO | WO 2019/071201 | | 4/2019 |
| WO | WO 2019/188311 | | 10/2019 |
| WO | WO 2019/191487 | | 10/2019 |
| WO | WO 2019/233807 | | 12/2019 |
| WO | WO 2020/008864 | | 1/2020 |
| WO | WO 2020/013895 | | 1/2020 |
| WO | WO 2020/041363 | | 2/2020 |
| WO | WO 2020/058314 | | 3/2020 |
| WO | WO 2020/072989 | | 4/2020 |
| WO | WO 2020/224041 | | 11/2020 |
| WO | WO 2020/0226852 | | 11/2020 |
| WO | WO 2020/262403 | | 12/2020 |
| WO | WO 2021/055870 | | 3/2021 |
| WO | WO 2021/150122 | | 7/2021 |
| WO | WO 2021/163331 | | 8/2021 |
| WO | WO 2021/200245 | | 10/2021 |
| WO | WO 2021/200764 | | 10/2021 |
| WO | WO 2021/205788 | | 10/2021 |
| WO | WO 2021/210592 | | 10/2021 |
| WO | WO 2021/241308 | | 12/2021 |
| WO | WO 2021245203 | | 12/2021 |
| WO | WO 2022034045 | | 2/2022 |
| WO | WO 2022093709 | | 5/2022 |
| WO | WO 2022/147520 | | 7/2022 |
| WO | WO 2022/251636 | | 12/2022 |
| WO | WO 2023/114742 | | 6/2023 |
| WO | WO 2024/102663 | A2 | 5/2024 |

OTHER PUBLICATIONS

3M Corporation, "3M Surgical Tapes—Choose the Correct Tape" quicksheet (2004).

Altini, et al., An ECG Patch Combining a Customized Ultra-Low-Power Ecg Soc Withbluetooth Low Energy for Long Term Ambulatory Monitoring, Conference: Proceddings of Wireless Health 2011, WH 2011, Oct. 10-13, 2011.

British-Made Early Warning Monitor a "Game Changer", healthcare-in-europe.com, Mar. 31, 2014.

Comstock, Proteus Digital Health Quietly Launches Consumer-Facing Wearable for Athletes, Mobile Health News, Oct. 29, 2014.

Coxworth, Small Adhesive Partch Outperforms Traditional Tech for Detecting Arrhythmia, Scripps, iRhythm Technologies, Jan. 3, 2014.

Del Mar et al.; The history of clinical holter monitoring; A.N.E.; vol. 10; No. 2; pp. 226-230; Apr. 2005.

Enseleit et al.; Long-term continuous external electrocardiogramg: a review; Eurospace; vol. 8; pp. 255-266; 2006.

Feng-Tso Sun et al., "PEAR: Power efficiency through activity recognition (for ECG-based sensing)", Pervasive Computing Technologies for Healthcare (Pervasivehealth) 2011 5th International Conference on, IEEE, May 23, 2011. pp. 115-122.

Hoefman et al.; Optimal duration of event recording for diagnosis of arrhythmias in patients with palpitations and light-headedness in the general practice; Family Practice; Dec. 7, 2006.

Huyett "Keystock & Shim Stock Catalog" p. 9 Feb. 2014. found at https://issuu.com/glhuyett/docs/gl-huyett-keystock-catalog/20 (Year: 2014).

Ikeda Y. et al., "A Method for Transmission Data Reduction for Automated Monitoring System via CNN Distribution Process", Proceedings of the Symposium of Multi-media, Distribution, Coordination, and Mobile (DOCOMO2019), Jul. 2019.

International Preliminary Report on Patentability and Written Opinion in PCT Application No. PCT/US2014/012749, dated Aug. 6, 2015.

International Search Report and Written Opinion in PCT Application No. PCT/US2014/012749, dated Mar. 21, 2014.

Kennedy et al.; The history, science, and innovation of holter technology; A.N.E.; vol. 11; No. 1; pp. 85-94; 2006.

"Mayo Alumni", Mayo Clinic, Rochester, MN, Spring 2011, in 24 pages.

Medtronic Launches Seeq Wearable Cardiac Monitoring System in United States, Diagnostic and Interventional Cardiology, Oct. 7, 2014.

Mundt et al. "A Multiparameter Wearable Physiologic Monitoring System for Space and TerrestrialApplications" IEEE Transactions on Information Technology in Biomedicine, vol. 9, No. 3, pp. 382-384, Sep. 2005.

Prakash, New Patch-Based Wearable Sensor Combines Advanced Skin Adhesives and Sensor Technologies, Advantage Business Marketing, Jul. 17, 2012.

Rajpurkar et al., "Cardiologist-Level Arrhythmia Detection with Convolutinal Neural Networks," ARXIV.org, https://arxiv.org/abs/1707.01836, Jul. 6, 2017 in 9 pages.

Redjem Bouhenguel et al., "A risk and Incidence Based Atrial Fibrillation Detection Scheme forWearable Healthcare Computing Devices," Pervasive Computer Technologies for Healthcare, 2012 6th International Conference on, IEEE, pp. 97-104, May 21, 2012.

(56) References Cited

OTHER PUBLICATIONS

Reiffel et al.; Comparison of autotriggered memory loop recorders versus standard loop recordersversus 24-hour holter monitors for arrhythmia detection; Am. J. Cardiology; vol. 95; pp. 1055-1059; May 1, 2005.
Request for Reexamination of U.S. Pat. No. 7,020,508 under 35 U.S.C §§ 311-318 and 37 CFR. § 1.913 as submitted Sep. 14, 2012 in 78 pages.
Scapa Medical product listing and descriptions (2008) available athttp://www.caapana.com/productlist.jsp and http://www.metplus.co.rs/pdf/prospekti/Samolepljivemedicinsketrake.pdf; retrieved via WayBack Machine Sep. 24, 2012.
Strong, Wearable Technologies Conference 2013 Europe—Notes and Roundup, Wearable Technologies Conference, Feb. 8, 2013.
Sumner, Stanford Engineers Monitor Heart Health Using Paper-Thin Flexible 'Skin', Stanford Report, May 14, 2013.
Ward et al.; Assessment of the diagnostic value of 24-hour ambulatory electrocardiograma monitoring; Biotelemetry Patient monitoring; vol. 7; 1980.
Ziegler et al.; Comparison of continuous versus intermittent monitoring of atrial arrhythmias; Heart Rhythm; vol. 3; No. 12; pp. 1445-1452; Dec. 2006.
Zimetbaum et al.; The evolving role of ambulatory arrhythmia monitoring in general clinic practice; Ann. Intern. Med.; vol. 130; pp. 846-8556; 1999.
Zimetbaum et al.; Utility of patient-activated cardiac event recorders in general clinical practice; The Amer. J. of Cardiology; vol. 79; Feb. 1, 1997.
AAMI, Ambulatory electrocardiogramerican National Standards Institute, Inc. Oct. 29, 1998, in 67 pages.
AAMI, "Cardiac monitors, heart rate meters, and alarms," American National Standards Institute, Inc, May 6, 2002, in 87 pages.
ACLS Medical Training, "The Basics of ECG," retrieved from URL: https://www.aclsmedicaltraining.com/basics-of-ecg/, in 3 pages.
Adamec et al., "ECG Holter: Guide to Electrocardiogramterpretation," Springer Science Business Media, LLC, in 9 pages.
Akram, Muhammad Usman, "Application of Prototype Based Fuzzy Classifiers for ECG based Cardiac Arrhythmia Recognition", Jan. 1, 2008 retrieved from faculty.pieas.edu.pk/Fayyaz/_static/pubfiles/student/usman_thesis.pdf [retrieved on Feb. 17, 2015] in 93 pages.
AlGhatrif et al., "A brief review: history to understand fundamentals of electrocardiography," CoActrion, Apr. 30, 2012, in 5 pages.
Ashley et al., "Cardiology Explained," Remedica, 2004, retreieved from URL: https://www.ncbi.nlm.nih.gov/books/NBK2204/?report=printable, in 4 pages.
Behind the Design: How iRhythm Built Its New Zio Monitor. Online, published date Oct. 4, 2023. Retrieved on Jun. 18, 2024 from URL: https://www.mddionline.com/cardiovascular/behind-the-design-how-irhythm-built-its-new-zio-monitor.
Cadogan, "Norman J. Holter," Life in the Fastlane, Jul. 27, 2022 in 8 pages.
Chung, "Ambulatory Electrocardiography," Springer-Verlag New York Inc., 1979 in 25 pages.
Crawford et al., "ACC/AHA Guidelines for Ambulatory Electrocardiogramacutive Summary and Recommendations," American College of Cardiology / American Heart Association, Aug. 24, 1999, in 20 pages.
DEXCOM STS Sensor, "Instructions for Use," in 51 pages.
Grant, "Spatial Vector Electrocardiogramethod for Calculating the Spatial Electrical Vectors of the Heart from Conventional Leads," Circulation, vol. 11, Nov. 1950, in 20 pages.
Harland et al., "Electric potential probes—new directions in the remote sensing of the human body," Institute of Physics Publishing, Dec. 21, 2001, pp. 163-169.
Hubner, "Which Disposable Chest Electrode?" British Medical Journal, 1969, pp. 507-510.
Kalahasty et al., "A Brief History of Remote Cardiac Monitoring," Virginia Commonwealth University School of Medicine and VCUHS Medical Center, 2013 in 8 pages.
Khandpur, "Printed Circuit Boards: Design, Fabrication, Assembly and Testing," McGraw-Hill, 2006, in 43 pages.
Mill-Max, "Spring-Loaded Connectors," Mil-Max mfg. Corp, Catalog in 85 pages.
Morganroth, "Ambulatory Holter Electrocardiogramaice of Technologies and Clinical Uses," Annais of Internal Medicine, vol. 102, No. 1, Jan. 1985, in 9 pages.
National Library of Medicine, "In brief: What is an electrocardiogram (ECG)?" Jun. 6, 2023, retrieved from URL: https://www.ncbi.nlm.nih.gov/books/NBK536878/ in 4 pages.
Prutchi et al., "Design and Development of Medical Electronic Instrumentation: A Practical Perspective of the Design, Construction, and Test of Medical Devices," Wiley-Interscience, 2005 in 6 pages.
Thakor, "From Holter Monitors to Automatic Defibrillators: Developments in Ambulatory Arrhythmia Monitoring," IEEE Transactions on Biomedical Engineering, vol. BME-31, No. 12, Dec. 1984, in 9 pages.
Trend et al., "Are ECG Welsh cup electrodes effectively cleaned?" Journal of Hospital Infection, 1989, pp. 325-331.
Young et al., "University Physics," Sears & Zemansky, Fifteenth Edition, in 8 pages.
YouTube.com, "Demonstration of Nintendo controller repair," https://www.youtube.com/watch?v=hzybDNChNeU, Aug. 2010.
Aami, "Diagnostic electrocardiographic devices," American National Standards Institute, Inc., Aug. 24, 2007, in 60 pages.
Ahlsen et al., "Service-Oriented Middleware Architecture for Mobile Personal Health Monitoring," MobiHealth 2011, pp. 305-312.
Baas et al., "Accuracy of the Precordial V-Quick Patch in Persons with Cardiac or Pulmonary Disease," The Journal of Emergency Medicine, 2003, vol. 24, No. 2, pp. 131-139.
Becker, "Fundamentals of Electrocardiogramterpretation," Anesthesia Progress, 2006, pp. 53-64.
Bharadwaj, "Accurate ECG Signal Processing," Cypress Semiconductor, Feb. 2011, in 7 pages.
Bowman et al., "Medical Instruments and Devices Used in the Home," CRC Press LLC, 2000, in 8 pages.
Burkhardt, "The Future of Electrocardiogrametry Systems," Int'l Telemetering Conference Proceedings, 2004, in 10 pages.
Caves et al., "Sampled Analog Filtering Using Switched Capacitors as Resistor Equivalents," IEEE Journal of Solid-State Circuits, vol. SC-12, No. 6, Dec. 1977, pp. 592-599.
Chapfuwa et al., "Adversarial Time-To-Event Modeling", 2018 Proceedings of the 35th International Conference on Machine Learning (Year: 2018).
Dallett et al., "Plastic and Adhesives: A Guide to their Physical Properties and Uses," U.S. Naval Ordnance Test Station, 1956, in 6 pages.
Donnay, "Human++: Wireless body-area networks (WBAN) for health monitoring applications," ESF Workshop on Wireless Sensor Networks, Apr. 1-2, 2004, in 22 pages.
Gao et al., "Design of ECG signal acquisition and processing system," 2012 International Conference on Biomedical Engineering and Biotechnology, 2012, pp. 762-764.
Gensheimer et al., "A Scalable Discrete-time Survival Model for Neural Networks", Jan. 25, 2019, Peer J:e6257 (Year:2019).
Greene, "Reuse of Disposable Medical Devices: Historical and Current Aspects," Infection Control & Hosp. Epidemiology, 1986, pp. 508-513.
Gregorian et al., "A Switched-Capacitor High-Pass Filter," IEEE Transactions on Circuits and Systems, Mar. 1980, pp. 226-229.
Gyselinckx et al., "Human++: Autonomous Wireless Sensors for Body Area Networks," IEEE 2005 Custom Integrated Circuits Conference, pp. 13-20.
Gyselinckx et al., "Wireless sensor nodes: potential and challenges," Wireless Sensor Nodes/ESC-353, 2007, in 8 pages.
Higgins, "A Novel Patch for Heart Rhythm Monitoring: Is the Holter Monitor Obsolete," Future Cardiology, 2013, in 10 pages.
Hoffmann et al., "Flexible dry surface-electrodes for ECG long-term monitoring," Proceeding of the 29th Annual International Conference of the IEEE EMBX, Aug. 23-26, 2007, in 4 pages.

(56) References Cited

OTHER PUBLICATIONS

Jacobs, "Sources of Measurement Error in Noninvasive Electronic Instrumentation," Nursing Clinics of North America, Dec 1978, col. 13, No. 4, pp. 573-587.
Kato et al., "An Application of Capacitive Electrode for Detecting Electrocardiogram of Neonates and Infants," Proceeding of the 28th IEEE EMBS Annual International Conference, Aug. 30-Sep. 3, 2006, in 4 pages.
Kholer et al., "The Principles of Software QRS Detection," IEEE ENG. MED. & BIO, 2002, in 16 pages.
Kim, "Implanted Antennas for Medical Wireless Communications: Characterizations, Designs and Performance Evaluations," University of California Los Angeles, 2005, in 24 pages.
Lateef et al., "The V-Quick patch versus the standard 12-lead ECG system: time is the essence," Int J Emerg Med, 2008, pp. 43-48.
Li et al., "Auto-tuning Neural Network Quantization Framework for Collaborative Interference Between the Cloud and Edge", Sep. 27, 2018, Sat. 2015 18th International Conference [Lecture Notes in Computer Science], pp. 402-411, XP047487421.
Morrin et al., "Electrochemical Characterization of Commercial and Home-Made Screen-Printed Carbon Electrodes," Analytical Letters, 2003, vol. 36, No. 9, pp. 2021-2039.
Muhlsteff et al., "Wearable approach for continuous ECG - and Activity Patient-Monitoring," Proceedings of the 26th Annual International Conference of the IEEE EMBS, Sep. 1-5, 2004, in 4 pages.
Neuman, "Biopotential Electrodes," Medical Instrumentation, 1998, in 51 pages.
Nielsen et al., "Automatic QRS Complex Detection Algorithm Designed for a Novel Wearable, Wireless Electrocardiogram Recording Device," 34th Annual International Conference of the IEEE EMBS, Aug. 28-Sep. 1, 2012, pp. 2913-2916.
Nielsen et al., "Strategic Intelligence Monitor on Personal Health Systems, Phase 2," JRC Scientific and Policy Reports, 2013, in 74 pages.
Nolan, "Sterile Medical Device Package Development," Standard Handbook of Biomedical Engineering and Design, 2004, pp. 23.1-23.34.
Nuvant, "Mobile Cardiac Telemetry (MCT) System Instructions for Use," in 16 pages.
Pan et al., "A Real-Time QRS Detection Algorithm," IEEE Transactions on Biomedical Engineering, vol. BME-32, No. 3, Mar. 1985, pp. 230-236.
Poungponsri et al., "An Adaptive Filtering Approach for Electrocardiogram (ECG) Signal Noise Reduction using Neural Networks"; Neurocomputing 117 (2013) pp. 206-213.
Shah, "Polyurethane Thin-Film Welding for Medical Device Applications," Medical Device & Diagnostic Industry, 2002, in 6 pages.
Shu et al., Feature Extraction and Arrhythmia Classification from 2-Lead Electrocardiogram Using Stacked Convolutional Denoising Autoencoders, Journal of Information Processing Society of Japan, Japan, Dec. 2018, vol. 59, No. 12, pp. 2213-2220.
Thakor et al., "Electrode studies for the long-term ambulatory ECG," Medical & Biological Engineering & Computing, Mar. 1985, pp. 116-121.
U.S. Military, "Thermo-Electron and VivoMetrics Deliver the First Real-Time Monitoring Ensemble," EMS1, Apr. 10, 2006 in 7 pages.
Welch et al., "A Wireless ECG Smart Sensor for Broad Application in Life Threatening Event Detection," Proceeding of the 26th Annual International Conference of the IEEE EMBS, Sep. 1-5, 2004, in 3 pages.
Zadeh et al., "Bias in Cross-Entropy-Based Training of Deep Survival Networks", Sep. 2021; IEEE Transactions on Pattern Analysis and Machine Intelligence, vol. 43, No. 9.

PHYSIOLOGICAL MONITORING DEVICE

CROSS-REFERENCE TO RELATED APPLICATIONS

This application is a continuation of U.S. patent application Ser. No. 18/301,881, filed Apr. 17, 2023, which is a continuation of U.S. patent application Ser. No. 16/786,831, filed Feb. 10, 2020, which is a continuation of U.S. patent application Ser. No. 16/397,651, filed Apr. 29, 2019, which is a continuation of U.S. patent application Ser. No. 16/006,719, filed Jun. 12, 2018, which is a continuation of U.S. patent application Ser. No. 14/162,656, filed, Jan. 23, 2014, which claims the benefit of U.S. Provisional Application No. 61/756,326, filed Jan. 24, 2013, entitled PHYSIOLOGICAL MONITORING DEVICE. The contents of the aforementioned applications are hereby incorporated by reference in their entireties as if fully set forth herein. The benefit of priority to the foregoing provisional application is claimed under the appropriate legal basis, including, without limitation, under 35 U.S.C. § 119 (e).

BACKGROUND

Field of the Invention

The invention relates generally to medical devices. More specifically, the invention relates to a physiological monitoring device and method for use.

Description of the Related Art

Abnormal heart rhythms, or arrhythmias, may cause various types of symptoms, such as loss of-consciousness, palpitations, dizziness, or even death. An arrhythmia that causes such symptoms is often an indicator of significant underlying heart disease. It is important to identify when such symptoms are due to an abnormal heart rhythm, since treatment with various procedures, such as pacemaker implantation or percutaneous catheter ablation, can successfully ameliorate these problems and prevent significant symptoms and death.

Since the symptoms listed above can often be due to other, less serious causes, a key challenge is to determine when any of these symptoms are due to an arrhythmia. Oftentimes, arrhythmias occur infrequently and/or episodically, making rapid and reliable diagnosis difficult. Currently, cardiac rhythm monitoring is primarily accomplished through the use of devices, such as Holter monitors, that use short-duration (<1 day) electrodes affixed to the chest. Wires connect the electrodes to a recording device, usually worn on a belt. The electrodes need daily changing and the wires are cumbersome. The devices also have limited memory and recording time. Wearing the device interferes with patient movement and often precludes performing certain activities while being monitored, such as bathing. All of these limitations severely hinder the diagnostic usefulness of the device, the compliance of patients using the device and the likelihood of capturing all important information. Lack of compliance and the shortcomings of the devices often lead to the need for additional devices, follow-on monitoring or other tests to make a correct diagnosis.

Current methods to correlate symptoms with the occurrence of arrhythmias, including the use of cardiac rhythm monitoring devices, such as Holter monitors and cardiac event recorders, are often not sufficient to allow an accurate diagnosis to be made. In fact, Holter monitors have been shown to not lead to a diagnosis up to 90% of the time ("Assessment of the Diagnostic Value of 24-Hour Ambulatory Electrocariographic Monitoring", by DE Ward et al. Biotelemetry Patient Monitoring, vol. 7, published in 1980).

Additionally, the medical treatment process to actually obtain a cardiac rhythm monitoring device and initiate monitoring is typically very complicated. There are usually numerous steps involved in ordering, tracking, monitoring, retrieving, and analyzing the data from such a monitoring device. In most cases, cardiac monitoring devices used today are ordered by a cardiologist or a cardiac electrophysiologist (EP), rather than the patient's primary care physician (PCP). This is of significance since the PCP is often the first physician to see the patient and determine that the patient's symptoms could be due to an arrhythmia. After the patient sees the PCP, the PCP will make an appointment for the patient to see a cardiologist or an EP. This appointment is usually several weeks from the initial visit with the PCP, which in itself leads to a delay in making a potential diagnosis as well as increases the likelihood that an arrhythmia episode will occur and go undiagnosed. When the patient finally sees the cardiologist or EP, a cardiac rhythm monitoring device will usually be ordered. The monitoring period can last 24-48 hours (Holter monitor) or up to a month (cardiac event monitor or mobile telemetry device). Once the monitoring has been completed, the patient typically must return the device to the clinic, which itself can be an inconvenience. After the data has been processed by the monitoring company or by a technician on-site at a hospital or office, a report will finally be sent to the cardiologist or EP for analysis. This complex process results in fewer patients receiving cardiac rhythm monitoring than would ideally receive it.

To address some of these issues with cardiac monitoring, the assignee of the present application developed various embodiments of a small, long-term, wearable, physiological monitoring device. One embodiment of the device is the Zio® Patch (www.irhythmtech.com). Various embodiments are also described, for example, in U.S. Pat. Nos. 8,150,502, 8,160,682 8,244,335, 8,560,046, and 8,538,503, the full disclosures of which are hereby incorporated by reference. Generally, the physiological monitors described in the above references fit comfortably on a patient's chest and are designed to be worn for at least one week and typically two to three weeks. The monitors detect and record cardiac rhythm signal data continuously while the device is worn, and this cardiac rhythm data is then available for processing and analysis.

These smaller, long-term physiological monitoring devices provided many advantages over prior art devices. At the same time, further improvements are desired. One of the most meaningful areas for improvement exists around increasing fidelity of the recorded ECG signal. This is particularly important for single-channel embodiments where a second vector of ECG is not available to clarify whether aberrances in signal are due to arrhythmia or signal artifact. Increases in signal to noise ratio as well as reduction of motion artifact improve efficiency in both algorithmic and human analysis of the recorded ECG signal.

Signal quality is important throughout the duration of wear, but it is particularly critical where the patient marks the record, indicating an area of symptomatic clinical significance. Marking the record is most easily enabled through a trigger located on the external surface of the device. However, since the trigger is part of a skin-contacting platform with integrated electrodes, the patient can introduce significant motion artifacts when feeling for the trigger.

A desirable device improvement would be a symptom trigger that can be activated with minimal addition of motion artifact.

Secondly, patient compliance and device adhesion performance are two factors that govern the duration of the ECG record and consequently the diagnostic yield. Compliance can be increased by improving the patient's wear experience, which is affected by wear comfort, device appearance and the extent to which the device impedes the normal activities of daily living. Given that longer ECG records provide greater diagnostic yield and hence value, improvements to device adhesion and patient compliance are desirable.

Finally, it is desirable for the device to be simple and cost effective to manufacture, enabling scalability at manufacturing as well as higher quality due to repeatability in process. Simplicity of manufacture can also lead to ease of disassembly, which enables the efficient recovery of the printed circuit board for quality-controlled reuse in another device. Efficient reuse of this expensive component is critical for decreasing the cost of the diagnostic monitor. At least some of the objectives will be met by the embodiments described below.

BRIEF SUMMARY

Embodiments described herein are directed to a physiological monitoring device that may be worn continuously and comfortably by a human or animal subject for at least one week or more and more typically two to three weeks or more. In one embodiment, the device is specifically designed to sense and record cardiac rhythm (i.e., electrocardiogram, ECG) data, although in various alternative embodiments one or more additional physiological parameters may be sensed and recorded. The physiological monitoring device includes a number of features to facilitate and/or enhance the patient experience, to make diagnosis of cardiac arrhythmias more accurate, and to make manufacture of the device more simple and cost effective.

In some embodiments, an electronic device for monitoring physiological signals in a mammal comprises:

- at least two flexible wings extending laterally from a rigid housing, wherein the flexible wings comprise a first set of materials which enable the wings to conform to a surface of the mammal and the rigid housing comprises a second set of materials;
- a printed circuit board assembly housed within the rigid housing, wherein the rigid housing is configured to prevent deformation of the printed circuit board in response to movement of the mammal;
- at least two electrodes embedded within the flexible wings, the electrodes configured to provide conformal contact with the surface of the mammal and to detect the physiological signals of the mammal;
- at least two electrode traces embedded within the wings and mechanically decoupled from the rigid housing, the electrode traces configured to provide conformal contact with the surface of the mammal and transmit electrical signals from the electrodes to the printed circuit board assembly; and,
- at least one hinge portion connecting the wings to the rigid housing, the hinge portions configured to flex freely at the area where it is joined to the rigid housing.

In certain embodiments, each wing may comprise an adhesive. In embodiments, the electrodes can be in the same plane as the adhesive. In certain embodiments, each wing comprises at least one rim, wherein the rim is thinner than an adjacent portion of each wing. The rigid housing may further comprise dimples configured to allow for airflow between the rigid housing and the surface of the mammal. In certain embodiments, the rim is configured to prevent the release of a portion of the wing from the surface of the mammal. In some embodiments, an electronic device for monitoring physiological systems may comprise a measuring instrument configured to detect motion signals in at least one axis. This measuring instrument may be an accelerometer that can be configured to detect motion signals in three axes.

In embodiments, the motion signals can be collected in time with the physiological signals. In certain embodiments, a motion artifact is identified when the physiological signals and the motion signals match. Further embodiments may call for an event trigger coupled to the printed circuit board assembly. In some embodiments, the event trigger input is supported by the rigid housing so as to prevent mechanical stress on the printed circuit board when the trigger is activated. The event trigger may be concave and larger than a human finger such that the event trigger is easily located. In certain embodiments, the electrode traces are configured to minimize signal distortion during movement of the mammal. In particular embodiments, gaskets may be used as a means for sealable attachment to the rigid housing.

In certain embodiments, a method for monitoring physiological signals in a mammal may comprise:

- attaching an electronic device to the mammal, wherein the device comprises:
- at least two electrodes configured to detect physiological signals from the mammal,
- at least one measuring instrument configured to detect secondary signals, and
- at least two electrode traces connected to the electrodes and a rigid housing; and,
- comparing the physiological signals to the secondary signals to identify an artifact.

In certain embodiments, identification of an artifact comprises a comparison between the frequency spectrum of the physiological signals and the frequency spectrum of the secondary signals. In embodiments, the secondary signals comprise motion signals that may be used to derive the activity and position of the mammal. In certain embodiments, the secondary signals are collected in three axes. In some embodiments, a tertiary signal may also be collected. In certain embodiments, the secondary signals comprise information about the connection between the electronic device and the mammal. In some embodiments, the secondary signals may be used to detect when the mammal is sleeping.

In some embodiments, a method of removing and replacing portions of a modular physiological monitoring device may comprise

- applying the device of claim 1 to a mammal for a period of time greater than 7 days and collecting physiological data;
- using the device of claim 1 to detect a first set of physiological signals;
- removing the device of claim 1 from the surface of the mammal;
- removing a first component from the device of claim 1; and,
- incorporating the first component into a second physiological monitoring device, the second physiological monitoring device configured to detect a second set of physiological signals.

In some embodiments, the first component is electrically connected to other device components without the use of a permanent connection. In some embodiments, the device may further comprise spring connections. In certain embodiments, the first component may be preserved for a second use by a rigid housing to prevent damage. In particular embodiments, the first component is secured within a device by a mechanism that is capable of re-securing a second component once the first component is removed.

These and other aspects and embodiments of the invention are described in greater detail below, with reference to the drawing figures.

DETAILED DESCRIPTION

The following description is directed to a number of various embodiments. The described embodiments, however, may be implemented and/or varied in many different ways without departing from the scope of the invention. For example, the described embodiments may be implemented in any suitable device, apparatus, or system to monitor any of a number of physiological parameters. For example, the following discussion focuses primarily on long-term, patch-based cardiac rhythm monitoring devices. In one alternative embodiment, a physiological monitoring device may be used, for example, for pulse oximetry and diagnosis of obstructive sleep apnea. In various alternative embodiments, one size of physiological monitor may be used for adult patients and another size may be used for pediatric patients. The method of using a physiological monitoring device may also vary. In some cases, a device may be worn for one week or less, while in other cases, a device may be worn for at least seven days and/or for more than seven days, for example between fourteen days and twenty-one days or even longer. Many other alternative embodiments and applications of the described technology are possible. Thus, the following description is provided for exemplary purposes only. Throughout the specification, reference may be made to the term "conformal." It will be understood by one of skill in the art that the term "conformal" as used herein refers to a relationship between surfaces or structures where a first surface or structure fully adapts to the contours of a second surface or structure.

Figure 1A:
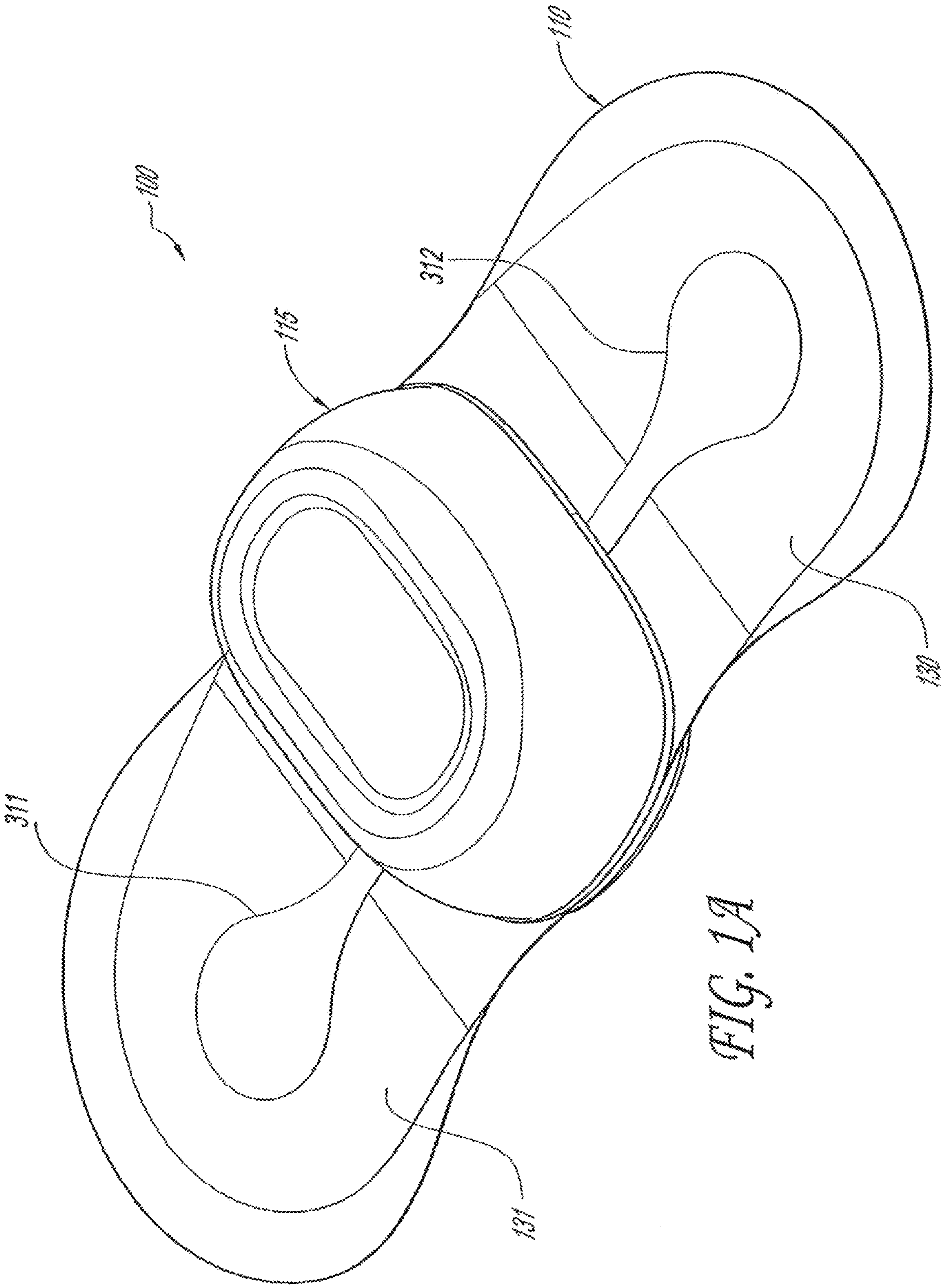
FIGS. 1A and 1B are perspective and exploded views, respectively, of a physiological monitoring device, according to one embodiment.
Figure 1B:
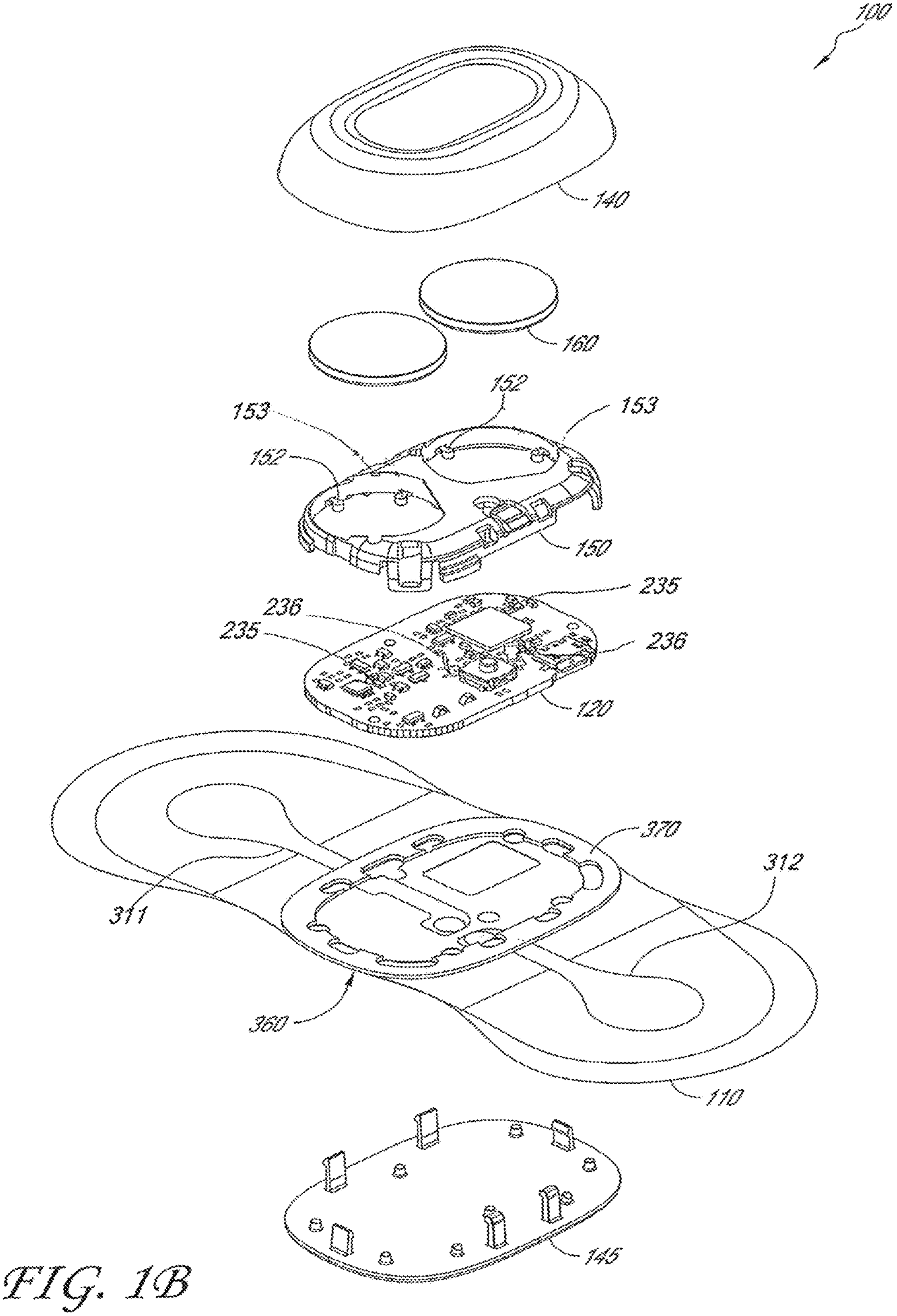

Referring to FIGS. 1A and 1B, perspective and exploded views of one embodiment of a physiological monitoring device 100 are provided. As seen in FIG. 1A, physiological monitoring device 100 may include a flexible body 110 coupled with a watertight, rigid housing 115. Flexible body 110 (which may be referred to as "flexible substrate" or "flexible construct") typically includes two wings 130, 131, which extend laterally from rigid housing 115, and two flexible electrode traces 311, 312, each of which is embedded in one of wings 130, 131. Each electrode trace 311, 312 is coupled, on the bottom surface of flexible body 110, with a flexible electrode (not visible in FIG. 1A). The electrodes are configured to sense heart rhythm signals from a patient to which monitoring device 100 is attached. Electrode traces 311, 312 then transmit those signals to electronics (not visible in FIG. 1A) housed in rigid housing 115. Rigid housing 115 also typically contains a power source, such as one or more batteries.

As will be explained in further detail below, the combination of a highly flexible body 110, including flexible electrodes and electrode traces 311, 312, with a very rigid housing 115 may provide a number of advantages. For example, flexible body 110 includes a configuration and various features that facilitate comfortable wearing of device 100 by a patient for fourteen (14) days or more without removal. Rigid housing 115, which typically does not adhere to the patient in the embodiments described herein, includes features that lend to the comfort of device 100. Rigid housing 115 also protects the electronics and power source contained in housing 120, enhances the ability of a patient to provide an input related to a perceived cardiac event, and allows for simple manufacturing and reusability of at least some of the contents of housing 115. These and other features of physiological monitoring device 100 are described in greater detail below.

Referring now to FIG. 1B, a partially exploded view of physiological monitoring device 100 illustrates component parts that make up, and that are contained within, rigid housing 115 in greater detail. In this embodiment, rigid housing 115 includes an upper housing member 140, which detachably couples with a lower housing member 145. Sandwiched between upper housing member 140 and lower housing member 145 are an upper gasket 370, and a lower gasket 360 (not visible on FIG. 1B but just below upper gasket 370). Gaskets 370, 360 help make rigid housing member 115 watertight when assembled. A number of components of monitoring device 100 may be housed between upper housing member 140 and lower housing member 145. For example, in one embodiment, housing 115 may contain a portion of flexible body 110, a printed circuit board assembly (PCBA) 120, a battery holder 150, and two batteries 160. Printed circuit board assembly 120 is positioned within housing 115 to contact electrode traces 311, 312 and batteries 160. In various embodiments, one or more additional components may be contained within or attached to rigid housing 115. Some of these optional components are described further below, in reference to additional drawing figures.

Battery holder 150, according to various alternative embodiments, may hold two batteries (as in the illustrated embodiment), one battery, or more than two batteries. In other alternative embodiments, other power sources may be used. In the embodiment shown, battery holder 150 includes multiple retain tabs 153 for holding batteries 160 in holder 150. Additionally, battery holder 150 includes multiple feet 152 to establish correct spacing of batteries 160 from the surface of PCBA 120 and ensure proper contact with spring fingers 235 and 236. Spring fingers 235 and 236 are used in this embodiment rather than soldering batteries 160 to PCBA 120. Although soldering may be used in alternative embodiments, one advantage of spring fingers 235 and 236 is that they allow batteries 160 to be removed from PCBA 120 and holder 150 without damaging either of those components, thus allowing for multiple reuses of both. Eliminating solder connections also simplifies and speeds up assembly and disassembly of monitoring device 100.

In some embodiments, upper housing member 140 may act as a patient event trigger. When a patient is wearing physiological monitoring device 100 for cardiac rhythm monitoring, it is typically advantageous for the patient to be able to register with device 100 (i.e., log into the device's memory) any cardiac events perceived by the patient. If the patient feels what he/she believes to be an episode of heart arrhythmia, for example, the patient may somehow trigger device 100 and thus provide a record of the perceived event. At some later time, the patient's recorded perceived event could be compared with the patient's actual heart rhythm, recorded by device 100, and this may help determine whether the patient's perceived events correlate with actual cardiac events. One problem with patient event triggers in currently available wearable cardiac rhythm monitoring devices, however, is that a small trigger may be hard to find and/or activate, especially since the monitoring device is typically worn under clothing. Additionally, pressing a trigger button may affect the electronics and/or the electrodes on the device in such a way that the recorded heart rhythm signal at that moment is altered simply by the motion caused to the device by the patient triggering. For example, pressing a trigger may jar one or both of the electrodes in such a way that the recorded heart rhythm signal at that moment appears like an arrhythmia, even if no actual arrhythmia event occurred. Additionally, there is a chance that the trigger may be inadvertently activated, for instance while sleeping or laying on the monitoring device.

In the embodiment shown in FIGS. 1A and 1B, however, rigid housing 115 is sufficiently rigid, and flexible body 110 is sufficiently flexible, that motion applied to housing 115 by a patient may rarely or ever cause an aberrant signal to be sensed by the electrodes. In this embodiment, the central portion of upper housing member 140 is slightly concave and, when pressed by a patient who is wearing device 100, this central portion depresses slightly to trigger a trigger input on PCBA 120. Because the entire upper surface of rigid housing 115 acts as the patient event trigger, combined with the fact that it is slightly concave, it will generally be quite easy for a patient to find and push down the trigger, even under clothing. Additionally, the concave nature of the button allows it to be recessed which protects it from inadvertent activations. Thus, the present embodiment may alleviate some of the problems encountered with patient event triggers on currently available heart rhythm monitors. These and other aspects of the features shown in FIGS. 1A and 1B will be described in further detail below.

Figure 2A:
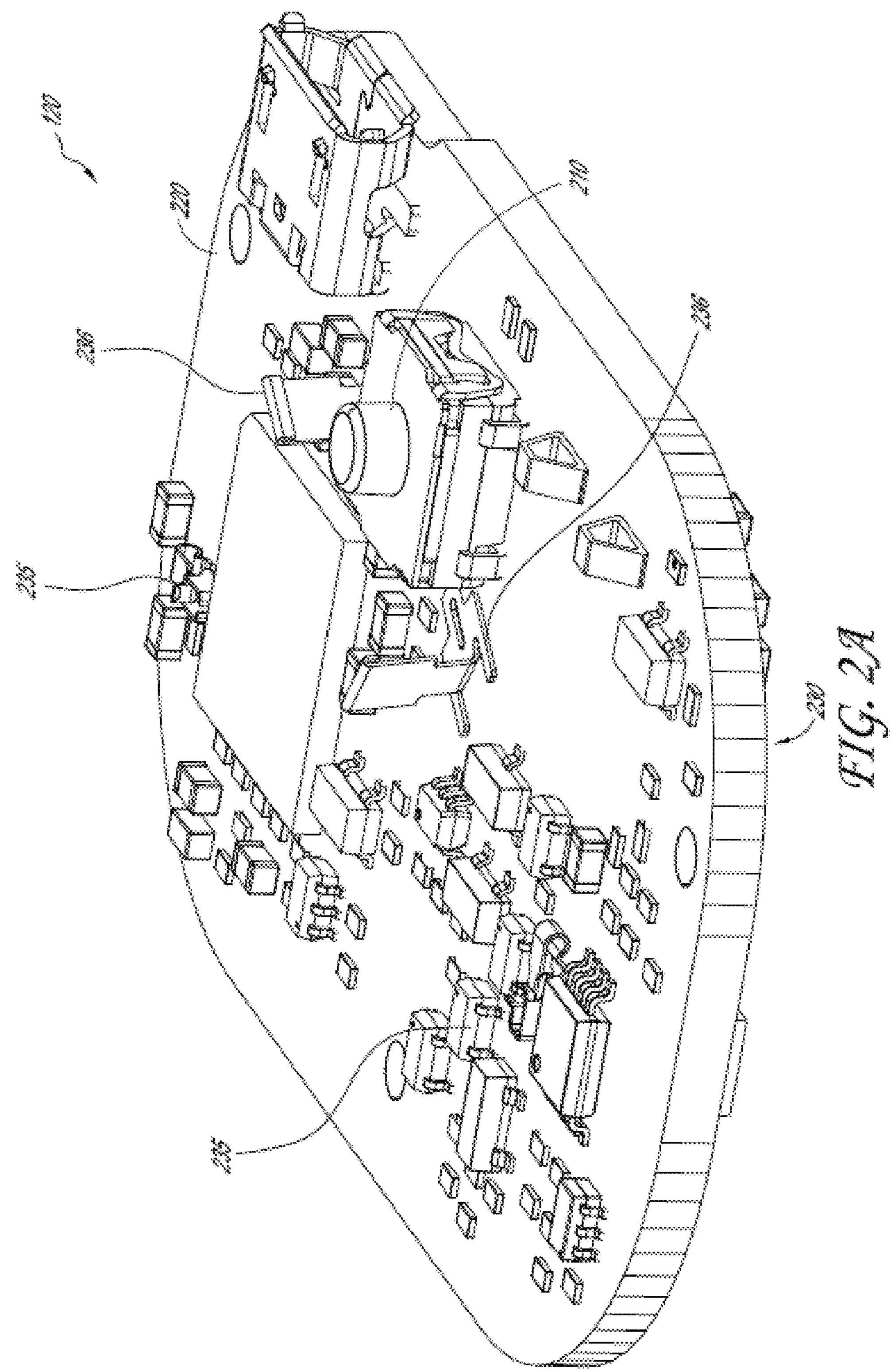
FIGS. 2A and 2B are top perspective and bottom perspective views, respectively, of a printed circuit board assembly of the physiological monitoring device.
Figure 2B:
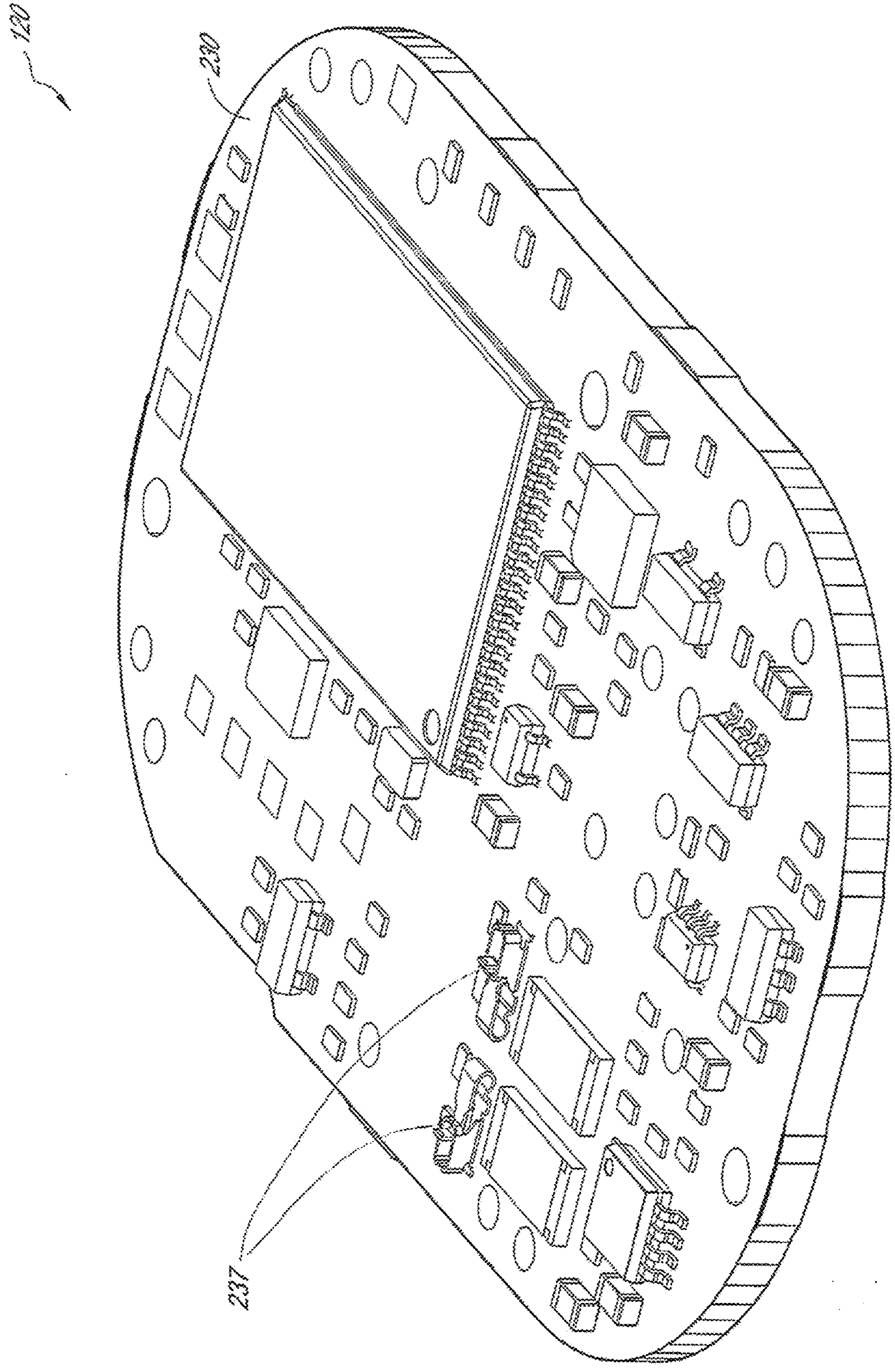

Referring now to FIGS. 2A and 2B, printed circuit board assembly 120 (or "PCBA") may include a top surface 220, a bottom surface 230, a patient trigger input 210 and spring contacts 235, 236, and 237. Printed circuit board assembly 120 may be used to mechanically support and electrically connect electronic components using conductive pathways, tracks or electrode traces 311, 312. Furthermore, because of the sensitive nature of PCBA 120 and the requirement to mechanically interface with rigid body 115, it is beneficial to have PCBA 120 be substantially rigid enough to prevent unwanted deflections which may introduce noise or artifact into the ECG signal. This is especially possible during patient trigger activations when a force is transmitted through rigid body 115 and into PCBA 120. One way to ensure rigidity of the PCBA is to ensure that the thickness of the PCBA is relatively above a certain value. For example, a thickness of at least about 0.08 cm is desirable and, more preferably, a thickness of at least about 0.17 cm is desirable. In this application, PCBA 120 may also be referred to as, or substituted with, a printed circuit board (PCB), printed wiring board (PWB), etched wiring board, or printed circuit assembly (PCA). In some embodiments, a wire wrap or point-to-point construction may be used in addition to, or in place of, PCBA 120. PCBA 120 may include analog circuits and digital circuits.

Patient trigger input 210 may be configured to relay a signal from a patient trigger, such as upper housing member 140 described above, to PCBA 120. For example, patient trigger input 210 may be a PCB switch or button that is responsive to pressure from the patient trigger (i.e., the upper surface of upper housing portion 140). In various embodiments, patient trigger input 210 may be a surface mounted switch, a tactile switch, an LED illuminated tactile switch, or the like. In some embodiments, patient trigger input 210 may also activate an indicator, such as an LED.

One important challenge in collecting heart rhythm signals from a human or animal subject with a small, two-electrode physiological monitoring device such as device 100 described herein, is that having only two electrodes can sometimes provide a limited perspective when trying to discriminate between artifact and clinically significant signals. For example, when a left-handed patient brushes her teeth while wearing a small, two-electrode physiological monitoring device on her left chest, the tooth brushing may often introduce motion artifact that causes a recorded signal to appear very similar to Ventricular Tachycardia, a serious heart arrhythmia. Adding additional leads (and, hence, vectors) is the traditional approach toward mitigating this concern, but this is typically done by adding extra wires adhered to the patient's chest in various locations, such as with a Holter monitor. This approach is not consistent with a small, wearable, long term monitor such as physiological monitoring device 100.

An alternate approach to the problem described above is to provide one or more additional data channels to aid signal discrimination. In some embodiments, for example, device 100 may include a data channel for detecting patch motion. In certain embodiments, an accelerometer may provide patch motion by simply analyzing the change in magnitude of a single axis measurement, or alternatively of the combination of all three axes. The accelerometer may record device motion at a sufficient sampling rate to allow algorithmic comparison of its frequency spectrum with that of the recorded ECG signal. If there is a match between the motion and recorded signal, it is clear that the device recording in that time period is not from a clinical (e.g., cardiac) source, and thus that portion of the signal can be confidently marked as artifact. This technique may be particularly useful in the tooth brushing motion example aforementioned, where the rapid frequency of motion as well as the high amplitude artifact is similar to the heart rate and morphology, respectively, of a potentially life-threatening arrhythmia like Ventricular Tachycardia.

In some embodiments, using the magnitude of all three axes for such an analysis would smooth out any sudden changes in values due to a shift in position rather than a change in activity. In other embodiments, there may be some advantage in using a specific axis of measurement such as along the longitudinal axis of the body to focus on a specific type of artifact introduced by upward and downward movements associated with walking or running. In a similar vein, the use of a gyroscope in conjunction with the accelerometer may provide further resolution as to the nature of the motion experienced. While whole body movements may be sufficiently analyzed with an accelerometer on its own, specific motion of interest such as rotational motion due to arm movement is sufficiently complex that an accelerometer alone might not be able to distinguish.

In addition to detecting motion artifact, an accelerometer tuned to the dynamic range of human physical activities may provide activity levels of the patient during the recording, which can also enhance accuracy of algorithmic true arrhythmia detection. Given the single-lead limitation of device 100, arrhythmias that require observation of less prominent waves (e.g. P-wave) in addition to rate changes such as Supraventricular Tachycardia pose challenges to both computerized algorithms as well as the trained human eye. This particular arrhythmia is also characterized by the sudden nature of its onset, which may be more confidently discriminated from a non-pathological Sinus Tachycardia if a sudden surge in the patient's activity level is detected at the same time as the increase in heart rate. Broadly speaking, the provision of activity information to clinical professionals may help them discriminate between exercise-induced arrhythmia versus not. As with motion artifact detection, a single-axis accelerometer measurement optimized to a particular orientation may aid in more specifically determining the activity type such as walking or running. This additional information may help explain symptoms more specifically and thereby affect the subsequent course of therapeutic action.

In certain embodiments, an accelerometer with 3 axes may confer advantages beyond what magnitude of motions can provide. When the subject is not rapidly moving, 3-dimensional accelerometer readings may approximate the tilt of PCBA 120, and therefore body orientation relative to its original orientation. The original body orientation can be assumed to be in either an upright or supine position which is required for appropriate positioning and application of the device to the body. This information may aid in ruling out certain cardiac conditions that manifest as beat-to-beat morphology changes, such as cardiac *alternans* where periodic amplitude changes are observed, often in heart failure cases. Similar beat-to-beat morphology changes are observable in healthy subjects upon shift in body position due to the shift in heart position relative to the electrode vector, for example from an upright to a slouching position. By design, the single-channel device 100 does not have an alternate ECG channel to easily rule out potential pathological shifts in morphology, however, correlation with shifts in body orientation will help explain these normal changes and avoid unnecessary treatment due to false diagnosis.

In other embodiments, the accelerometer may also be used as a sleep indicator, based on body orientation and movement. When presenting clinical events (e.g., pauses), it is diagnostically helpful to be able to present information in a manner that clearly separates events that occurred during sleep from those during waking hours. In fact, certain algorithms such as for ECG-derived respiratory rate only make sense to run when the patient is in a relatively motionless state and therefore subtle signal modulation introduced by chest movement due to breathing is observable. Respiratory rate information is useful as one channel of information necessary to detect sleep apnea in certain patient populations.

In certain embodiments, the accelerometer may also be used to detect free-falls, such as fainting. With an accelerometer, device 100 may be able to mark fainting (syncope) and other free-fall events without relying on patient trigger. In order to allow timely detection of such critical events, yet considering the battery and memory limitations of a small, wearable device such as device 100, acquisition of accelerometer readings may be done in bursts, where only interesting information such as a potential free fall is written to memory at a high sampling rate. An expansion of this event-trigger concept is to use specific tapping motions on device 100 as a patient trigger instead of or in conjunction with the button previously described. The use and detection of multiple types of tapping sequences may provide better resolution and accuracy into what exactly the patient was feeling, instead of relying on the patient to manually record their symptom and duration in a trigger log after the fact. An example of such added resolution is to indicate the severity of the symptom by the number of sequential taps.

Alternatively, in other embodiments, an optical sensors may be used to distinguish between device motion and patient body motion. Further, in additional embodiments, the device may not require a button or trigger.

Another optional data channel that may be added to physiological monitoring device 100 is a channel for detecting flex and/or bend of device 100. In various embodiments, for example, device 100 may include a strain gauge, piezoelectric sensor or optical sensor to detect motion artifact in device 100 itself and thus help to distinguish between motion artifact and cardiac rhythm data. Y et another optional data channel for device 100 may be a channel for detecting heart rate. For example, a pulse oximeter, microphone or stethoscope may provide heart rate information. Redundant heart rate data may facilitate discrimination of ECG signals from artifact. This is particularly useful in cases where arrhythmia such as Supraventricular Tachycardia is interrupted by artifact, and decisions must be made whether the episode was actually multiple shorter episodes or one sustained episode. Another data channel may be included for detecting ambient electrical noise. For example, device 100 may include an antenna for picking up electromagnetic interference. Detection of electromagnetic interference may facilitate discrimination of electrical noise from real ECG signals. Any of the above-described data channels may be stored to support future noise discrimination or applied for immediate determination of clinical validity in real-time.

Figure 3A:
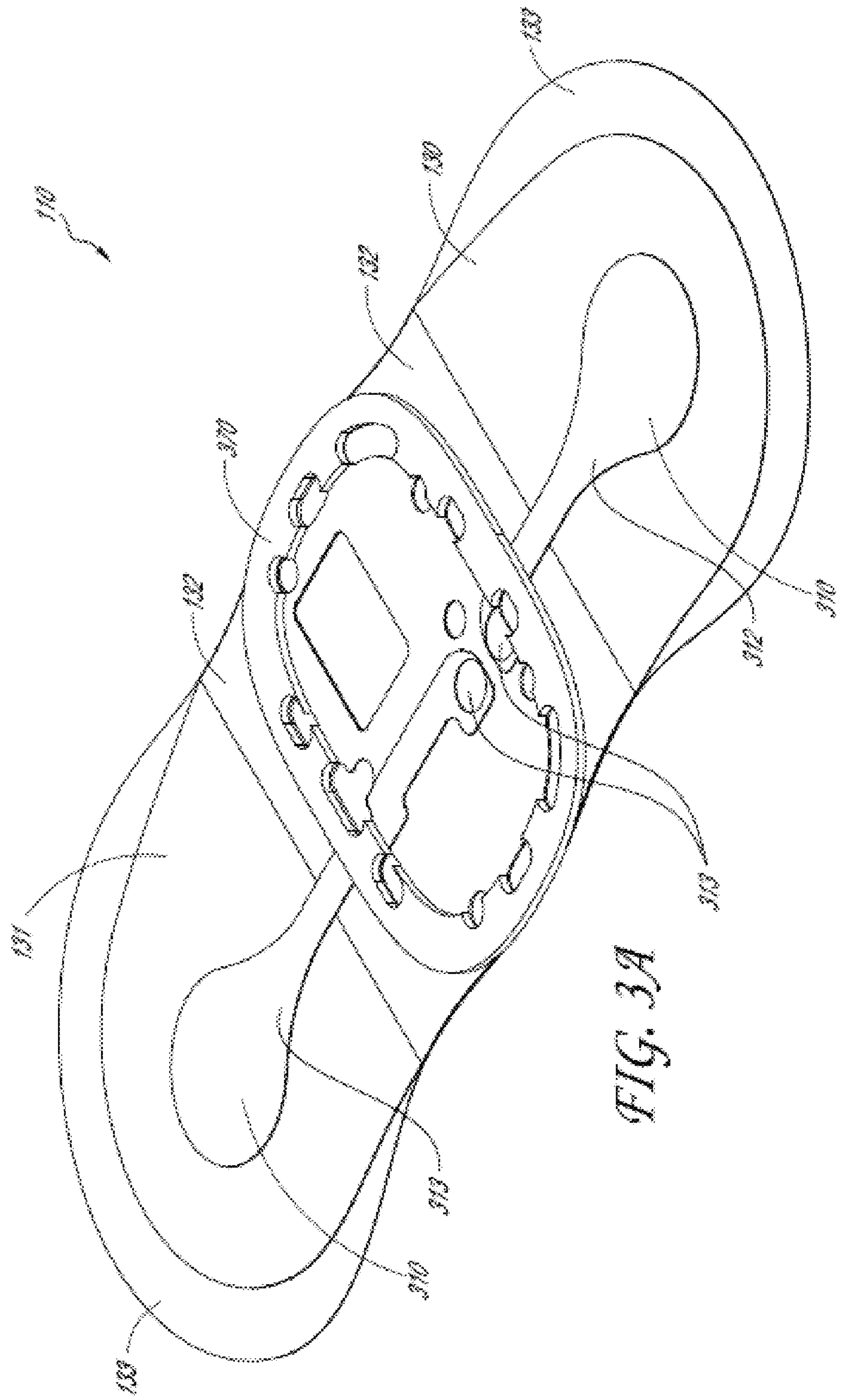
FIGS. 3A-E are perspective and exploded views of a flexible body and gasket of the physiological monitoring device.
Figure 3B:
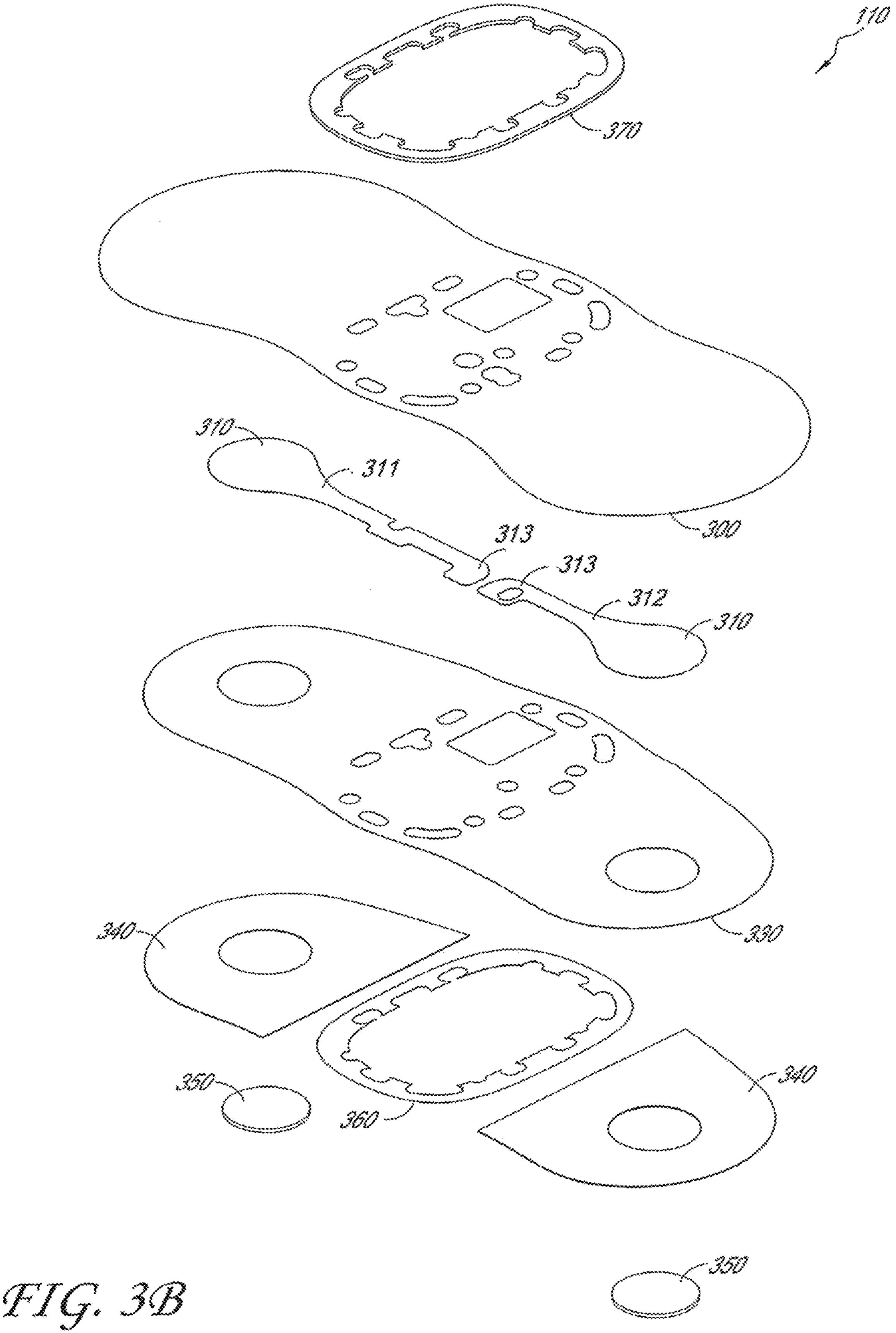

With reference now to FIGS. 3A and 3B, flexible body 110 is shown in greater detail. As illustrated in FIG. 3A, flexible body 110 may include wings 130, 131, a thin border 133 (or "rim" or "edge") around at least part of each wing 130, 131, electrode traces 311, 312, and a hinge portion 132 (or "shoulder") at or near a junction of each wing 130, 131 with rigid housing 115. Also shown in FIG. 3A is upper gasket 370, which is not considered part of flexible body 110 for this description, but which facilitates attachment of flexible body 110 to rigid housing 115.

Hinge portions 132 are relatively thin, even more flexible portions of flexible body 110. They allow flexible body 110 to flex freely at the area where it is joined to rigid housing 115. This enhances comfort, since when the patient moves, housing 115 can freely lift off of the patient's skin. Electrode traces 311, 312 are also very thin and flexible, to allow for patient movement without signal distortion. B orders 133 are portions of flexible body 110 that is thinner than immediately adjacent portions and that provide for a smooth transition from flexible body 110 to a patient's skin, thus preventing edge-lift and penetration of dirt or debris below flexible body 110.

As shown in greater detail in FIG. 3B, flexible body 110 may include multiple layers. As mentioned previously, upper gasket 370 and lower gasket 360 are not considered part of flexible body 110 for the purposes of this description but are shown for completeness of description. This distinction is for ease of description only, however, and should not be interpreted to limit the scope of the claimed invention. Flexible body 110 may include a top substrate layer 300, a bottom substrate layer 330, an adhesive layer 340, and flexible electrodes 350. Top and bottom substrate layers 300, 330 may be made of any suitable, flexible material, such as one or more flexible polymers. Suitable flexible polymers can include, but are not limited to, polyurethane, polyethylene, polyester, polypropylene, nylon, teflon and carbon impregnated vinyl. The material of substrate layers 300, 330 may be selected based on desired characteristics. For example, the material of substrate layers 300, 330 may be selected for flexibility, resilience, durability, breathability, moisture transpiration, adhesion and/or the like. In one embodiment, for example, top substrate layer 300 may be made of polyurethane, and bottom substrate layer 330 may be made of polyethylene or alternatively polyester. In other embodiments, substrate layers 300, 330 may be made of the same material. In yet another embodiment, substrate layer 330 may contain a plurality of perforations in the area over adhesive layer 340 to provide for even more breathability and moisture transpiration. In various embodiments, physiological monitoring device 100 may be worn continuously by a patient for as many as 14-21 days or more, without removal during the time of wear and with device 100 being worn during showering, exercising and the like. Thus, the material(s) used and the thickness and configuration of substrate layers 300, 330 may be essential to the function of physiological monitoring device 100. In some embodiments, the material of substrate layers 300, 330 acts as an electric static discharge (ESD) barrier to prevent arcing.

Typically, top and bottom substrate layers 300, 330 are attached to one another via adhesive placed on one or both layers 300, 330. For example, the adhesive or bonding substance between substrate layers 300, 330 may be an acrylic-based, rubber-based, or silicone-based adhesive. In other alternative embodiments, flexible body 110 may include more than two layers of flexible material.

In addition to the choice of material(s), the dimensions—thickness, length and width—of substrate layers 300, 330 may be selected based on desired characteristics of flexible body 110. For example, in various embodiments, the thickness of substrate layers 300, 330 may be selected to give flexible body 110 an overall thickness of between about 0.1 mm to about 1.0 mm. According to various embodiments, flexible body 110 may also have a length of between about 7 cm and 15 cm and a width of about 3 cm and about 6 cm. Generally, flexible body 110 will have a length sufficient to provide a necessary amount of separation between electrodes 350. For example, a distance from the center of one electrode 350 to the center of the other electrode 350 should be at least about 6.0 cm and more preferably at least about 8.5 cm. This separation distance may vary, depending on the application. In some embodiments, substrate layers 300, 330 may all have the same thickness. Alternatively, the two substrate layers 300, 330 may have different thicknesses.

As mentioned above, hinge portions 132 allow the rigid body 115 to lift away from the patient while flexible body 110 remains adhered to the skin. The functionality of hinge portions 132 is critical in allowing the device to remain adhered to the patient throughout various activities that may stretch and compress the skin. Furthermore, hinge portions 132 allow for significantly improved comfort while wearing the device. Generally, hinge portions 132 will be sufficiently wide enough to provide adequate lift of rigid body 115 without creating too large of a peel force on flexible body 110. For example, in various embodiments, the width of hinge portion 132 should be at least about 0.25 cm and more preferably at least about 0.75 cm.

Additionally, the shape or footprint of flexible body 110 may be selected based on desired characteristics. As seen in FIG. 3A, wings 130, 131 and borders 133 may have rounded edges that give flexible body 110 an overall "peanut" shape. However, wings 130, 131 can be formed in any number of different shapes such as rectangles, ovals, loops, or strips. In the embodiment shown in FIGS. 3A and 3B, the footprint top substrate layer 300 is larger than the footprint of bottom substrate layer 330, with the extension of top substrate layer 300 forming borders 133. Thus, borders 133 are made of the same polyurethane material that top layer 300 is made of. Borders 133 are thinner than an adjacent portion of each wing 130, 131, since they includes only top layer 300. The thinner, highly compliant rim 133 will likely enhance adherence of physiologic monitoring device 100 to a patient, as it provides a transition from an adjacent, slightly thicker portion of wings 130, 131 to the patient's skin and thus helps prevent the edge of device 110 from peeling up off the skin. Border 133 may also help prevent the collection of dirt and other debris under flexible body 110, which may help promote adherence to the skin and also enhance the aesthetics of device 110. In alternative embodiments, the footprint of substrate layers 300, 330 may be the same, thus eliminating borders 133.

While the illustrated embodiments of FIGS. 1A-3B include only two wings 130, 131, which extend from rigid housing 115 in approximately opposite directions (i.e., at a 180-degree angle relative to each other), other configurations are possible in alternative embodiments. For example, in some embodiments, wings 130, 131 may be arranged in an asymmetrical orientation relative to one another and/or one or more additional wings may be included. As long as sufficient electrode spacing is provided to permit physiological signal monitoring, and as long as wings 130, 131 are configured to provide extended attachment to the skin, any suitable configuration and number of wings 130, 131 and electrode traces 311, 312 may be used. The embodiments described above have proven to be advantageous for adherence, patient comfort and accuracy of collected heart rhythm data, but in alternative embodiments it may be possible to implement alternative configurations.

Adhesive layer 340 is an adhesive that is applied to two portions of the bottom surface of bottom substrate layer 330, each portion corresponding to one of wings 130, 131. Adhesive layer 340 thus does not extend along the portion of bottom substrate layer 330 upon which rigid housing 115 is mounted. Adhesive layer 340 may be made of any suitable adhesive, although certain adhesives have been found to be advantageous for providing long term adhesion to patient skin with relative comfort and lack of skin irritation. For example, in one embodiment, adhesive layer 340 is a hydrocolloid adhesive. In another embodiment, the adhesive layer 340 is comprised of a hydrocolloid adhesive that contains naturally-derived or synthetic absorbent materials which take up moisture from the skin during perspiration.

Each of the two portions of adhesive layer 340 includes a hole, into which one of electrodes 350 fits. Electrodes 350 made of flexible material to further provide for overall conformability of flexible body 110. In one embodiment, for example, flexible electrodes 350 may be made of a hydrogel 350. Electrodes 350 generally provide conformal, non-irritating contact with the skin to provide enhanced electrical connection with the skin and reduce motion artifact. In some embodiments, hydrogel electrodes 350 may be punched into adhesive layer 340, thus forming the holes and filling them with hydrogel electrodes 350. In one alternative embodiment, electrodes 350 and adhesive 340 may be replaced with an adhesive layer made of a conductive material, such that the entire adhesive layer on the underside of each wing 130, 131 acts as an electrode. Such an adhesive layer may include a hybrid adhesive/conductive substance or adhesive substance mixed with conductive elements or particles. For example, in one embodiment, such an adhesive layer may be a hybrid of a hydrogel and a hydrocolloid adhesive.

As discussed above, in some embodiments, adhesive layer 340 may cover a portion of the underside of lower substrate layer 330, such that at least a portion of the bottom side of flexible body 110 does not include adhesive layer 340. As seen in FIG. 3A, hinges 132 may be formed in the flexible body 110 as portions of each wing 130, 131 on which adhesive layer 340 is not applied. Hinge portions 132 are generally located at or near the junction of flexible body 110 with rigid housing 115, and thus provide for flexing of device 100 to accommodate patient movement. In some embodiments, hinge portions 132 may have a width that is less than that of adjacent portions of wings 130, 131, thus giving device 100 its "peanut" shape mentioned above. As shown in FIG. 8, as a subject moves, device 100 flexes along with patient movement. Device flexion may be severe and is likely to occur many times during long term monitoring. Hinge portions 132 may allow for dynamic conformability to the subject, while the rigidity of rigid housing 115 may allow housing 115 to pop up off the patient's skin during device flexion, thus preventing peeling of the device 100 off of the skin at its edge.

Figure 3C:
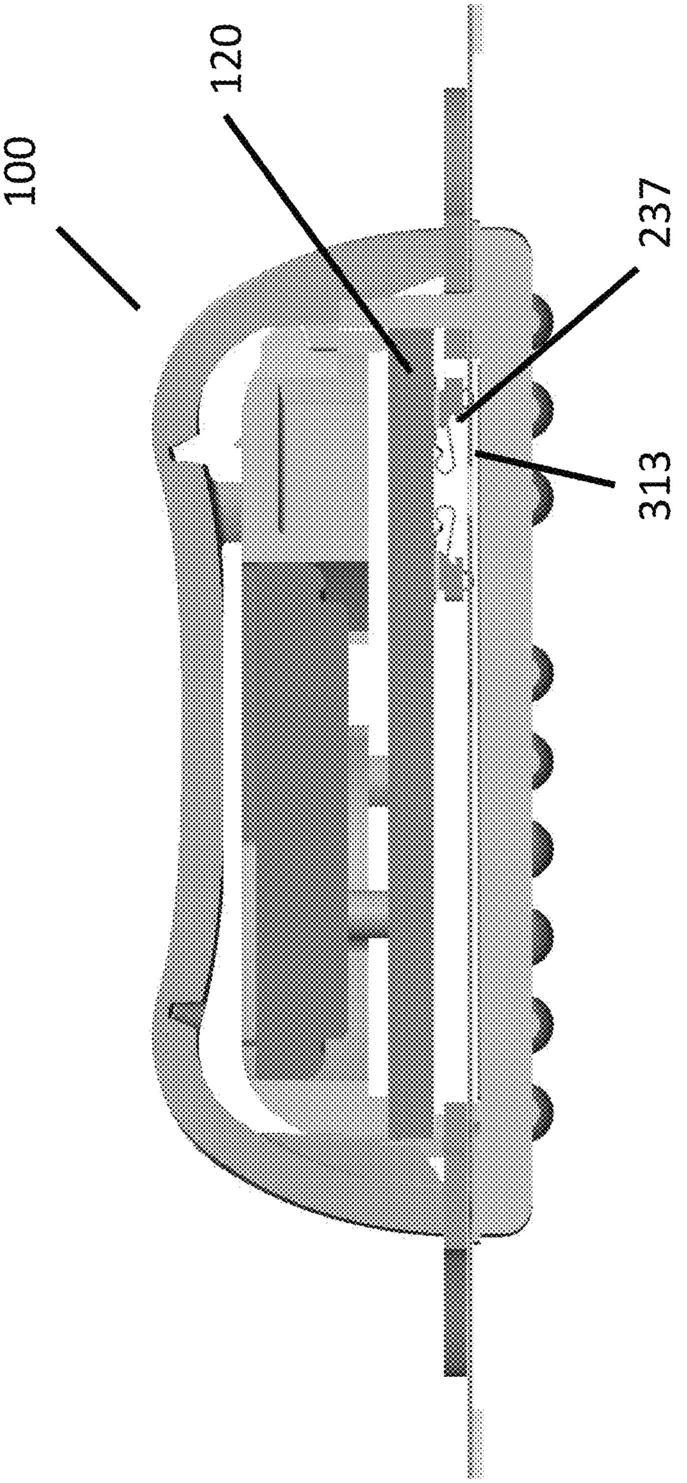
Figure 3D:
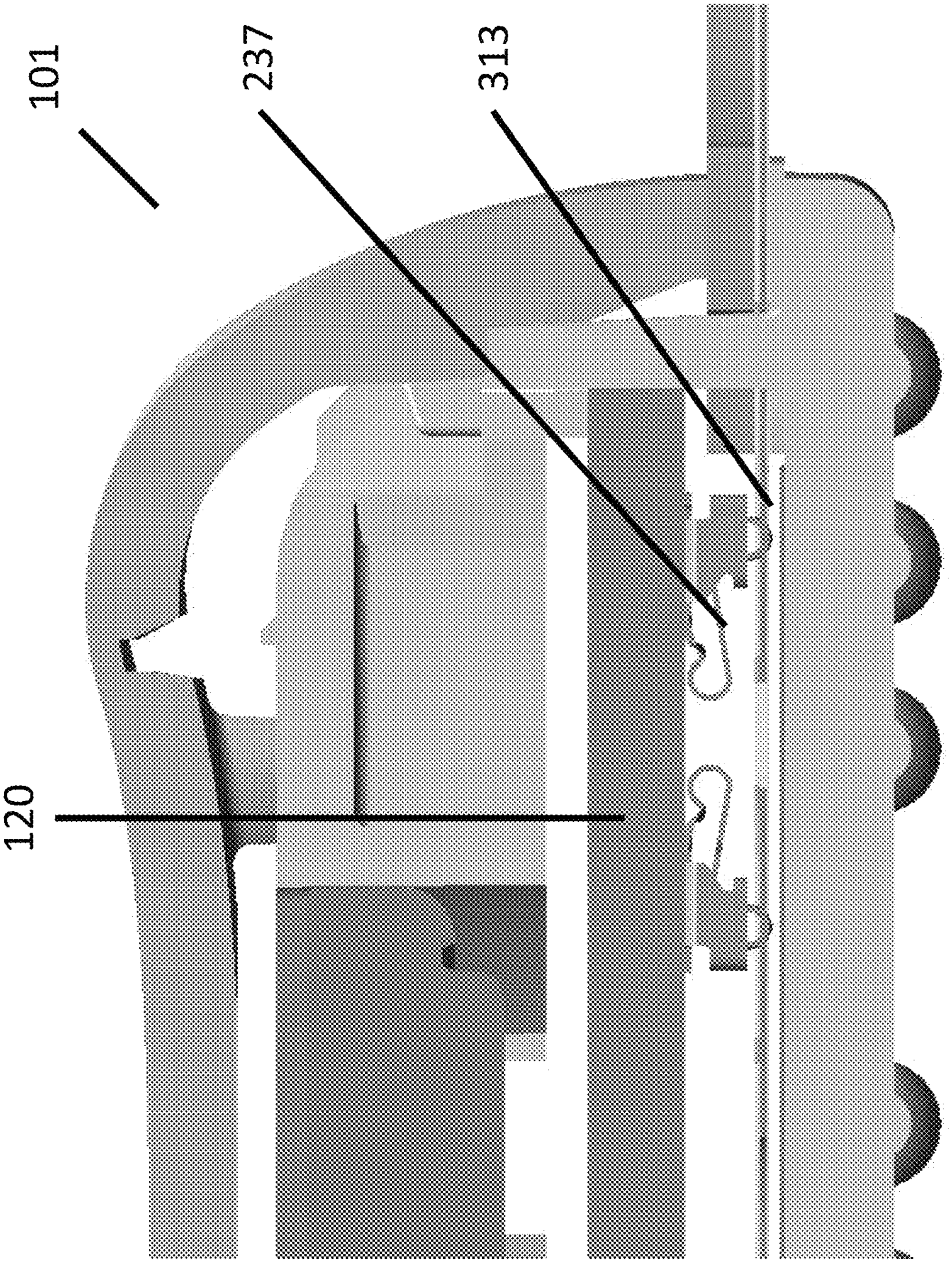

Flexible body 110 further includes two electrode traces 311, 312 sandwiched between upper substrate layer 300 and lower substrate layer 330. Each electrode trace 311, 312 may include an electrode interface portion 310 and an electrocardiogram circuit interface portion 313. As illustrated in FIGS. 3C and 3D, ECG circuit interface portions 313 are in physical contact with spring fingers 237 and provide electrical communication with PCBA 120 when device 100 or zoomed-in device portion 101 is assembled. Electrode interface portions 310 contact hydrogel electrodes 350. Thus, electrode traces 311, 312 transmit cardiac rhythm signals (and/or other physiological data in various embodiments) from electrodes 350 to PCBA 120.

The material and thickness of electrode traces 311, 312 are important for providing a desired combination of flexibility, durability and signal transmission. For example, in one embodiment, electrode traces 311, 312 may include a combination of silver (Ag) and silver chloride (A gCI). The silver and silver chloride may be disposed in layers. For example, one embodiment of electrode traces 311, 312 may include a top layer of silver, a middle layer of carbon impregnated vinyl, and a bottom (patient-facing) layer of silver chloride. In another embodiment, both top and bottom layers of electrode traces 311, 312 may be made of silver chloride. In one embodiment, the top and bottom layers may be applied to the middle layer in the form of silver ink and silver chloride ink, respectively. In an alternative embodiment, each electrode trace may include only two layers, such as a top layer of silver and a bottom layer of silver chloride. In various embodiments, the material of a bottom layer of each electrode trace 311, 312, such as A gCI, may be selected to match the chemistry of the hydrogel electrodes 350 and create a half-cell with the body of the subject.

The thickness of the electrode traces 311, 312 may be selected to optimize any of a number of desirable properties. For example, in some embodiments, at least one of the layers of electrode traces 311, 312 can be of a sufficient thickness to minimize or slow depletion of the material from an anode/cathode effect over time. Additionally, the thickness may be selected for a desired flexibility, durability and/or signal transmission quality. Flexible electrode traces 311, 312 generally may help provide conformal contact with the subject's skin and may help prevent electrodes 350 from peeling or lifting off of the skin, thereby providing strong motion artifact rejection and better signal quality by minimizing transfer of stress to electrodes 350.

Figure 3E:
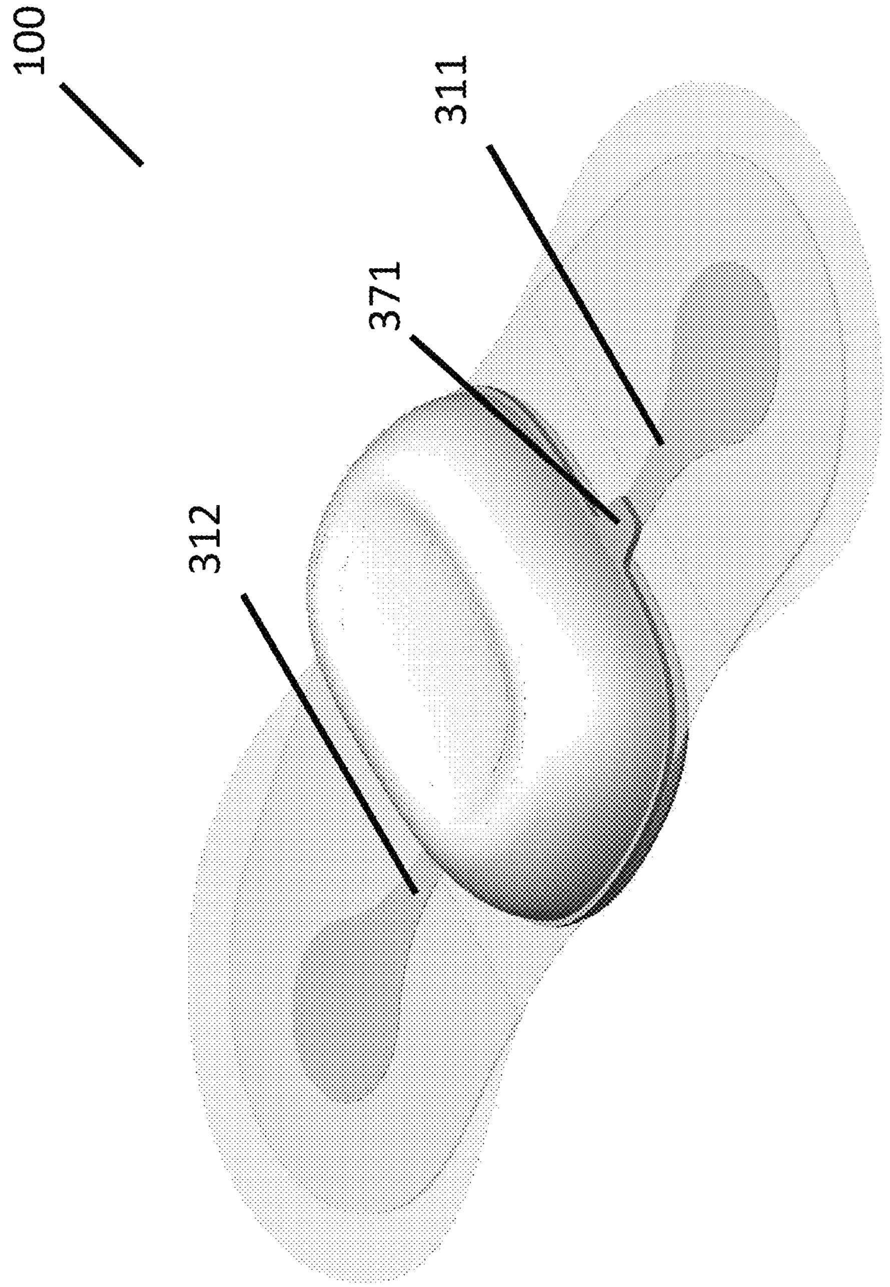

As mentioned above, in some embodiments, top gasket 370 and bottom gasket 360 may be attached upper substrate 300 and lower substrate 330 of flexible body 110. Gaskets 360, 370 may be made of any suitable material, such as urethane, which provides a water tight seal between the upper housing member 140 and lower housing member 145 of rigid housing 115. In one embodiment, top gasket 370 and/or bottom gasket 360 may include an adhesive surface. FIG. 3E depicts yet another embodiment where top gasket 370 includes tabs 371 that protrude away from the profile of top housing 140 while still being adhered to upper substrate 300. The tabs 371 cover a portion of electrode traces 311, 312 and provide a strain relief for the traces at the point of highest stress where the flexible body meets the rigid housing.

Figure 4:
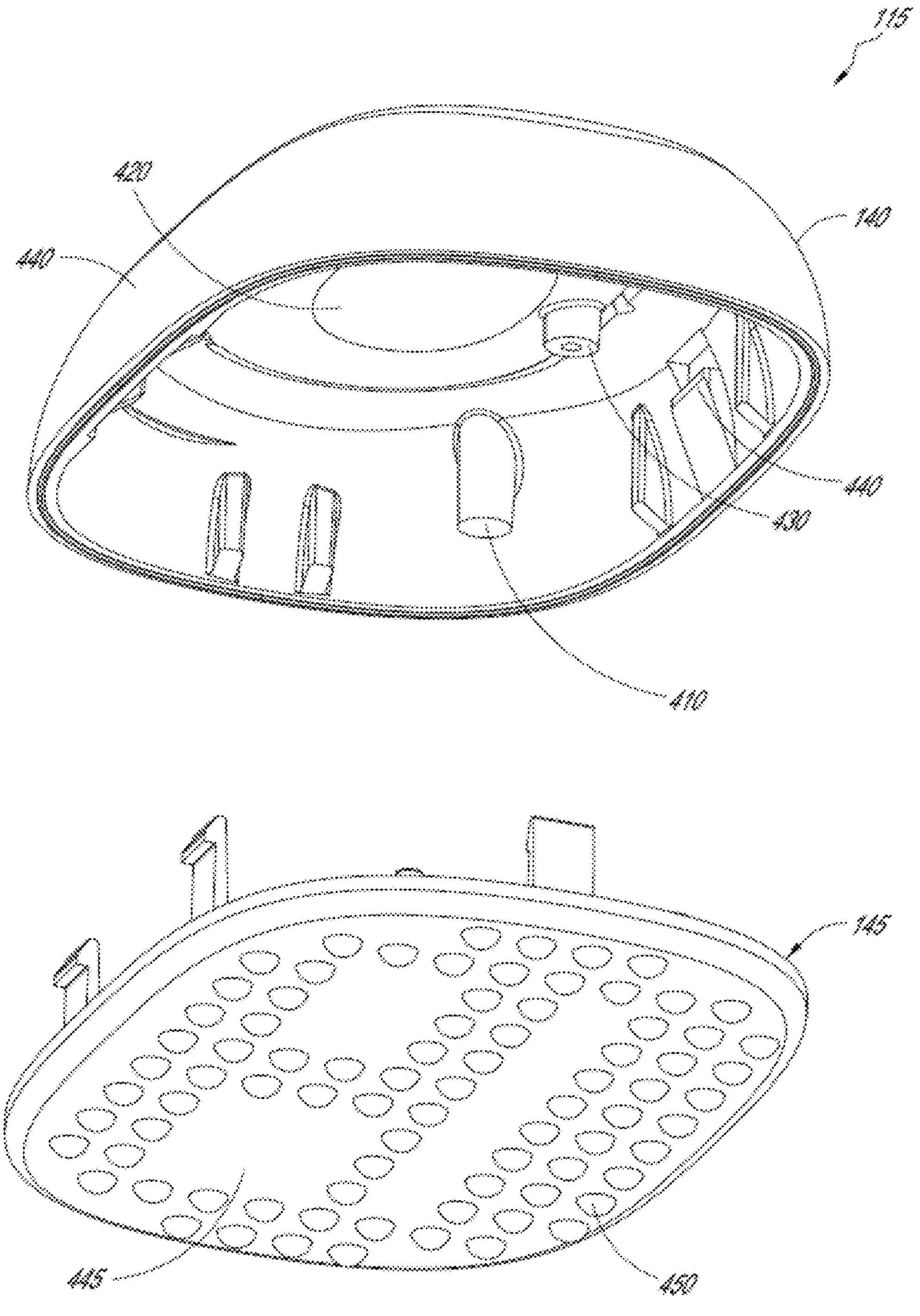
FIG. 4 is an exploded view of a rigid housing of the physiological monitoring device.

With reference now to FIG. 4, upper housing member 140 and lower housing member 145 of rigid housing 115 are shown in greater detail. Upper and lower housing members 140, 145 may be configured, when coupled together with gaskets 360, 370 in between, to form a watertight enclosure for containing PCBA 120, battery holder 150, batteries 160 and any other components contained within rigid housing 115. Housing members 140, 145 may be made of any suitable material to protect internal components, such as water resistant plastic. In one embodiment, upper housing member 140 may include a rigid sidewall 440, a light pipe 410 to transmit visual information from the LEDs on the PCBA through the housing member, a slightly flexible top surface 420, and an inner trigger member 430 extending inward from top surface 420. Top surface 420 is configured to be depressed by a patient when the patient perceives what he or she believes to be an arrhythmia or other cardiac event. When depressed, top surface 420 depresses inner trigger member 430, which contacts and activates trigger input 210 of PCBA 120. Additionally, as discussed previously, top surface 420 may have a concave shape (concavity facing the inside of housing 115) to accommodate the shape of a finger. It is believed that the design of upper housing member 140 isolates activation of the trigger input 210 from electrodes 350, thereby minimizing artifact in the data recording.

With continued reference to FIG. 4, lower housing member 145 may be configured to detachably connect with upper housing member 140 in such a way that housing members 140, 145 may be easily attached and detached for reusability of at least some of the component parts of monitoring device 100. In some embodiments, a bottom surface 445 (patient facing surface) of lower housing member 145 may include multiple dimples 450 (or "bumps," "protrusions" or the like), which will contact the patient's skin during use. Dimples 450 may allow for air flow between bottom surface 445 and the patient's skin, thus preventing a seal from forming between bottom surface 445 and the skin. It is believed that dimples 450 improve comfort and help prevent a perception in currently available devices in which the patient feels as if monitoring device 100 is falling off when it housing 115 lifts off the skin and breaks a seal with the skin. In yet another embodiment the bottom surface 445 of lower housing member 450 may include multiple divots (recesses instead of protrusions) to prevent a seal from forming.

Figure 5A:
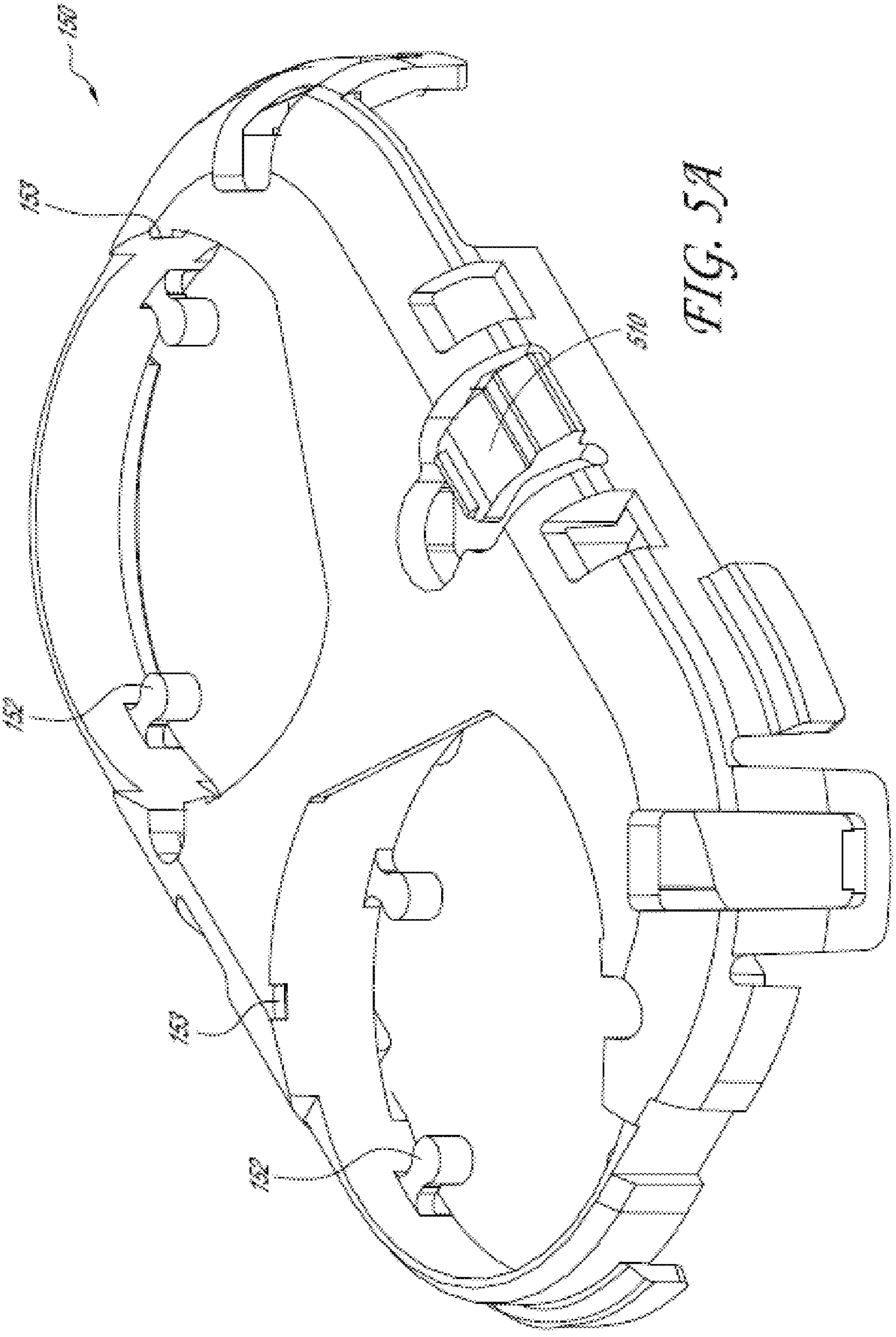
FIG. 5A-B is a perspective view of a battery holder of the physiological monitoring device.
Figure 5B:
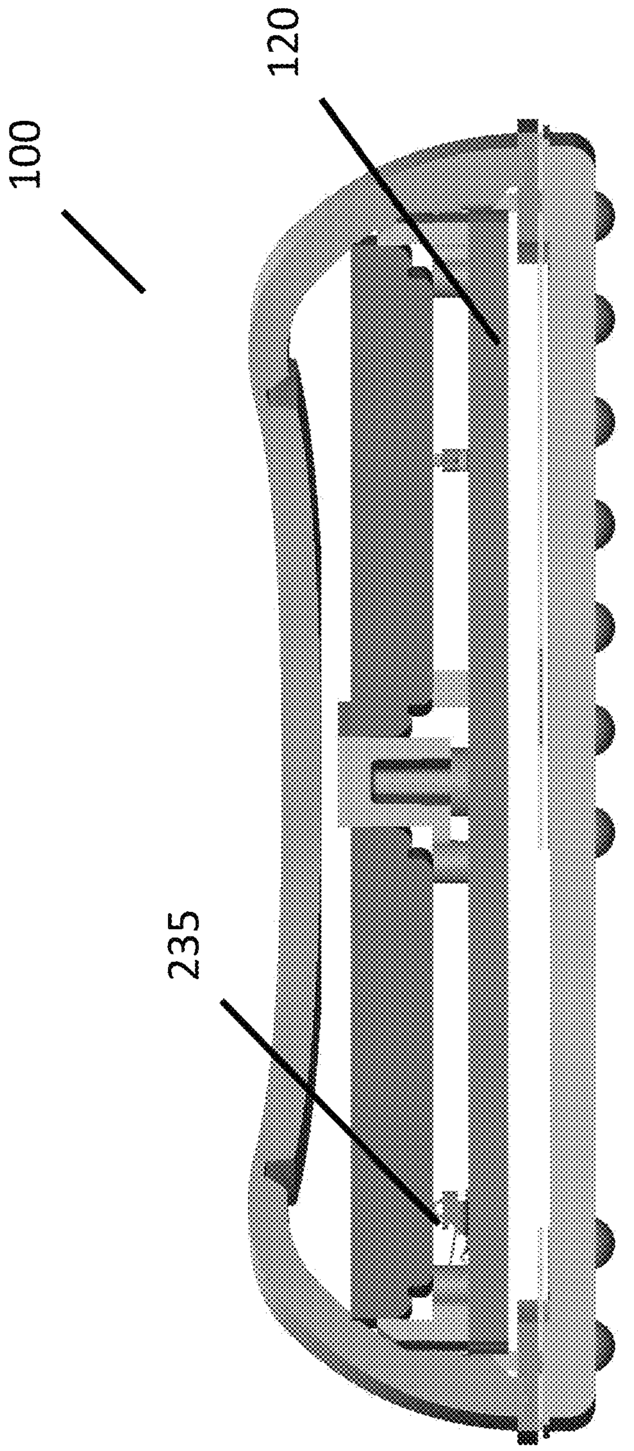

Referring now to FIG. 5A, battery holder 150 is shown in greater detail. Battery holder 150 may be made of plastic or other suitable material, is configured to be mounted to PCBA 120 and subsequently attached to rigid housing 115, and is capable of holding two batteries 160 (FIG. 1B). In alternative embodiments, battery holder 150 may be configured to hold one battery or more than two batteries. A plurality of protrusions 152 provide a stable platform for batteries 160 to be positioned a fixed distance above the surface of PCBA 120, avoiding unwanted contact with sensitive electronic components yet providing for adequate compression of spring contacts 235 (FIG. 5B). Protrusions 153 lock batteries 160 into position and resist the upward force on the batteries from spring contacts 235. Battery holder 150 also positions batteries appropriately 160 to provide for adequate compression of spring contacts 236. Use of battery holder 150 in conjunction with spring contacts 235 and 236 allows for batteries 160 to be electrically connected to PCBA 120 while still having additional electronic components between batteries 160 and PCBA 120 and maintain a very compact assembly. Battery holder 150 may include a flexible hook 510 which engages a corresponding rigid hook 440 of upper housing member 140. Under normal assembly conditions the flexible hook 510 remains securely mated with rigid hook 440. For disassembly, flexible hook 510 can be pushed and bent using an appropriate tool passed through top housing 140 causing it to disengage from rigid hook 440 and subsequently allow top housing 140 to be removed.

Figure 6A:
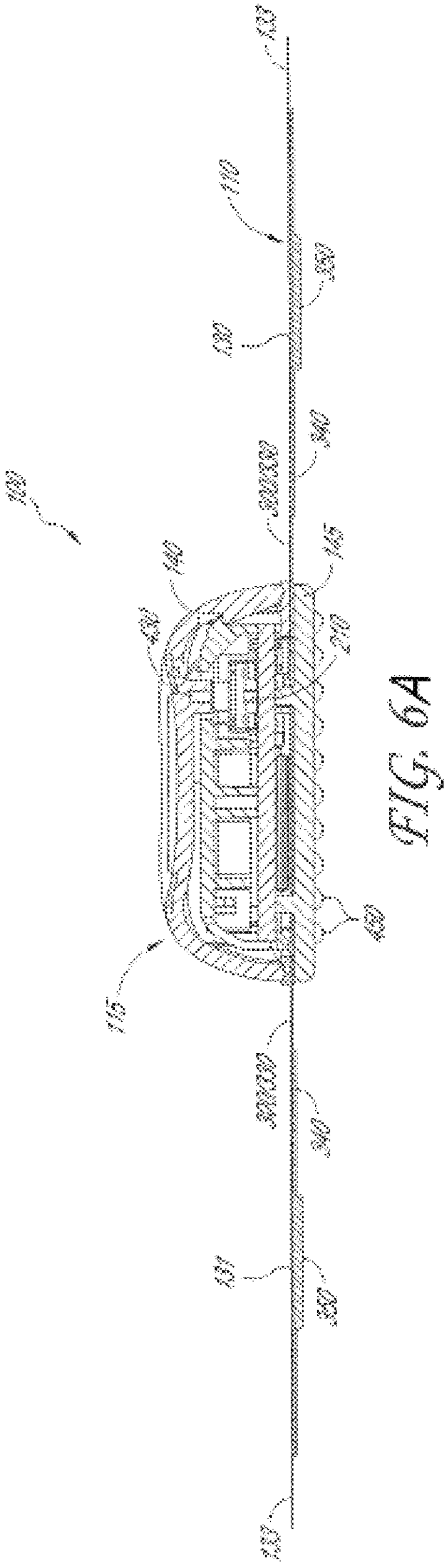
FIGS. 6A and 6B are cross sectional views of the physiological monitoring device.
Figure 6B:
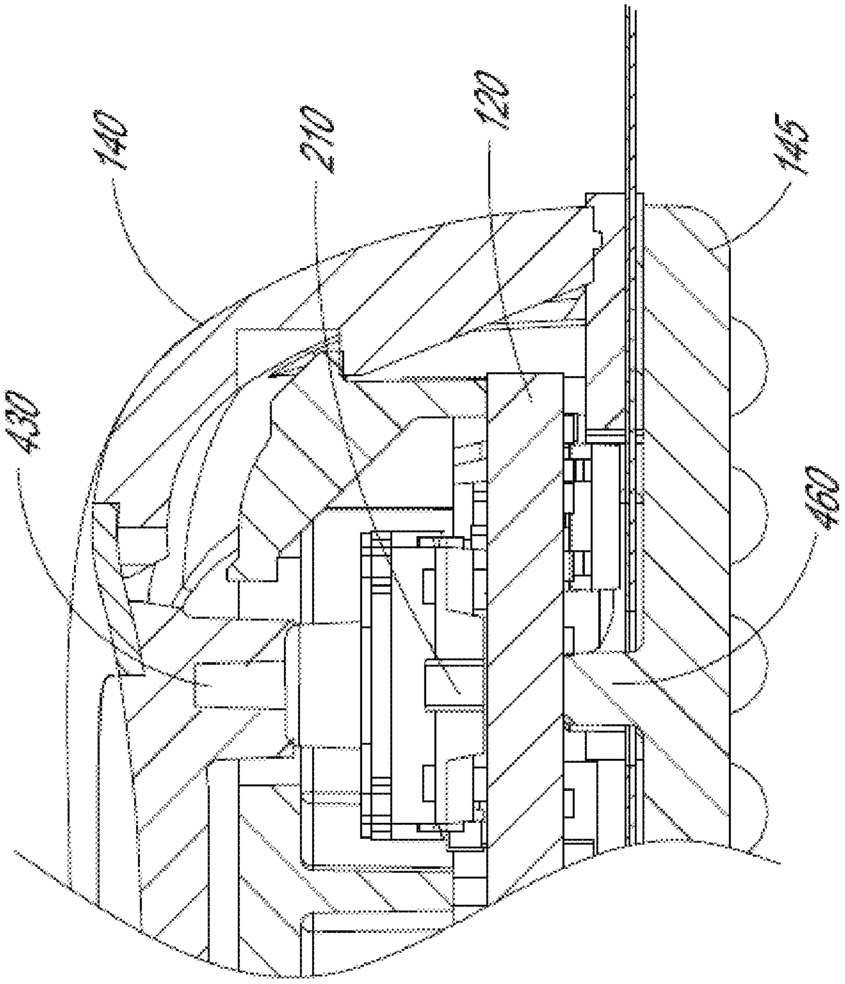

With reference now to FIGS. 6A and 6B, physiological monitoring device 100 is shown in side view cross-section. As shown in 6A, physiological monitoring device 100 may include flexible body 110 coupled with rigid housing 115. Flexible body 110 may include top substrate layer 300, bottom substrate layer 330, adhesive layer 340 and electrodes 350. Electrode traces 311, 312 are also typically part of flexible body 110 and are embedded between top substrate layer 300 and bottom substrate layer 330, but they are not shown in FIG. 6. Flexible body 110 forms two wings 130, 131, extending to either side of housing 115, and a border 133 surrounding at least part of each wing 130, 131. Rigid housing 115 may include an upper housing member 140 coupled with a lower housing member 145 such that it sandwiches a portion of flexible body 110 in between and provides a watertight, sealed compartment for PCBA 120. Upper housing member 140 may include inner trigger member 430, and PCBA may include patient trigger member 210. As discussed previously, lower housing member 145 may include multiple dimples 450 or divots to enhance the comfort of the monitoring device 100.

It is desirable that PCBA 120 is sufficiently rigid to prevent bending and introducing unwanted artifact into the signal. In certain embodiments, an additional mechanism to reduce and prevent unwanted bending of PCBA 120 may be used. This mechanism is shown in FIG. 6B. Support post 460 is integral to lower housing 145 and is positioned directly under patient trigger input 210. During patient symptom triggering, upper housing member 140 is depressed, engaging inner trigger mechanism 430 and transmitting a force through patient trigger input 210 into PCBA 120. The force is further transmitted through PCBA 120 and into support post 460 without creating a bending moment, thus avoiding unwanted artifact.

Figure 7:
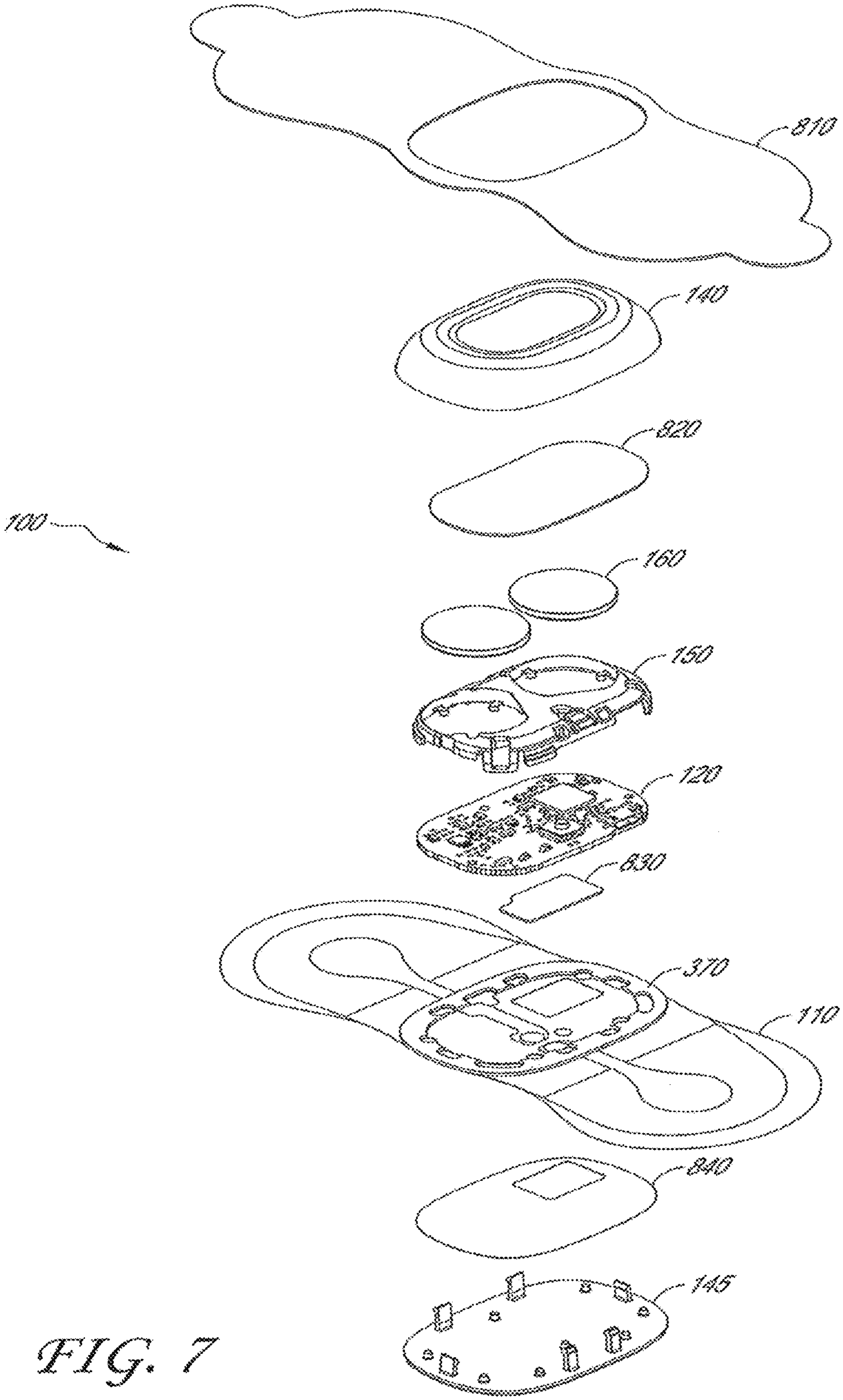
FIG. 7 is an exploded view of the physiological monitoring device including a number of optional items, according to one embodiment.

Referring to FIG. 7, in some embodiments, physiological monitoring device 100 may include one or more additional, optional features. For example, in one embodiment, monitoring device 100 may include a removable liner 810, a top label 820, a device identifier 830 and a bottom label 840. Liner 810 may be applied over a top surface of flexible member 110 to aid in the application of device 100 to the subject. As is described in further detail below, liner 810 may help support borders 133 of flexible body 110, as well as wings 130, 131, during removal of one or more adhesive covers (not shown) that cover adhesive surface 340 before use. Liner 810 may be relative rigid and/or firm, to help support flexible body 110 during removal of adhesive covers. In various embodiments, for example, liner 810 may be made of cardboard, thick paper, plastic or the like. Liner 810 typically includes an adhesive on one side for adhering to the top surface of wings 130, 131 of flexible body 110.

Labels 820, 840 may be any suitable labels and may include produce name(s), manufacturer name(s), logo(s), design(s) and/or the like. They may be removable or permanently attached upper housing member 140 and/or lower housing member 145, although typically they will be permanently attached, to avoid unregulated reuse and/or resale of the device by an unregistered user. Device identifier 830 may be a barcode sticker, computer readable chip, RFID, or the like. Device identifier 830 may be permanently or removably attached to PCBA 120, flexible body 110 or the like. In some embodiments, it may be beneficial to have device identifier 830 stay with PCBA 120.

Figure 8A:
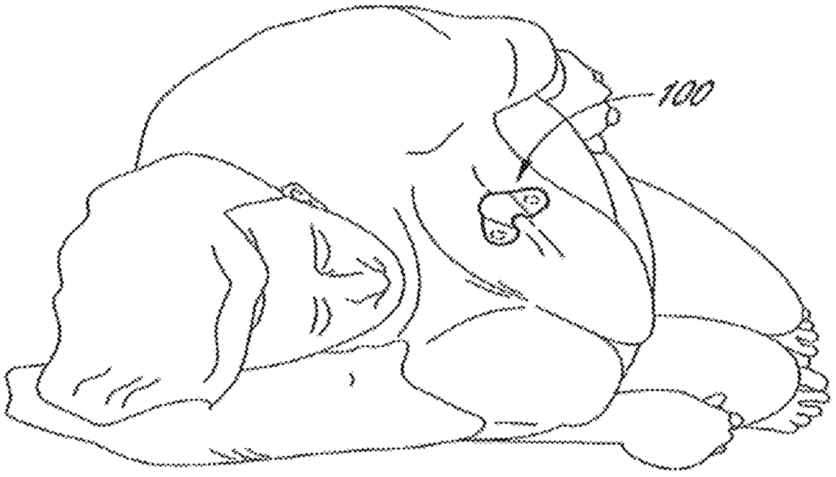
FIGS. 8A and 8B are perspective views of two people wearing the physiological monitoring device, illustrating how the device bends to conform to body movement and position.
Figure 8B:
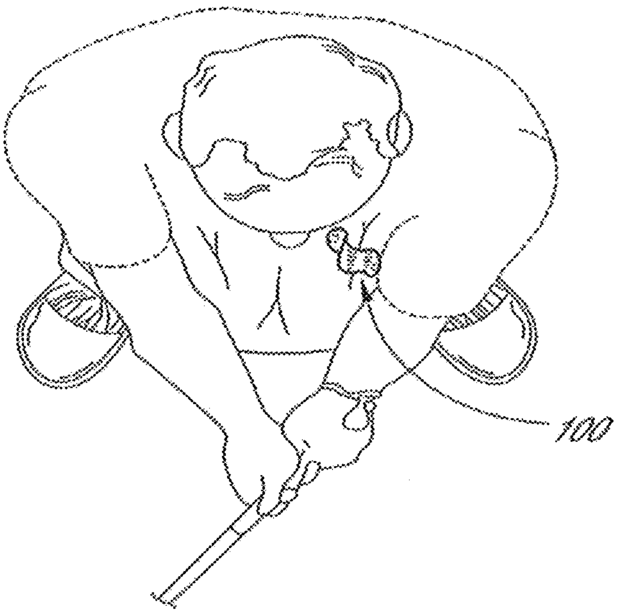

Referring now to FIGS. 8A and 8B, physiological monitoring device 100 generally includes hinge portions 132 at or near the juncture of each wing 130, 131 with rigid housing 115. Additionally, each wing 130, 131 is typically adhered to the patient via adhesive layers 340, while rigid body 115 is not adhered to the patient and is thus free to "float" (i.e., move up and down) over the patient's skin during movement and change of patient position. In other words, when the patient's chest contracts, rigid housing pops up or floats over the skin, thus minimizing stress on device 100, enhancing comfort, and reducing the tendency of wings 130, 131 to peel off of the skin. The advantage provided by the combination of the floating rigid body 115 and the adhered wings 130, 131 is illustrated in FIGS. 8A and 8B. In FIG. 8A, a patient is sleeping, and in FIG. 8B, a patient is playing golf. In both examples, monitoring device 100 is squeezed together by the patient's body, causing rigid housing 115 to float above the skin as wings 130, 131 move closer together. This advantage of a floating, non-attached portion of a physiological monitoring device is described in further detail in U.S. Pat. No. 8,560,046, which was previously incorporated by reference.

Figure 9A:
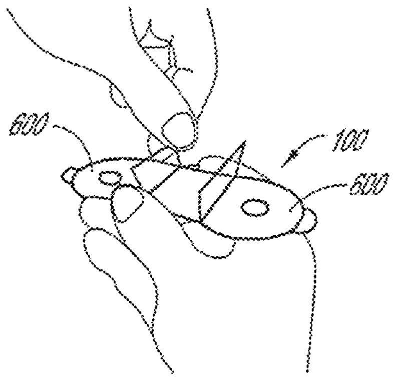
FIGS. 9A-9F illustrate various steps for applying the physiological monitor to a patient's body, according to one embodiment.
Figure 9B:
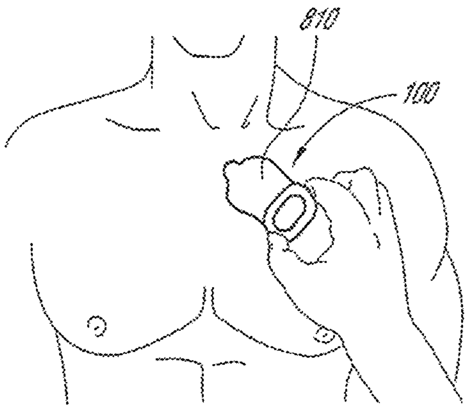
Figure 9C:
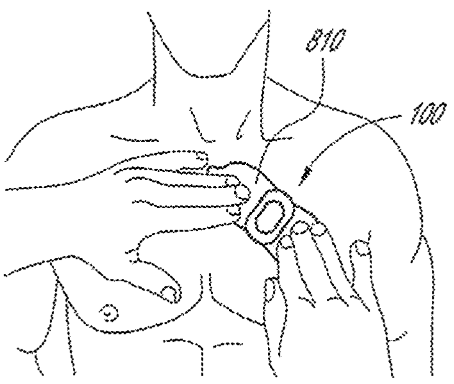

Referring now to FIGS. 9A-9F, one embodiment of a method for applying physiological monitoring device 100 to the skin of a human subject is described. In this embodiment, before the first step shown in FIG. 9A, the patient's skin may be prepared, typically by shaving a small portion of the skin on the left chest where device 100 will be placed and then abrading and/or cleaning the shaved portion. As shown in FIG. 9A, once the patient's skin is prepared, a first step of applying device 100 may include removing one or both of two adhesive covers 600 from adhesive layers 340 on the bottom surface of device 100, thus exposing adhesive layers 340. As illustrated in FIG. 9B, the next step may be to apply device 100 to the skin, such that adhesive layer 340 adheres to the skin in a desired location. In some embodiments, one adhesive cover 600 may be removed, the uncovered adhesive layer 340 may be applied to the skin, and then the second adhesive cover 600 may be removed, and the second adhesive layer 340 may be applied to the skin. Alternatively, both adhesive covers 600 may be removed before applying device 100 to the skin. While adhesive covers 600 are being removed, liner 810 acts as a support for flexible body 110, provides the physician or other user with something to hold onto, and prevents flexible body 110 and borders 133 of flexible body 110 from folding in on themselves, forming wrinkles, etc. As described above, liner 810 may be made of a relatively stiff, firm material to provide support for flexible body 110 during application of device 100 to the skin. Referring to FIG. 9C, after device 100 has been applied to the skin, pressure may be applied to flexible body 110 to press it down onto the chest to help ensure adherence of device 100 to the skin.

Figure 9D:
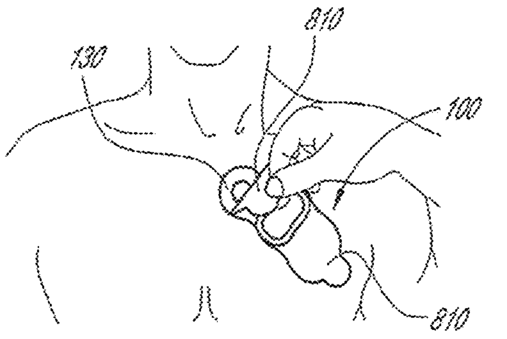
Figure 9E:
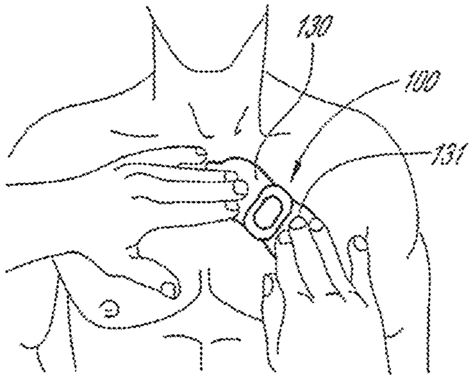
Figure 9F:
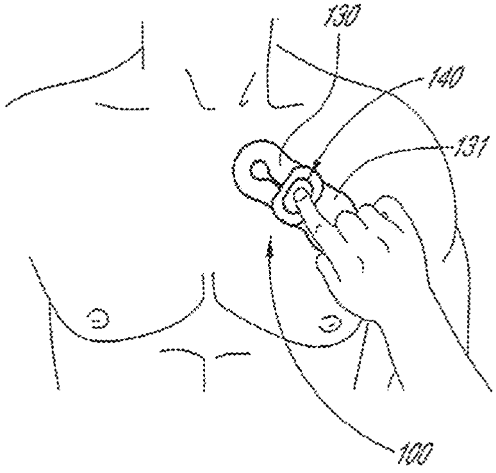

In a next step, referring to FIG. 9D, liner 810 is removed from (peeled off of) the top surface of flexible body 110. As shown in FIG. 9E, once liner 810 is removed, pressure may again be applied to flexible body 110 to help ensure it is adhered to the skin. Finally, as shown in FIG. 9F, upper housing member 140 may be pressed to turn on physiological monitoring device 140. This described method is only one embodiment. In alternative embodiments, one or more steps may be skipped and/or one or more additional steps may be added.

When a desired monitoring period has ended, such as about 14-21 days in some cases, a patient (or physician, nurse or the like) may remove physiological monitoring device 100 from the patient's skin, place device 100 in a prepaid mailing pouch, and mail device 100 to a data processing facility. At this facility, device 100 may be partially or completely disassembled, PCBA 120 may be removed, and stored physiological data, such as continuous heart rhythm information, may be downloaded from PCBA 120. The data may then be analyzed by any suitable method and then provided to a physician in the form of a report. The physician may then discuss the report with the patient. PCBA 120 and/or other portions of device 100, such as rigid housing 115, may be reused in the manufacture of subsequent devices for the same or other patients. Because device 100 is built up as a combination of several removably coupled parts, various parts may be reused for the same embodiment or different embodiments of device 100. For example, PCBA 120 may be used first in an adult cardiac rhythm monitor and then may be used a second time to construct a monitor for sleep apnea. The same PCBA 120 may additionally or alternatively be used with a differently sized flexible body 110 to construct a pediatric cardiac monitor. Thus, at least some of the component parts of device 100 may be interchangeable and reusable.

Advantageously, physiological monitoring device 100 may provide long term adhesion to the skin. The combination of the configuration of flexible and conformal body 110, the watertight, low profile configuration of rigid housing 115, and the interface between the two allows device 100 to compensate for stress caused as the skin of the subject stretches and bends. As a result, device 100 may be worn continuously, without removal, on a patient for as many as 14-21 days or more. In some cases, device 100 may be worn for greater or less time, but 14-21 days may often be a desirable amount of time for collecting heart rhythm data and/or other physiological signal data from a patient.

In various alternative embodiments, the shape of a particular physiological monitoring device may vary. The shape, footprint, perimeter or boundary of the device may be circular, an oval, triangular, a compound curve or the like, for example. In some embodiments, the compound curve may include one or more concave curves and one or more convex curves. The convex shapes may be separated by a concave portion. The concave portion may be between the convex portion on the rigid housing and the convex portion on the electrodes. In some embodiments, the concave portion may correspond at least partially with a hinge, hinge region or area of reduced thickness between the body and a wing.

While described in the context of a heart monitor, the device improvements described herein are not so limited. The improvements described in this application may be applied to any of a wide variety of physiological data monitoring, recording and/or transmitting devices. The improved adhesion design features may also be applied to devices useful in the electronically controlled and/or time released delivery of pharmacological agents or blood testing, such as glucose monitors or other blood testing devices. As such, the description, characteristics and functionality of the components described herein may be modified as needed to include the specific components of a particular application such as electronics, antenna, power supplies or charging connections, data ports or connections for down loading or off loading information from the device, adding or offloading fluids from the device, monitoring or sensing elements such as electrodes, probes or sensors or any other component or components needed in the device specific function. In addition or alternatively, devices described herein may be used to detect, record, or transmit signals or information related to signals generated by a body including but not limited to one or more of ECG, EEG and/or EMG.

While the above embodiments disclose the invention with respect to a data channel for collecting a single physiological signal, it is contemplated that additional data channels can be include to collect additional data, for example, device motion, device flex or bed, heart rate and/or ambient electrical noise.

Various embodiments of a physiological monitoring device and methods for using it have been disclosed above. These various embodiments may be used alone or in combination, and various changes to individual features of the embodiments may be altered, without departing from the scope of the invention. For example, the order of various method steps may in some instances be changed, and/or one or more optional features may be added to or eliminated from a described device. Therefore, the description of the embodiments provided above should not be interpreted as unduly limiting the scope of the invention as it is set forth in the claims.

Various modifications to the implementations described in this disclosure may be made, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

Certain features that are described in this specification in the context of separate embodiments also can be implemented in combination in a single embodiment. Conversely, various features that are described in the context of a single embodiment also can be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, such operations need not be performed in the particular order shown or in sequential order, or that all illustrated operations be performed, to achieve desirable results. Further, the drawings may schematically depict one more example processes in the form of a flow diagram. However, other operations that are not depicted can be incorporated in the example processes that are schematically illustrated. For example, one or more additional operations can be performed before, after, simultaneously, or between any of the illustrated operations. Moreover, the separation of various system components in the embodiments described above should not be interpreted as requiring such separation in all embodiments. Additionally, other embodiments are within the scope of the following claims. In some cases, the actions recited in the claims can be performed in a different order and still achieve desirable results.

What is claimed is:

1. A wearable cardiac signal monitoring device, comprising:

a removable component configured to monitor and create a record of a cardiac rhythm signal, the removable component including electronic components comprising a processor, a first printed circuit board, and a light-emitting diode (LED), wherein the removable component is configured to be connected, physically and electrically, to other device components, wherein the removable component is configured to be removed from the wearable cardiac signal monitoring device and sent for data processing after a particular time period for cardiac rhythm signal monitoring is over, and wherein a portion of the removable component is substantially rigid to prevent deflections of the electronic components and the introduction of noise or artifacts into the recorded cardiac rhythm signal; and a flexible body comprising multiple layers, including a flexible polymer layer, wherein the flexible body includes a flexible electrode trace, borders of the flexible body have rounded edges, and the flexible body is configured to flex at an area between the removable component and an electrode disposed on a bottom surface of the wearable cardiac monitoring device, wherein at least one layer of the flexible body extends beyond at least one other layer of the flexible body creating an edge to the flexible body that is thinner than an inner portion of the flexible body.

2. The wearable cardiac signal monitoring device of claim 1, wherein the electrode is positioned so as to not be beneath the removable component.

3. The wearable cardiac signal monitoring device of claim 1, wherein the electrode is embedded within a portion of the flexible body.

4. The wearable cardiac signal monitoring device of claim 1, wherein the flexible electrode trace is sandwiched between a first layer and a second layer of the flexible body.

5. The wearable cardiac signal monitoring device of claim 1, further comprising an adhesive layer located on at least a portion of the flexible body and configured to adhere to skin of a patient.

6. The wearable cardiac signal monitoring device of claim 5, wherein the adhesive layer is configured to adhere to the skin of the patient for at least 7 days enabling the wearable cardiac signal monitoring device to monitor the cardiac rhythm signal of the patient for at least 7 days.

7. The wearable cardiac monitoring device of claim 1, wherein the LED is configured to indicate activation of the wearable cardiac signal monitoring device.

8. The wearable cardiac monitoring device of claim 1, further comprising a support post.

9. The wearable cardiac monitoring device of claim 8, further comprising a physical event trigger, the physical event trigger configured such that force from interaction with the physical event trigger is transmitted to the support post.

* * * * *